United States Patent
Karni

(10) Patent No.: US 10,781,445 B2
(45) Date of Patent: Sep. 22, 2020

(54) DECOY OLIGONUCLEOTIDES FOR THE TREATMENT OF DISEASES

(71) Applicant: Yissum Research Development Company of the Hebrew University of Jerusalem Ltd., Jerusalem (IL)

(72) Inventor: Rotem Karni, Mevasseret Zion (IL)

(73) Assignee: Yissum Research Development Company of the Hebrew University of Jerusalem Ltd., Jerusalem (IL)

( * ) Notice: Subject to any disclaimer, the term of this patent is extended or adjusted under 35 U.S.C. 154(b) by 0 days.

(21) Appl. No.: 15/528,769

(22) PCT Filed: Mar. 10, 2016

(86) PCT No.: PCT/IL2016/050265
§ 371 (c)(1),
(2) Date: May 23, 2017

(87) PCT Pub. No.: WO2016/142948
PCT Pub. Date: Sep. 15, 2016

(65) Prior Publication Data
US 2017/0327825 A1 Nov. 16, 2017

Related U.S. Application Data

(60) Provisional application No. 62/131,426, filed on Mar. 11, 2015.

(51) Int. Cl.
*C12N 15/113* (2010.01)
*C12N 15/115* (2010.01)
*C07H 21/00* (2006.01)

(52) U.S. Cl.
CPC ........... *C12N 15/113* (2013.01); *C07H 21/00* (2013.01); *C12N 15/115* (2013.01); *C12N 2310/13* (2013.01); *C12N 2310/314* (2013.01); *C12N 2310/3181* (2013.01); *C12N 2310/321* (2013.01); *C12N 2310/3231* (2013.01); *C12N 2310/3233* (2013.01); *C12N 2310/3521* (2013.01)

(58) Field of Classification Search
CPC ... C12N 15/113; C07H 21/00; A61K 31/7088
See application file for complete search history.

(56) References Cited

U.S. PATENT DOCUMENTS

| | | | |
|---|---|---|---|
| 2004/0219575 A1* | 11/2004 | Neuman | C12Q 1/6886 435/6.14 |
| 2008/0194027 A1 | 8/2008 | Dreyfuss et al. | |
| 2009/0176724 A1* | 7/2009 | Shen | C12Q 1/6886 514/44 R |
| 2011/0009476 A1* | 1/2011 | McArthur | C12N 15/1048 514/44 R |
| 2012/0129179 A1* | 5/2012 | Dudley | C12Q 1/6883 435/6.12 |
| 2014/0128449 A1 | 5/2014 | Liu et al. | |
| 2016/0289681 A1* | 10/2016 | Rossi | C12N 15/1131 |

FOREIGN PATENT DOCUMENTS

| | | | |
|---|---|---|---|
| WO | WO 99/57265 | 11/1999 | |
| WO | WO-2004016787 A1 * | 2/2004 | C12N 15/113 |
| WO | WO 2016/142948 | 9/2016 | |

OTHER PUBLICATIONS

Manabe et al. Genes to Cells 12, 1179-1191 (Year: 2007).*
Tsuruno et al. Biochemical and Biophysical Research Communications 406, 512-517 (Year: 2011).*
Communication Under Rule 164(2)(a) EPC dated Jan. 19, 2018 From the European Patent Office Re. Application No. 16714551.5. (6 pages).
Communication Relating to the Result of the Partial International search dated Jun. 24, 2016 From the International Searching Authority Re. Application No. PCT/IL2016/050265.
International Search Report and the Written Opinion dated Aug. 30, 2016 From the International Searching Authority Re. Application No. PCT/IL2016/050265.
Burd et al. "RNA Binding Specificity of HnRNP A1: Significance of HnRNP A1 High-Affinity Binding Sites in Pre-mRNA Splicing", The EMBO Journal, XP001156209, 13(5): 1197-1204, Jan. 1, 1994. Oligo Alwinner, Fig. 4.
Cavaliere et al. "Cross-Talk Between Prion Protein and Quadruplex-Forming Nucleic Acids: A Dynamic Complex Formation", Nucleic Acids Research, XP055279113, 41(1): 327-339, Published Online Oct. 27, 2012, p. 2, 1-h, Col., Para 2.
Gendron et al. "Modulation of 5' Splice Site Selection Using Tailed Oligonucleotides Carrying Splicing Signals", BMC Biotechnology, XP021017067, 6(1): 5-1-5-12, Jan. 13, 2006. Fig.6.
Owen et al. "Design Principles for Bifunctional Targeted Oligonucleotide Enhancers of Splicing", Nucleic Acids Research, 39(16): 7194-7208, Sep. 2011.
Ponthier et al. "Fox-2 Splicing Factor Binds to A Conserved Intron Motif to Promote Inclusion of Protein 4.1R Alternative Exon 16", The Journal of Biological Chemistry, XP055271843, 281(18): 12468-12474, Published Online Mar. 14, 2006. p. 12469, r-h Col., Last Para.
Skordis et al. "Bifunctional Antisense Oligonucleotides Provide A Trans-Acting Splicing Enhancer That Stimulates SMN2 Gene Expression in Patient Fibroblasts", Proc. Natl. Acad. Sci. USA, PNAS, XP00262730, 100(7): 4114-4119, Apr. 1, 2003. Materials and Methods.

(Continued)

*Primary Examiner* — Brian Whiteman

(57) ABSTRACT

An isolated oligonucleotide comprising ribonucleotides is disclosed. The oligonucleotide comprises a nucleic acid sequence which encodes at least one copy of a splicing-factor binding site. The oligonucleotide is no more than 150 bases and may be devoid of a sequence that allows hybridization thereof to cellular RNA under physiological conditions. The oligonucleotide inhibits overall cellular splicing activity of a specific splicing factor. Pharmaceutical compositions comprising the oligonucleotide and uses thereof are further disclosed.

6 Claims, 29 Drawing Sheets
(25 of 29 Drawing Sheet(s) Filed in Color)
Specification includes a Sequence Listing.

(56) References Cited

OTHER PUBLICATIONS

Villemaire et al. "Reprogramming Alternative Pre-Messenger RNA Splicing Through the Use of Protein-Binding Antisense Olignucleotides", The Journal of Biological Chemistry, XP055279217. 278(50): 50031-50039, Dec. 12, 2003. Fig.4a.
International Preliminary Report on Patentability dated Sep. 21, 2017 From the International Bureau of WIPO Re. Application No. PCT/IL2016/050265.
Communication Pursuant to Article 64(3) EPC dated May 9, 2018 From the European Patent Office Re. Application No. 16714551.5. (5 Pages).
Communication Pursuant to Article 94(3) EPC dated Feb. 18, 2019 From the European Patent Office Re. Application No. 16714551.5. (6 Pages).
Communication Pursuant to Article 94(3) EPC dated Oct. 14, 2019 From the European Patent Office Re. Application No. 16714551.5. (5 Pages).

\* cited by examiner

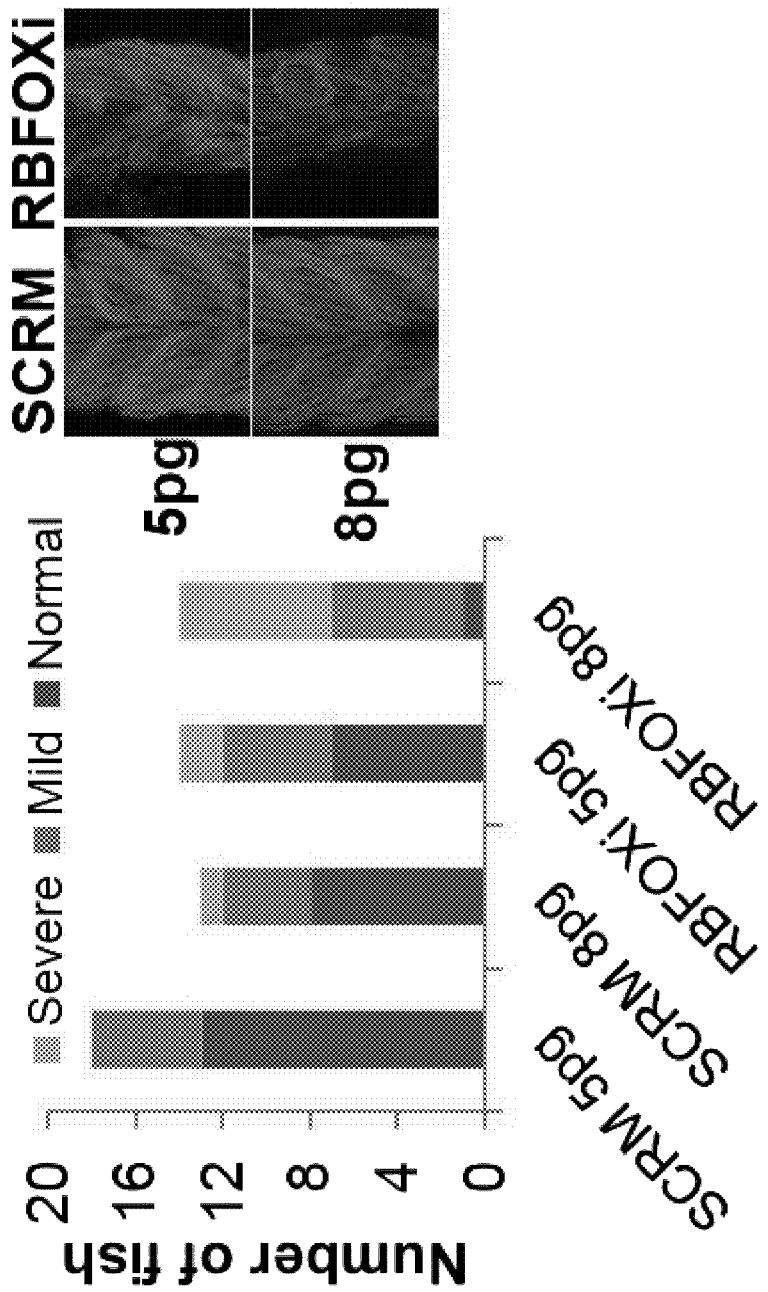

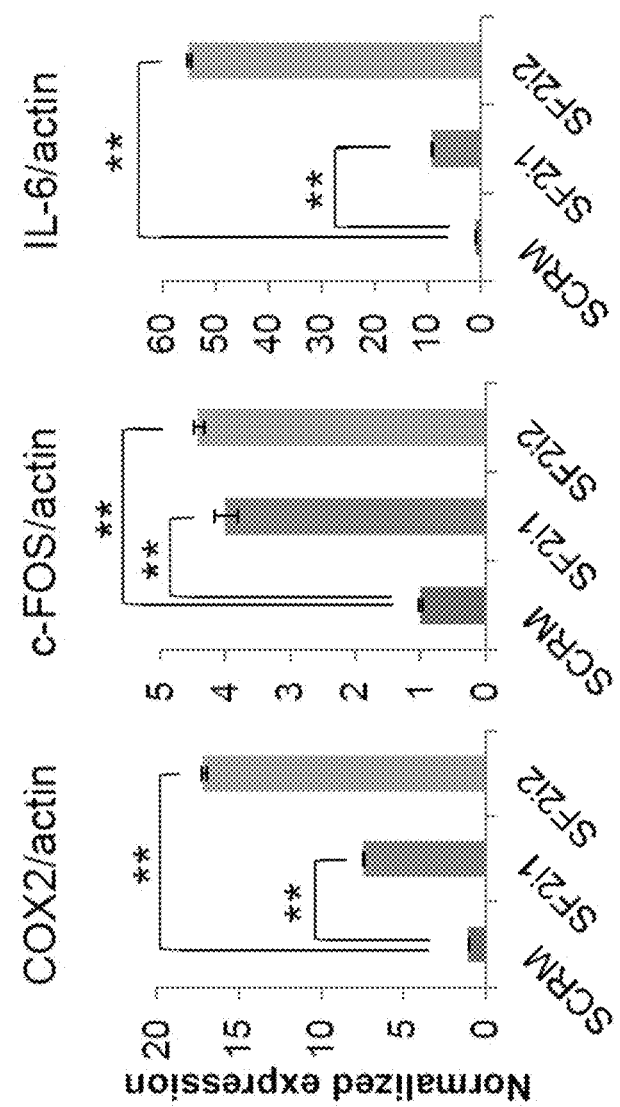
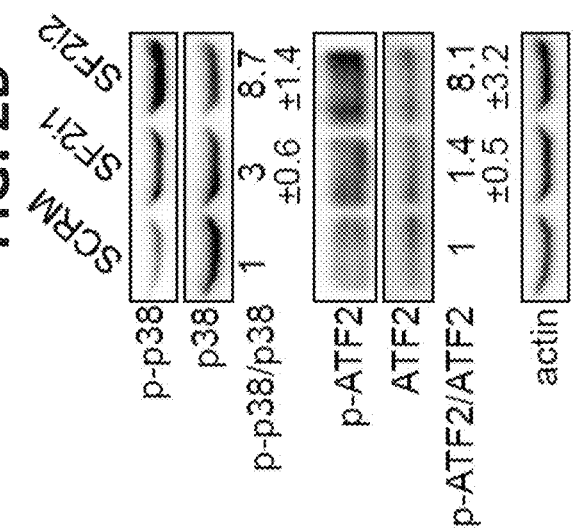
FIG. 2B
FIG. 2C

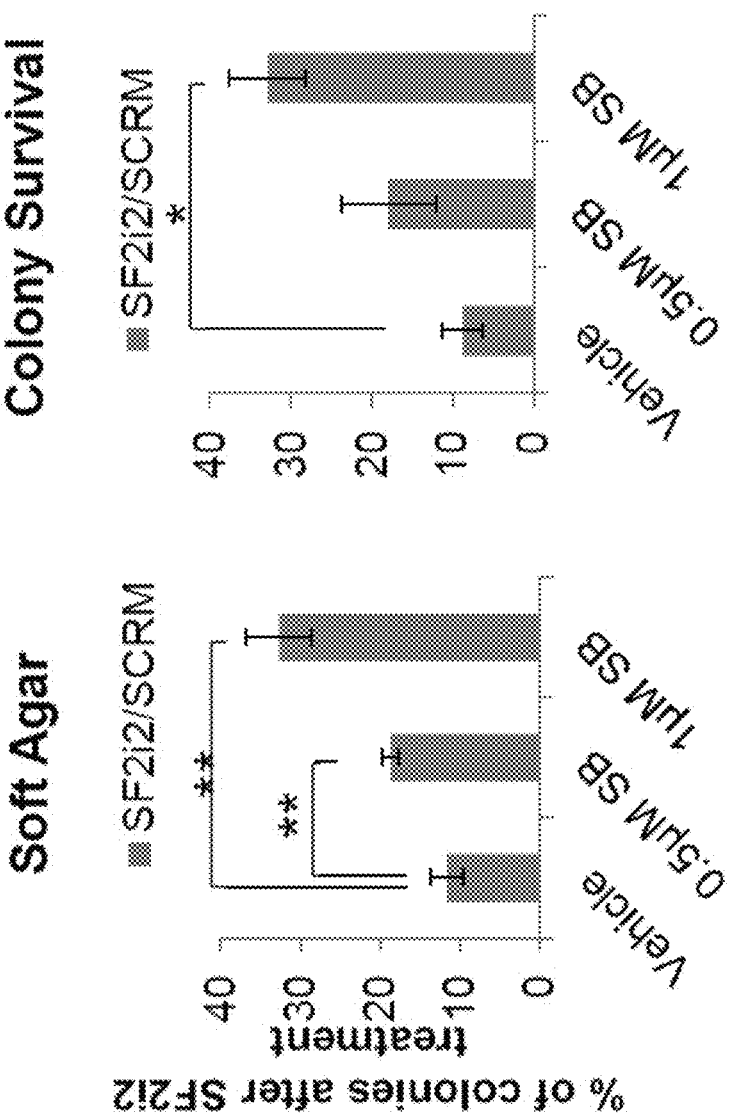
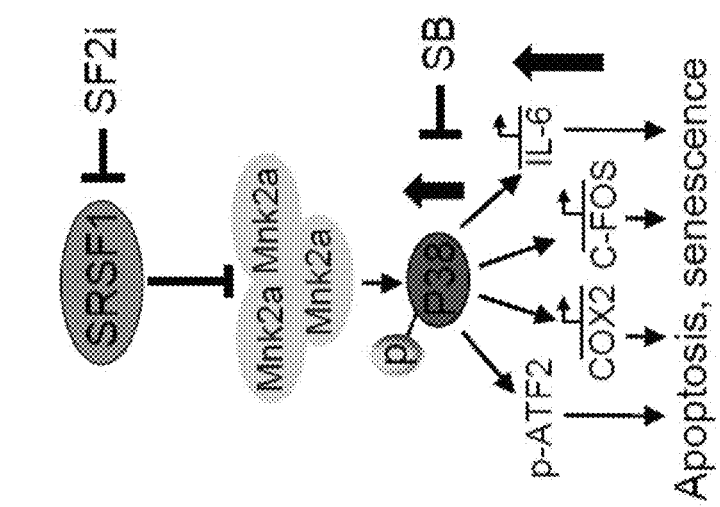
FIG. 3D
FIG. 3E
FIG. 3F

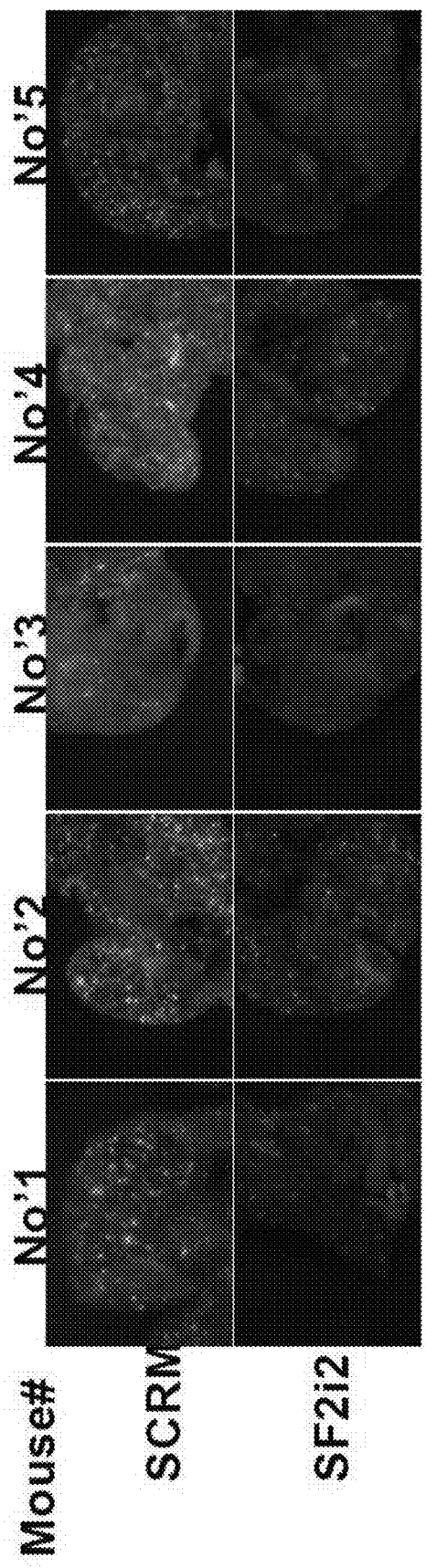

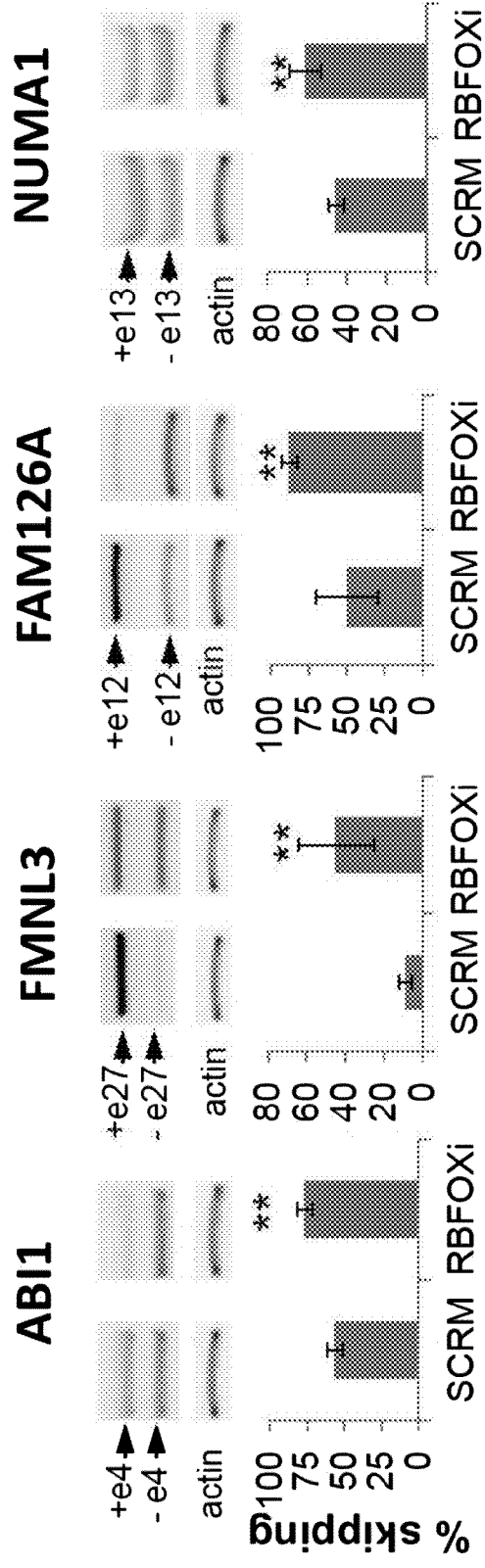

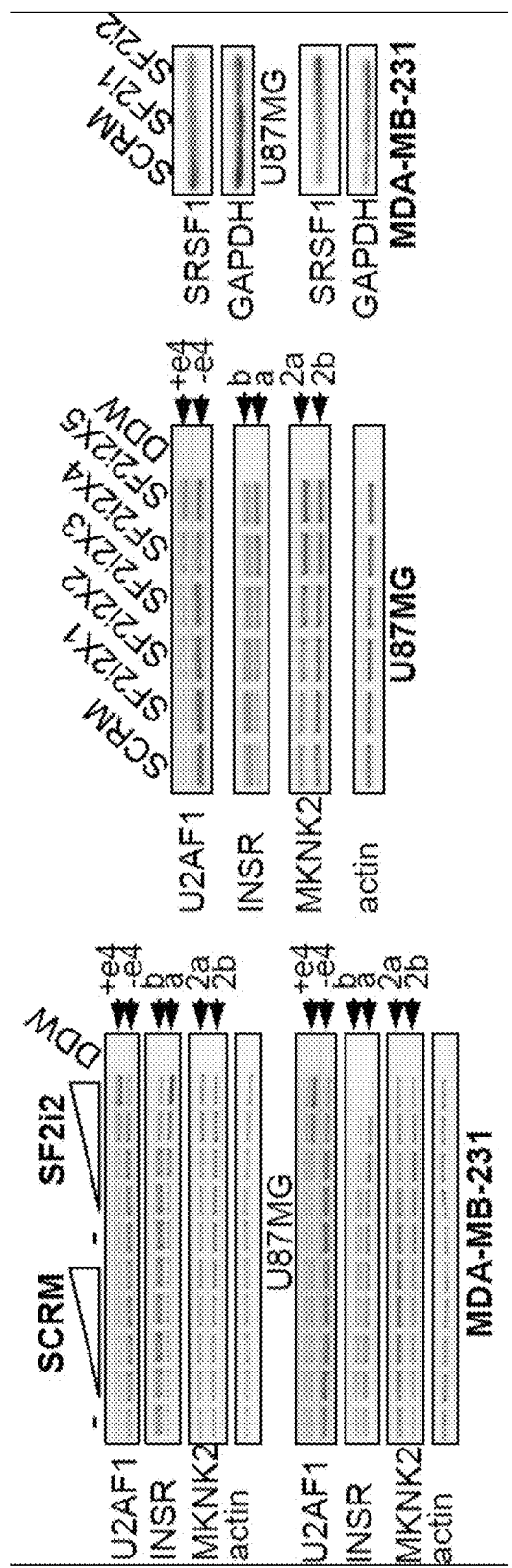

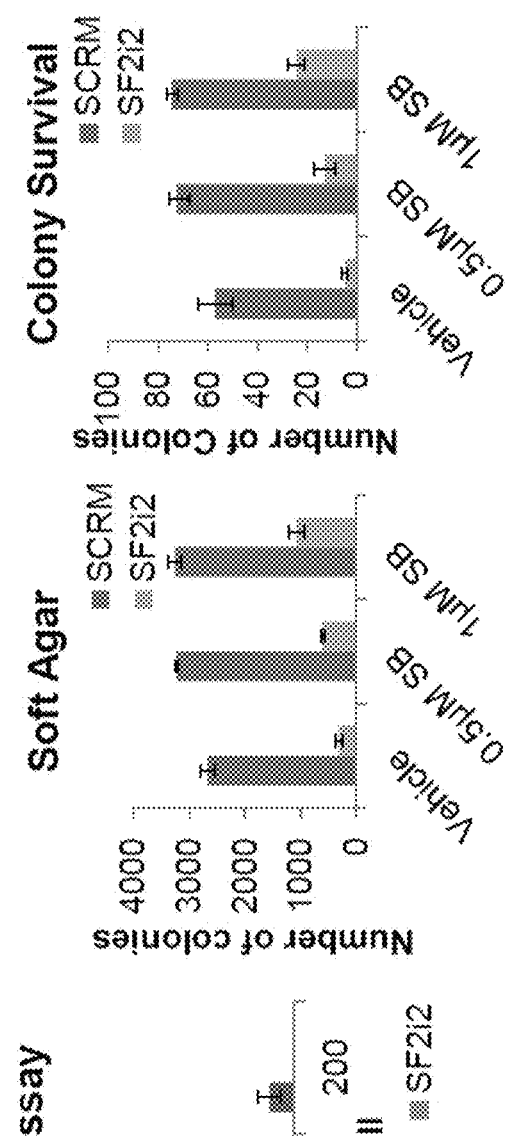
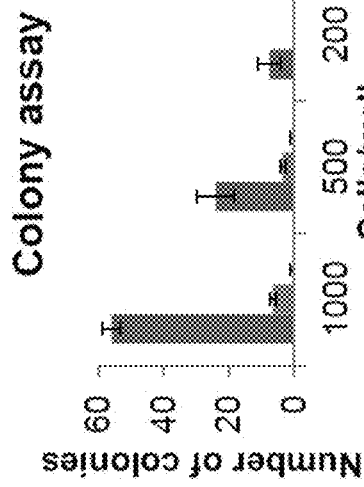
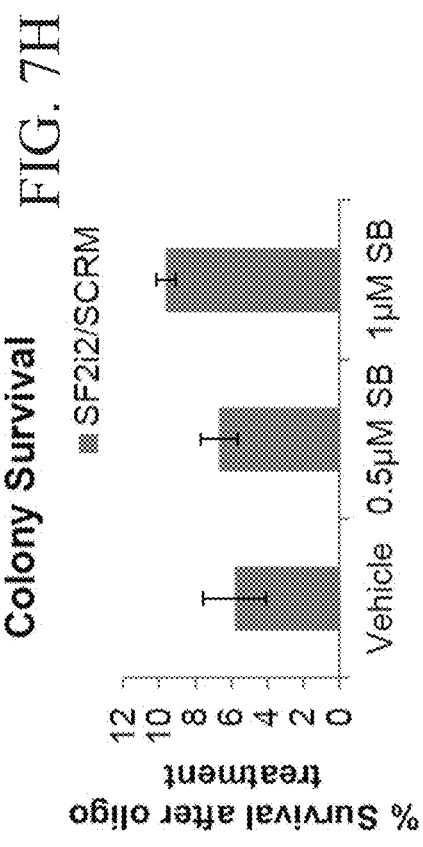
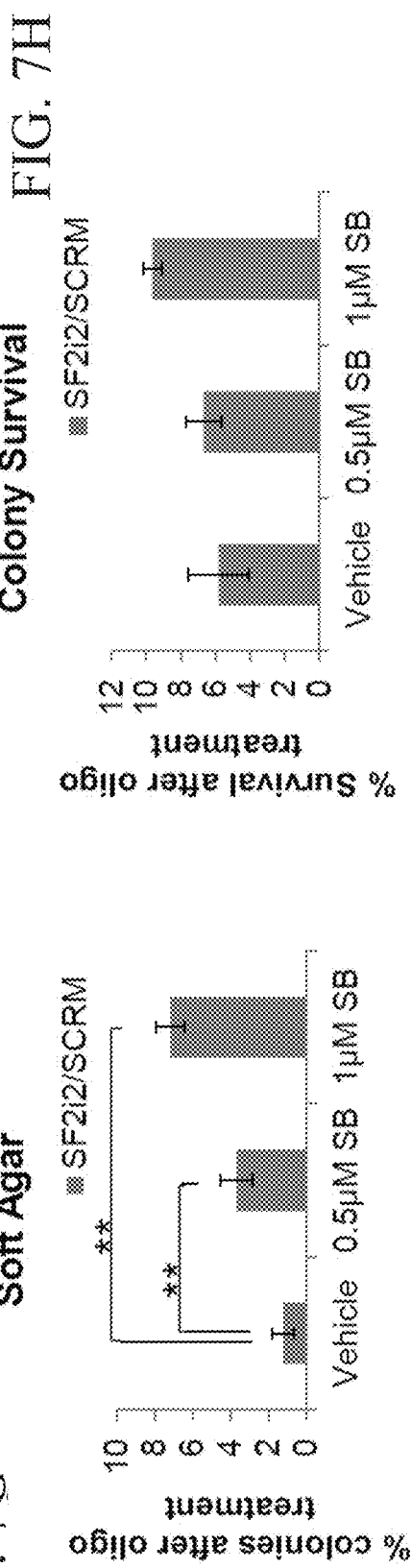
FIG. 7D  FIG. 7E  FIG. 7F  FIG. 7G  FIG. 7H

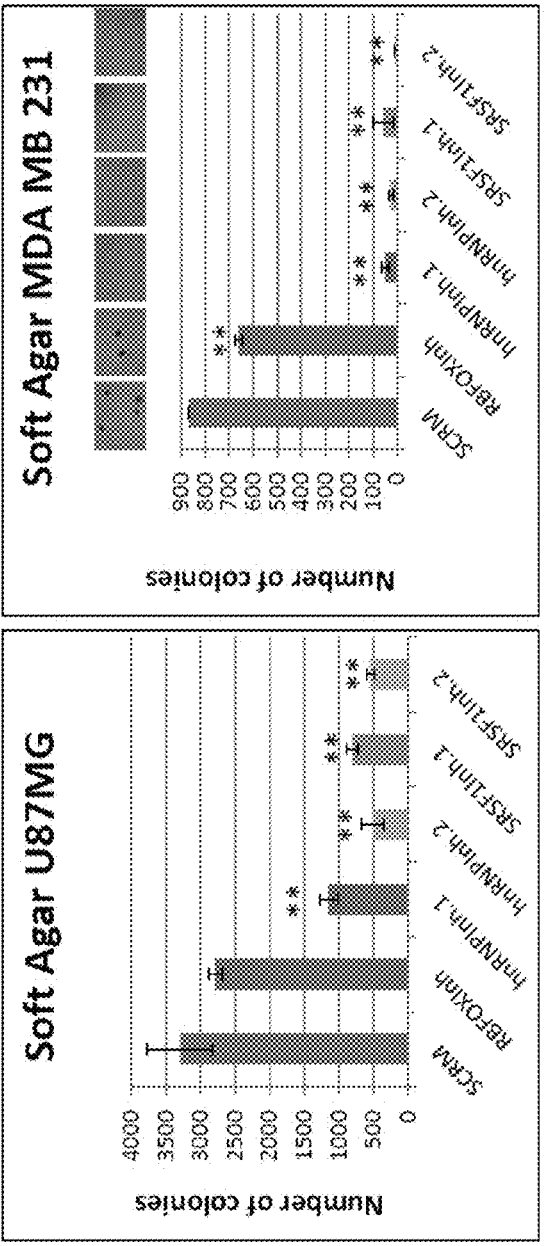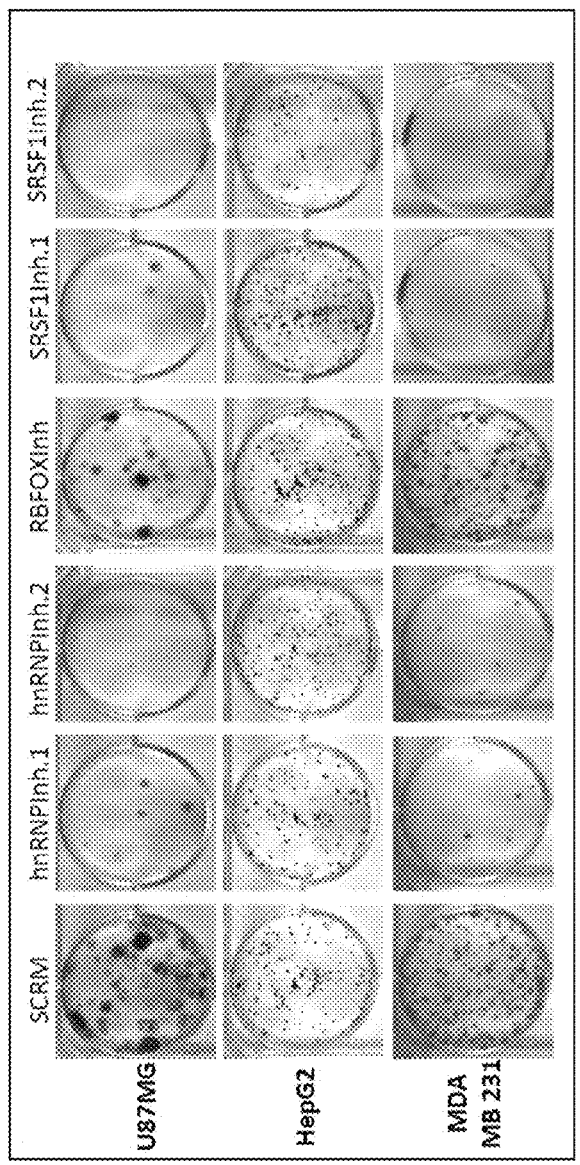

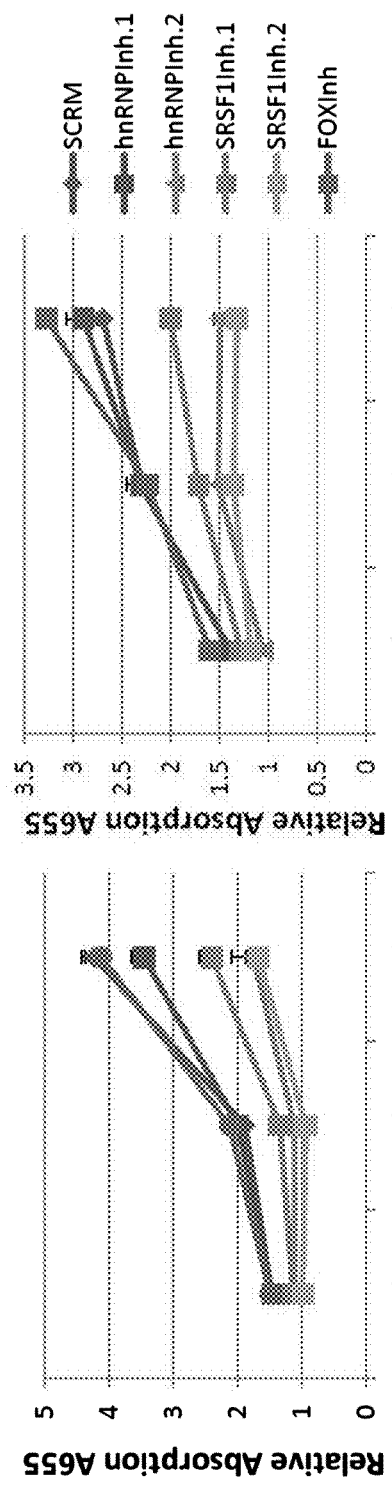
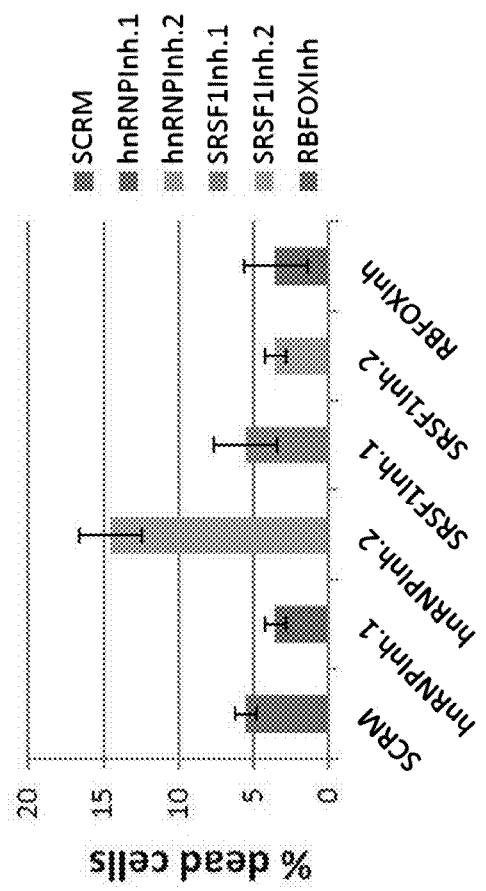
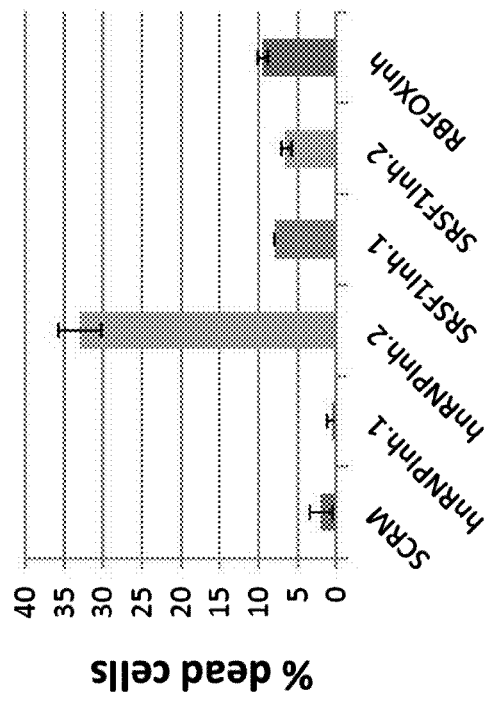
FIG. 9A
FIG. 9B

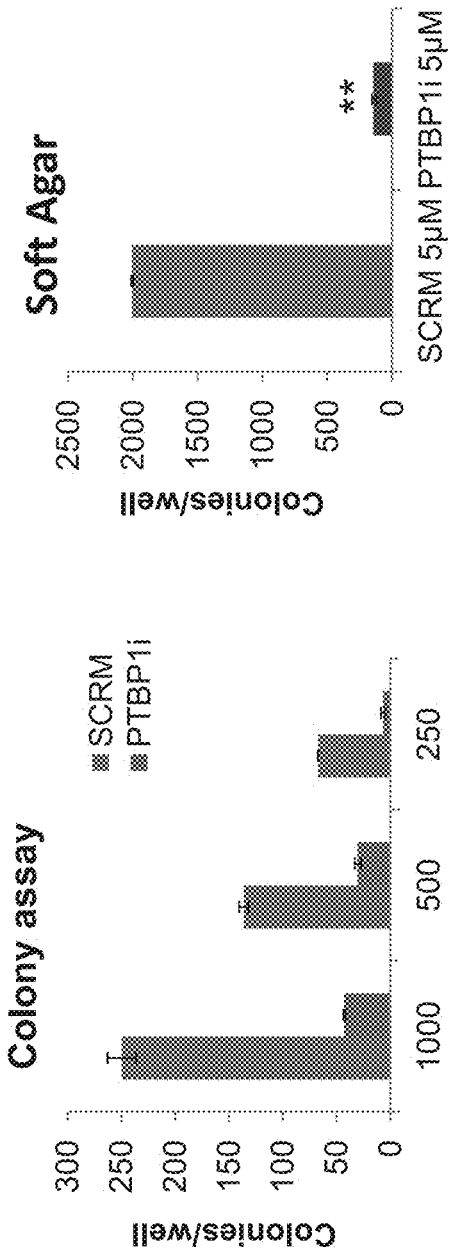

DECOY OLIGONUCLEOTIDES FOR THE TREATMENT OF DISEASES

RELATED APPLICATIONS

This application is a National Phase of PCT Patent Application No. PCT/IL2016/050265 having International filing date of Mar. 10, 2016, which claims the benefit of priority under 35 USC § 119(e) of U.S. Provisional Patent Application No. 62/131,426 filed on Mar. 11, 2015. The contents of the above applications are all incorporated by reference as if fully set forth herein in their entirety.

SEQUENCE LISTING STATEMENT

The ASCII file, entitled 69475SequenceListing.txt, created on May 23, 2017, comprising 29,467 bytes, submitted concurrently with the filing of this application is incorporated herein by reference.

FIELD AND BACKGROUND OF THE INVENTION

The present invention, in some embodiments thereof, relates to decoy oligonucleotides encoding splicing-factor binding sites for the treatment of diseases.

Eukaryotic mRNAs are transcribed as precursors, or pre-mRNAs, which contain intronic sequences. These intronic sequences are excised and the exons are spliced together to form mature mRNA. The basic biochemical reactions involved in splicing are relatively well-known. A transcribed pre-mRNA contains a 5' exon-intron junction, or splice site, which is marked by the consensus sequence CAG/GTAAGT (SEQ ID NO: 113) (where/is the exon-intron junction); a 3' splice site marked by the consensus sequence YnCAG/ (Y=Pyrimidines and n=3 to 12; SEQ ID NO: 114); a branchpoint about 25-100 nucleotides upstream of the 3' splice site; and a polypyrimidine track. The splicing event itself requires the binding of several RNA binding proteins and ribonucleoprotein particles (e.g. snRNPs) to form the spliceosome. After spliceosome assembly, two transesterification reactions follow which result in the fusion of the two exon sequences and the release of the lariat-shaped intron.

Given the number of introns and the potential splice sites within a given gene, alternative splicing can produce a variety of mRNA products from one pre-mRNA molecule. The consequences of alternative splicing range from controlling protein expression, by excluding and including stop codons, to allowing for the diversification of protein products. Alternative splicing plays an extremely important role in expanding the protein repertoire of any given species by allowing for more transcripts and therefore protein products from a single gene.

The effect of alternatively including or excluding exons, portions of exons, or introns, can have a broad range of effects on the structure and activity of proteins. In some transcripts, whole functional domains (e.g., DNA binding domain, transcription-activating domain, membrane-anchoring domain, localization domain) can be added or removed by alternative splicing. In other examples, the inclusion of an exon carrying a stop codon can yield a shortened and sometimes inactive protein. In other systems, the introduction of an early stop codon can result in a truncated protein, transforming a membrane bound protein into a soluble protein, for example, or an unstable mRNA. The differential use of splice sites is often regulated in a developmental, cellular, tissue, and sex-specific manner. The functional impact of alternative splicing in a variety of cellular processes including neuronal connectivity, electrical tuning in hair cells, tumor-progression, apoptosis, and signaling events, is just starting to be documented.

Perturbations in alternative splicing have been associated with human genetic diseases and cancer. There are many examples of cancers where an alternatively spliced isoform of a protein has increased ligand affinity or loss of tumor suppressor activity which contributes to neoplastic growth. For example, the inappropriate inclusion of exons in BIN1 mRNA results in the loss of tumor suppressor activity.

Also of particular interest is the contribution of alternative splicing to the control of apoptosis, or programmed cell death. Overexpression of anti-apoptotic proteins (e.g., Bcl-2, Bcl-xL, Bcl-w, Mcl-1) or blocking the expression of pro-apoptotic proteins (e.g., Bax, Bim, Bcl-xS, Bcl-G) protects cells against death stimuli. In contrast, preventing the expression of anti-apoptotic forms promotes or sensitizes cells to death stimuli, a situation also observed by overexpressing pro-apoptotic Bcl-2 family members. Thus, apoptotic pathways are controlled via a delicate balance between pro- and anti-apoptotic activities and alternative splicing is one mechanism used for careful regulation of the cellular response to death signals.

In a number of cancers and cancer cell lines, the ratio of the splice variants is frequently shifted to favor production of the anti-apoptotic form. For example, overexpression of Bcl-xL is associated with decreased apoptosis in tumors, resistance to chemotherapeutic drugs, and poor clinical outcome. Given that many genes are alternatively spliced to produce proteins with opposing effects on apoptosis, perturbations that would shift alternative splicing toward the pro-apoptotic forms may help reverse the malignant phenotype of cancer cells. Thus, the ability to shift splice site selection in favor of pro-apoptotic variants could become a valuable anti-cancer strategy.

Because alternative splicing controls the production and activity of many types of proteins implicated in a variety of pathways, blocking the use of one site would enable the manipulation of protein production and protein function in a general manner. Every aspect of the life of a cell, a tissue or an organism could therefore be affected by methods that block the use of specific splice sites. Alternative splicing has been documented for kinases, transcription factors, trans-membrane protein and receptors, nucleic-acid binding proteins, metabolic enzymes, secreted proteins, extracellular matrix proteins, as well as other proteins. Accordingly, reprogramming the alternative splicing of any of these proteins has the potential to affect the function of each of these proteins.

Given the pivotal role that alternative splicing plays in the diversification of protein function, strategies capable of controlling splice site selection could have an immense impact on our ability to address the function of individual isoforms, as well as providing novel and specific tools to modify or reprogram cellular processes. Approaches that target alternative splicing could therefore provide specific ways to modulate the expression of spliced isoforms with distinct activities. In addition to treating cancer, splicing interference strategies have potential therapeutic values in a wide range of genetic diseases that are caused by point mutations affecting splice site selection. In fact, 15% of all genetic defects (e.g., thalassemia, haemophilia, retinoblastoma, cystic fibrosis, analbuminemia, Lesch-Nyhan syndrome) are caused by splice site mutations.

It is clear that there remains a need for effective methods for controlling splice site selection. Such strategies could have an immense impact on our ability to address the function of individual protein isoforms, as well as providing novel and specific tools to modify or reprogram cellular processes such as apoptosis for the treatment of human disease.

Owen et al [Nucleic Acids Res. 2011 September; 39(16): 7194-7208] teaches tandem repeats of SRSF1 binding sites together with a targeting moiety so as to recruit additional SRSF1 to the target site.

U.S. Patent Application Publication No. 20080194027 that RNA binding sites may be used as decoys.

PCT Application WO1999057265 teaches chimeric decoy RNAs useful for treating HIV.

Additional background art includes US Application No. 20140128449.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

SUMMARY OF THE INVENTION

According to an aspect of some embodiments of the present invention there is provided an isolated oligonucleotide comprising ribonucleotides, the oligonucleotide comprising a nucleic acid sequence of at least two copies of a binding site for a splicing factor, the oligonucleotide being between no more than 150 nucleotides, wherein when introduced into a cell, the oligonucleotide reduces the total splicing activity of the splicing factor in the cell.

According to an aspect of some embodiments of the present invention there is provided an isolated oligonucleotide comprising ribonucleotides, the oligonucleotide comprising a nucleic acid sequence of at least two copies of a binding site for a splicing factor, the oligonucleotide being between no more than 150 nucleotides, wherein when introduced into a cell, the oligonucleotide reduces the total splicing activity of the splicing factor in the cell.

According to an aspect of some embodiments of the present invention there is provided an isolated oligonucleotide comprising ribonucleotides, the oligonucleotide comprising a nucleic acid sequence of at least two copies of a splicing-factor binding site, the oligonucleotide being no more than 150 nucleotides, the oligonucleotide being devoid of a sequence that allows hybridization thereof to cellular RNA under physiological conditions.

According to an aspect of some embodiments of the present invention there is provided a pharmaceutical composition comprising the isolated oligonucleotide of the present invention as the active agent and a pharmaceutically acceptable carrier.

According to an aspect of some embodiments of the present invention there is provided an isolated oligonucleotide comprising ribonucleotides, the oligonucleotide comprising a nucleic acid sequence of at least one copy of a binding site for a splicing factor, the oligonucleotide being between no more than 150 nucleotides, the oligonucleotide comprising no more than five ribonucleotides which are not of the splicing-factor binding site.

According to an aspect of some embodiments of the present invention there is provided a method of treating a disease associated with aberrant splicing comprising administering to a subject in need thereof a therapeutically effective amount of at least one oligonucleotide of the present invention, thereby treating the disease.

According to some embodiments of the invention the isolated oligonucleotide is devoid of a sequence that allows hybridization thereof to cellular RNA under physiological conditions.

According to some embodiments of the invention the isolated oligonucleotide comprises no more than five ribonucleotides which are not encoding the splicing-factor binding site.

According to some embodiments of the invention the splicing factor is selected from the group consisting of SRSF1, SRSF2, SRSF6, SRSF9, SRSF10, hnRNP H2, hnRNP L, hnRNP A1/A2, hnRNP A/B, hnRNP C, TRA2, LM0212, SF3b4, TIAR-3, RBMS3, RBM4.3, RBMS8, MOD, ESRP2, A1CF, RBM46, ELAV, SF1, QKI, KHDRBS1, PCBP1, Pbbp2, hnRNPK, FXR2, FXR1, FMR1, PAPI1, RBFOX1/2, RBM24, PTBP1, FUSelement and PABPN1.

According to some embodiments of the invention the splicing factor is SRSF1 or hnRNP A1/A2.

According to some embodiments of the invention at least one of the nucleotides is chemically modified.

According to some embodiments of the invention the chemically modified ribonucleotide is selected from the group consisting of phosphorothioate 2'-O-methyl, phosphorothioate 2'-MOE, locked nucleic acid (LNA), peptide nucleic acid (PNA) and phosphorodiamidate morpholino.

According to some embodiments of the invention the nucleic acid sequence further encodes a binding site for an additional splicing factor.

According to some embodiments of the invention the at least two copies of a splicing factor binding site are contiguous.

According to some embodiments of the invention the at least two copies of a splicing factor binding site are non-contiguous.

According to some embodiments of the invention the splicing factor binding site comprises a sequence selected from the group consisting of CGCAGGA (SEQ ID NO: 1), CACAGGA (SEQ ID NO: 2), UAGGGA (SEQ ID NO: 3) and CAGCTTATGAAAG (SEQ ID NO: 4).

According to some embodiments of the invention the isolated oligonucleotide comprises a sequence selected from the group consisting of SEQ ID NO: 5, 6, 16 and 17.

According to some embodiments of the invention the isolated oligonucleotide comprises a sequence selected from the group consisting of SEQ ID NOs: 1-67.

According to some embodiments of the invention the isolated oligonucleotide comprises no more than 10 copies of the splicing-factor binding site.

According to some embodiments of the invention the isolated oligonucleotide further comprises a cell targeting moiety.

According to some embodiments of the invention the isolated oligonucleotide is for treating a disease associated with aberrant splicing.

According to some embodiments of the invention the disease is selected from the group consisting of cancer, inflammation, immunological disorders, diabetes, anti viral therapy (HIV, HSV, HBV), Inflammatory Bowel Disease (IBD), neurodegeneration, Alzheimer disease, Parkinson, Spinal muscular dystrophy (SMA), Amyotrophic lateral sclerosis (ALS), Dushan Muscular Dystrophy (DMD), Familial Dysautonomia (FD), Myotonic Dystrophy type 1 and 2 (DM1, DM2) and Cystic fibrosis (CF).

According to some embodiments of the invention the cancer is selected from the group consisting of glioblastoma, liver cancer, lung cancer, colon cancer, pancreatic cancer, melanoma and breast cancer.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE SEVERAL VIEWS OF THE DRAWINGS

The patent or application file contains at least one drawing executed in color. Copies of this patent or patent application publication with color drawing(s) will be provided by the Office upon request and payment of the necessary fee.

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings:

Figure 1B:
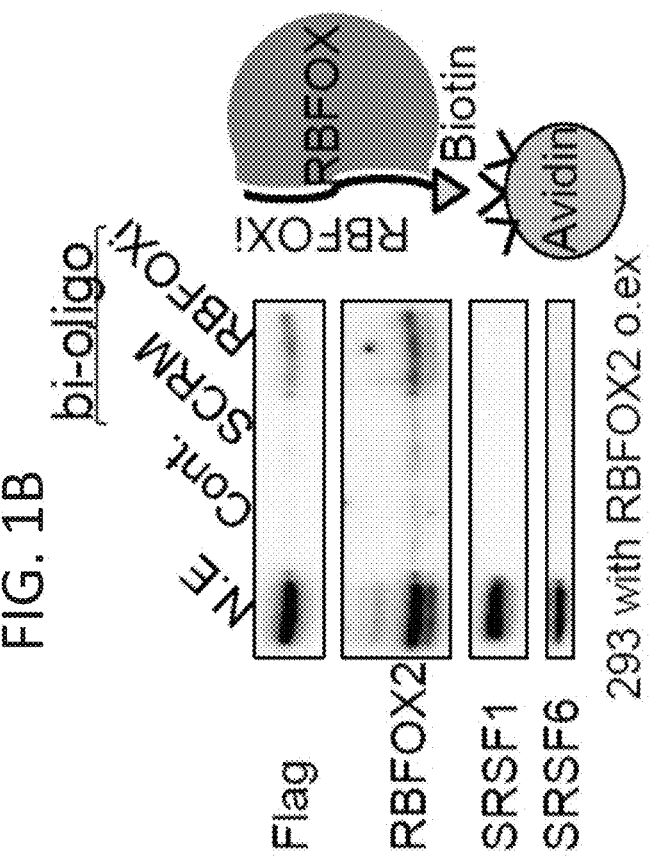
Figure 1A:
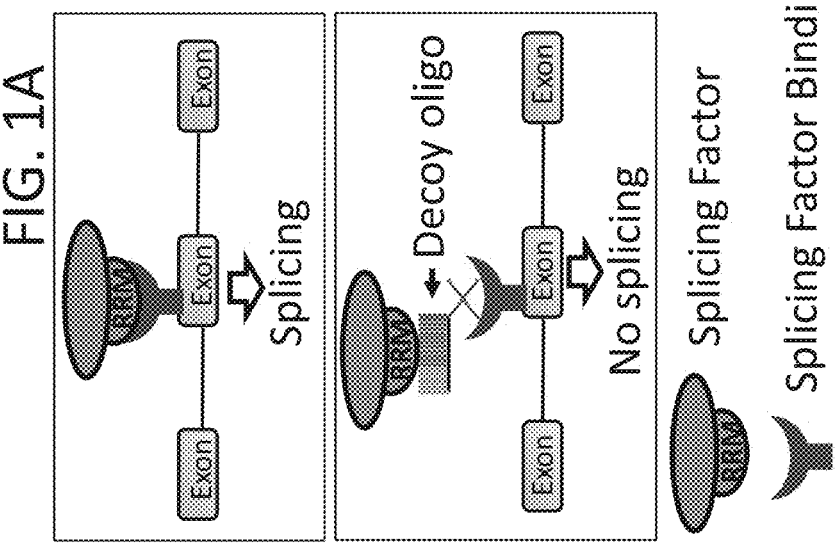
Figure 1C:
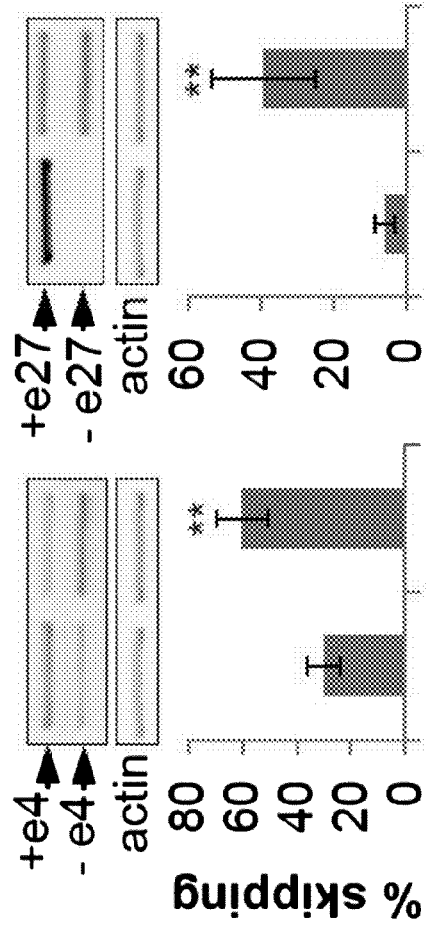
Figure 1C:
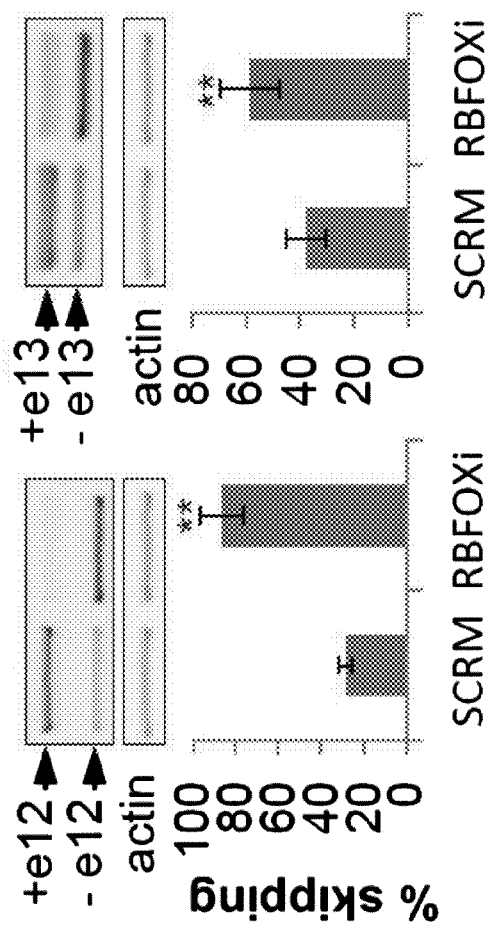
Figure 1D:
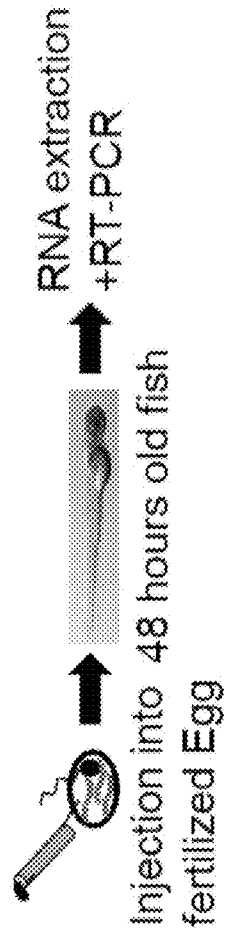

FIGS. 1A-G illustrate that RBFOX1/2 decoy oligo binds RBFOX2, causes changes in splicing of known targets in vitro, and affects alternative splicing and muscle development in zebrafish. A. Scheme representing inhibition of RNA binding proteins by decoy oligonucleotides. B. Western blot of proteins pulled down with biotin conjugated RBFOXi oligo using nuclear extracts from HEK293 cells overexpressing RBFOX2. C. RT-PCR and quantification of known RBFOX1/2 targets in U87MG cells transfected with 2.5 µM of either SCRM or RBFOXi oligos (n=6). Gel of representative experiment is shown above each column.  p-value<0.003. D. Scheme showing injection of RBFOXi oligos (or SCRM) into fertilized zebrafish eggs, 5 pg or 8 pg per egg. E. RT-PCR of known targets of RBFOX1/2 in 48 hour old larva after injection with 8 pg of either SCRM or RBFOXi oligos. RNA was extracted and reverse transcribed from each individual larva (n=10). Gel of representative larva is shown above each column.  p-value<0.003. F. Quantitation of phenotype severity 48 hour post fertilization after injection with either SCRM or RBFOXi oligos (5 pg, 8 pg). Phenotypes were assigned by visualization of fiber formation and segmental structures. G. Representative pictures of phalloidin staining of F-actin fibers in fish tails 48 hours post fertilization after injection with 8 pg of either SCRM or RBFOXi oligos. Pictures show tail of a whole embryo.

FIGS. 2A-D illustrate that SRSF1 decoy oligos affect splicing of known targets, activate the p38-MAPK stress pathway and inhibit NMD. A. RT-PCR and quantification of known targets of SRSF1 in U87MG cells transfected with either 2.5 µM SCRM, SF2i1 or SF2i2 oligos (n=6). Gel of representative transfection is shown above each column. B. Western blot analysis of proteins from cells described in (A), using the indicated antibodies (n=3). C. RT-qPCR of p38 pathway targets in cells described in (A). Values are normalized to actin and SCRM value is arbitrarily set to 1. D. RT-qPCR of NMD targets in cells described in (A). Values are normalized to RPL14 and SCRM value is arbitrarily set to 1.

* p-value≤0.05,** p-value<0.004.

FIGS. 3A-H illustrate that SRSF1 decoy oligos inhibit oncogenic properties of glioblastoma cancer cells; effect is partially abrogated after SB203580 treatment. A. Proliferation assay of U87MG cells 24 h after transfection with 2.5 µM of indicated decoy oligos, 4000 cells/well. Cell density was determined every 24 hours (until 72 h) by absorbance of methylene blue staining at 655 nm. * p-value≤0.02 for SF2i2 at 24 h, ** p-value≤0.0004 at 48 h and 72 h. B. Representative graph of colony survival assay of cells described in (A), 1000 cells/well. Survival is normalized to SCRM. T-test is based on 4 independent experiments. Representative pictures of 1000 cells seeded. C. Quantification of colony growth in soft agar assay of cells described in (A). Graphs represent quantification of 10 fields counted in duplicate (total of 20 fields). D. Scheme representing inhibition of SRSF1 with decoy oligos, activation of the p38 MAPK pathway and inhibition of the p38 MAPK pathway by SB203580. E. Quantification of soft agar colony growth assays of cells described in (A) treated with the indicated amounts of SB203580, 4 h. Relative survival is based on quantification of 10 fields counted in duplicate (total of 20 fields). F. Quantification of colony survival assay of cells described in (E) (1000 cells/well). G. Western blot analysis of cells described in (E). Quantification of SF2i2+vehicle is normalized to SCRM+vehicle, and SF2i2+20 µM SB is normalized to SCRM+20 µM SB, n=4 H. RT-qPCR of p38 pathway targets in cells described in (E). Values are normalized to actin and SCRM without vehicle is arbitrarily set at 1. * p-value=0.02,** p-value≤0.003.

FIGS. 4A-D illustrate that SRSF1 decoy oligo (SF2i2) affects tumor growth and metastasis formation of breast cancer cells. A. GFP-labeled MDA-MB-231 cells injected subcutaneously into NOD-SCID mice metastasize to the lungs. B. Tumor volume was measured in mice. On day 3 either SCRM or SF2i2 oligos were injected IP (100 mg/kg). Red arrows represent oligo injections. C. Lungs from sacrificed mice were visualized under fluorescent microscope. * p-value<0.05. D. RT-PCR of known targets of SRSF1 in livers of mice injected with either SCRM or SF2i2.

FIGS. 5A-F illustrate specific binding, visualization and splicing effects of RBFOX1/2 decoy oligos. A. U87MG cells 24 hours after transfection with Cy5 modified oligonucleotides (SCRM, SF2i1, SF2i2, RBFOXi). B. Protein levels of RBFOX2 in U87MG and MDA-MB-231 cells transfected with either 2.5 µM RBFOXi or SCRM oligos. C. RT-PCR and quantification of known RBFOX1/2 targets in MDA-MB-435S cells transfected with 2.5 µM of either SCRM or RBFOXi oligos (n=5). Gel of representative transfection is shown above each column. ** p-value<0.004. D. RT-PCR of known RBFOX1/2 targets in U87MG and MDA-MB-231 cells transfected with increasing amounts (0.5 µM, 1 µM, 2.5 µM and 5 µM) of RBOXi or SCRM oligos. E. Western blot of RBFOX2 protein levels in U87MG and MDA-MB-231 cells knocked down for RBFOX2 with shFOX2. F. RT-PCR of known RBFOX1/2 targets in RBFOX2 knocked down U87MG and MDA-MB-231 cells.

FIGS. 6A-H illustrate that SRSF1 decoy oligos bind SRSF1, affect splicing of known targets, inhibit NMD and activate the p38-MAPK pathway. A. Western blot of proteins pulled down with biotin (Bi) conjugated SF2i2 oligo in nuclear extracts from HEK-293 cells overexpressing SRSF1. B. RT-PCR and quantification of known targets of SRSF1 in MDA-MB-231 cells transfected with either SCRM or SRSF1 decoy oligos (SF2i1, SF2i2) (n=6, n=4 for MKNK2). Gel of representative transfection is shown above each column. C. RT-PCR of known targets of SRSF1 in U87MG and MDA-MB-231 cells transfected with increasing amounts (0.5 µM, 1 µM, 2.5 µM and 5 µM) of SCRM or SF2i2 oligos. D. RT-PCR of known targets of SRSF1 in U87MG cells transfected with oligos with different number of repeats of the SF2i2 motif. E. Protein levels of SRSF1 in U87MG and MDA-MB-231 cells transfected with either 2.5 µM SCRM, SF2i1 or SF2i2 oligos. F. Western blot analysis on cells described in (E), using the indicated antibodies (n=3). G. RT-qPCR of p38 pathway targets in cells described in (E). Values are normalized to actin and SCRM value is arbitrarily set to 1. H. RT-qPCR of NMD targets in cells described in (E). Values are normalized to RPL14 and SCRM value is arbitrarily set to 1. * p-value=0.02,** p-value≤0.003.

FIGS. 7A-I illustrate that SRSF1 decoy oligos inhibit the oncogenic properties of breast cancer and glioblastoma cells, effect is partially abrogated after SB203580 treatment. A. Proliferation assay of MDA-MB-231 cells 24 h after transfection with 2.5 µM of indicated decoy oligos, 4000 cells/well. Cell density was determined every 24 hours (until 72 h) by absorbance of methylene blue staining at 655 nm.  p-value≤0.000002 for SF2i1 and SF2i2 at all time points. B. Quantification of colony survival assay of cells described in (A). Cells were seeded at three different densities. Representative pictures of cells seeded 1000 cells/well. C. Soft agar colony growth assay of cells described in (A). Graphs represent quantification of 10 fields counted in duplicate (total of 20 fields). D. Quantification of colony survival (clonogenic) assay of U87MG cells transfected with 2.5 µM of SRSF1 decoy oligo or scrambled oligo in the presence or absence of SB203580. Cells were seeded at three different densities. E. Soft agar colony growth assay of U87MG cells transfected with 2.5 µM of either SCRM or SF2i2 oligos with or without SB203580 treatment. F. Quantification of colony survival assay of cells described in (E) (1000 cells). G-H. Graphs represent recue (relative to SCRM) after SF2i2 and SB203580 treatment in MDA-MB-231 cells. G. Soft agar colony growth assay. Relative rescue is based on quantification of 10 fields counted in each duplicate (total of 20 fields). H. Colony survival assay (1000 seeded cells). I. RT-qPCR of p38 pathway targets in cells described in A normalized to actin and SCRM with or without SB treatment.  p-value<0.003.

FIGS. 8A-D illustrate that transfection of oligos against SRSF1, hnRNPA1 and A2 reduced oncogenic properties of cancer cell lines. A-B Soft agar colony growth assay was performed in U87MG and MDA-MB-231 cells. Cells were seeded 24 h after transfection with the indicated oligonucleotides. Graphs represent quantification of 10 fields counted in each duplicate (total of 20 fields). ** p-value<0.01. C Representative pictures of colony assay of U87MG, HepG2 and MDA-MB-231 cells. Cells were seeded 24 h after transfection with the indicated oligonucleotides. Pictures are of 1000 seeded cells. D Quantification of colony assays of three cell lines U87MG, HepG2 and MDA-MB-231, seeded at three different densities. Cells were seeded for colony assay 24 h after transfection with the indicated oligonucleotides.

Figure 9C:
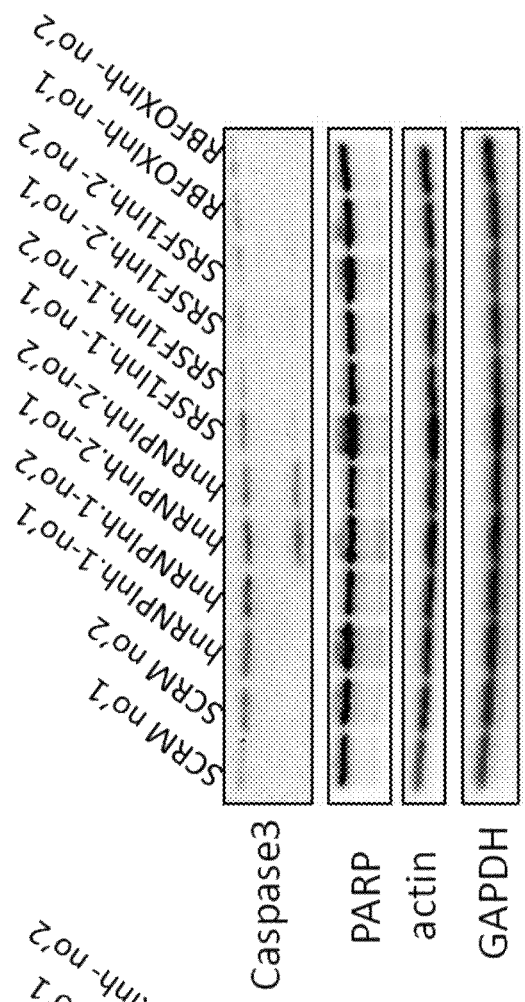
Figure 9C:
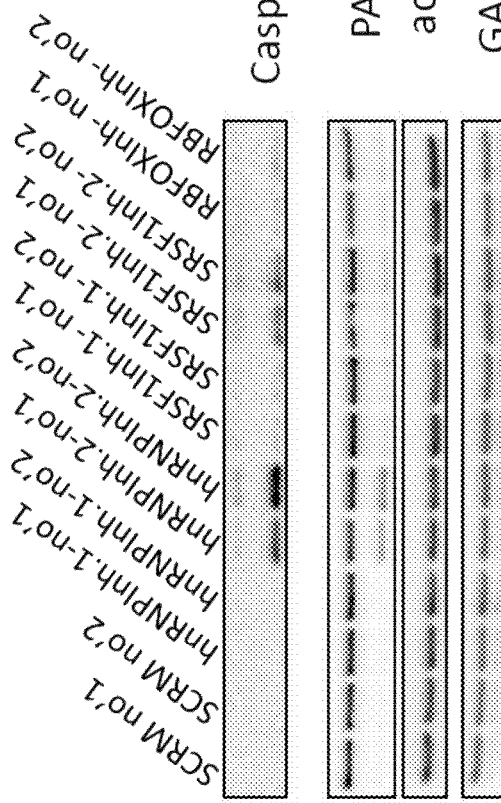

FIGS. 9A-C illustrate that the inhibition of oncogenic properties of glioblastoma and breast cells transfected with oligos against hnRNPA1 and A2 and SRSF1 is a result of reduced proliferation and increased cell death. A Proliferation assay was performed in MDA-MB-435S cells (96 hours) and U87MG cells (72 hours) transfected with the indicated oligonucleotides. 4000 cells were seeded 24 h (MDA-MB 435S) or 4 h (U87MG) after transfection. Cell number was determined every 24 hours by absorbance at 655 nm. B Percent of cell death was measured in MDA-MB-435S and U87MG cells 48 h after transfection with indicated oligonucleotides. Experiment was performed in duplicate. C Western blot on whole cell lysates from cells described in B. The membrane was probed with the indicated antibodies. Lower bands in caspase 3 and PARP represent the cleaved protein.

FIGS. 10A-D illustrate PTBP1 decoy oligos bind to PTBP1, cause changes in splicing of its known targets and inhibit transformation of breast cancer cells. A Western blot of proteins pulled down with biotin conjugated PTBP1 decoy oligo or scrambled oligo. Nuclear extract was purified from HEK293 cells. B MDA-MB-231 cells were transfected with either biotin-SCRM (bi-SCRM) or biotin-PTBP1 (bi-PTBP1) (2.5 µM or 5 µM) decoy oligos and harvested 48 h after transfection. RNA was subjected to RT-PCR using primers for the indicated splicing targets. C MDA-MB-231 cells were transfected with either biotin-SCRM (bi-SCRM) or biotin-PTBP1 (bi-PTBP1) as in (A) and 24 hours later were seeded sparsely as indicated. Surviving colonies were counted 14 days later. D MDA-MB-231 cells were transfected as in (C), and 24 hours later were seeded into soft agar. Colonies were counted 14 days later.

DESCRIPTION OF SPECIFIC EMBODIMENTS OF THE INVENTION

The present invention, in some embodiments thereof, relates to oligonucleotides which comprise sequences which encode splicing factor binding sites. When introduced into cells, such oligonucleotides reduce the total splicing activity of the splicing factor in the cell.

Before explaining at least one embodiment of the invention in detail, it is to be understood that the invention is not necessarily limited in its application to the details set forth in the following description or exemplified by the Examples. The invention is capable of other embodiments or of being practiced or carried out in various ways.

Splicing factors (SF) have been shown to play a role in many human diseases, making these factors potential therapeutic targets. However, SFs have multiple cellular functions in addition to alternative splicing, affecting other RNA processing steps. Moreover, many SFs possess RNA-independent functions such as protein-protein interactions in cellular complexes which are essential for proper cellular functions. Thus, inhibition of expression of SFs by siRNA or antisense oligonucleotides could have detrimental effects on cell fate.

The fact that some SFs are hyperactive in human diseases, and some are known to act as potent proto-oncogenes, prompted the present inventors to design and test specific inhibitors of SFs. These inhibitors were phosphothioated 2'-O-Me modified RNA oligonucleotides containing several repeats of a RNA motif (in the sense orientation), designed to be recognized specifically by a single SF.

The modified RNA oligonucleotides were tested on three alternative SFs; SRSF1, RBFOX1/2 and PTBP1. As illustrated in FIG. 1B, decoy oligos against each of these splice factors can specifically bind to the SFs and inhibit their splicing activities. Using a model system of muscle development in zebrafish the present inventors demonstrated that injection of RBFOX decoy oligos inhibit RBFOX splicing activity and interfere with muscle development in vivo, similar to what was reported using RBFOX antisense morpholinos (FIGS. 1D-G).

Introduction of SRSF1 decoy oligos into glioma and breast cancer cell lines induces splicing changes of SRSF1 targets, activation of the p38-MAPK stress pathway and inhibition of SRSF1 oncogenic properties. Moreover, injection of these oligos into mice bearing metastatic breast cancer cells results in decreased tumor volume, diminished metastasis formation in the lungs and influenced splicing of known target genes in vivo.

These results are proof of principle that modified RNA decoy oligonucleotides can serve as specific SF inhibitors and have the potential to serve as therapeutic agents for various diseases.

The decoy oligonucleotides of the present invention are advantageous over existing technologies that target the expression of genes such as siRNA or antisense oligos for numerous reasons. One of the advantages is that the decoy oligos target the RNA binding domain of the SF, inhibiting only its RNA binding activities but do not interfere with other activities such as protein-protein interactions. This is in contrast to knockdown technologies, such as siRNAs or antisense oligos, which inhibit the expression of the protein and thereby inhibit all the activities of the SF (some of which can be RNA-independent). A second advantage is that these oligonucleotides are not dependent on the half-life of the SF or on any cellular mechanism that can be mutated in certain cancer cells (unlike siRNAs) and therefore can act immediately. Finally, the decoy oligos are single stranded RNA molecules. These single stranded RNA molecules have been shown to be successfully delivered into organs of the body. In contrast, siRNAs are double stranded RNA molecules and are hard to deliver to organs in vivo. For these reasons, SF decoy oligonucleotides have a substantial advantage over traditional methods of inhibition when treating diseases known to involve high expression or activity of a specific SF.

According to one aspect of the present invention there is provided an isolated oligonucleotide comprising ribonucleotides, the oligonucleotide comprising a nucleic acid sequence of at least two copies of a binding site for a splice factor, the oligonucleotide being no more than 150 nucleotides, wherein the oligonucleotide reduces the total splicing activity of the splicing factor in the cell.

The term "splice factor" as used herein refers to an agent, typically a polypeptide that binds to RNA at a position which affects its post-transcriptional splicing.

According to a particular embodiment, the splice factor belongs to the SR protein family of splice factors which comprises a number of phylogenetically conserved and structurally related proteins with a characteristic domain rich in arginine and serine residues, known as the RS domain.

Examples of such splice factors include SRSF1-SRSF10 and also those disclosed in Long et al., Biochemical Journal Jan. 1, 2009, 417 (1) 15-27.

Particular examples of splice factors contemplated by the present invention include, but are not limited to SRSF1, SRSF2, SRSF3, SRSF4, SRSF5, SRSF6, SRSF7, SRSF8, SRSF9, SRSF10, TRA2B. TRA2A, hnRNP C, hnRNP C1, hnRNP C2, hnRNP G, hnRNP P, hnRNP A0, hnRNP A0, hnRNP A1, hnRNP A2/B1, hnRNP A3, hnRNP D, hnRNP D0, hnRNP DL, hnRNP F, hnRNP H1, hnRNP H2, hnRNP L, hnRNP LL, hnRNP M, hnRNP Q, PTBP1, PTBP2, hnRNP E1, hnRNP E2, hnRNP J, hnRNP K, hnRNP U, RBFOX1, RBFOX2, DAZAP1, PSF, TDP43, RBM4, RBM5, RBM6, CUG-BP1 (CELF1), CELF2, CELF3, CELF4, CELF5, CELF6, ESRP1, ESRP2, ETR-3, HuB, HuC, HuD, HuR, TIA1, TIAL1, QKI, Sam68, SLM-1, SLM-2, SF1, FMRP, Nova-1, Nova-2, KSRP, ZRANB2, MBNL1, YB-1, SAP155, A1CF, ANKHD1, BRUNOL5, BRUNOL6, CNOT4, CPEB2, CPEB4, DAZAP1, ENOX1, FUS, FXR1, FXR2, G3BP2, IGF2BP2, IGF2BP3, KHDRBS1, KHDRBS2, KHDRBS3, LIN28A, MATR3, MSI1, PABPC1, PABPC3, PABPC4, PABPC5, PABPN1, PCBP1, PCBP2, PCBP3, PPRC1, PUM2, RBM24, RBM28, RBM38, RBM41, RBM42, RBM45, RBM46, RBM8A, RBMS1, RBMS3, SAMD4A, SART3, SFPQ, SNRNP70, SNRPA, TUT1, U2AF1, YBX1, YBX2, ZC3H10, ZC3H14, ZCRB1 and ZNF638.

In one embodiment, the splice factor is selected from the group consisting of SRSF1 (Uniprot Q07955), SRSF2 (Uniprot Q01130), SRSF6 (Uniprot Q13247), SRSF9 (Uniprot Q13242), SRSF10 (Uniprot O75494), hnRNPL (Uniprot P14866), hnRNP A1 (Uniprot P09651), hnRNPA2 (Uniprot P22626), hnRNP A/B (Uniprot Q99729), SF3b4 (Uniprot Q15427), RBMS3 (Uniprot Q6XE24), RBM4 (Uniprot Q9BWF3), ESRP2 (Uniprot Q9H6T0), A1CF (Uniprot Q9NQ94), RBM46 (Uniprot Q8TBY0), ELAV (HuR, RBP9, EXC-7) (Uniprot P26378), SF1 (Uniprot Q15637), QKI (Uniprot Q96PU8), KHDRBS1 (Uniprot Q07666), PCBP1 (Uniprot Q15365), PCBP2 (Uniprot Q15366), hnRNPK (Uniprot P61978), FXR2 (Uniprot P51116), FXR1 (Uniprot P51114), FMR1 (Uniprot Q06787), RBFOX1/2 (Uniprot Q9NWB18), PTBP1 (Uniprot P26599), FUS (Uniprot P35637), PABPN1 (Uniprot Q86U42), U2AF1 (Uniprot Q01081) and SF3B1 (Uniprot O75533).

The binding site for the splice factor may be a spice site, a splicing enhancer element e.g. an exonic splicing enhancer (ESE) or an intronic splicing enhances (ISE), a splicing silencer elements e.g. exonic splicing silencers (ESS) or an intronic splicing silencers (ISS).

Below are the core sequences of exemplary splicing factor binding sites and additional repeat sequences contemplated by the present invention. The oligonucleotides of the present invention may comprise repeats (n) of any number of such sequences (e.g. 1, 2, 3, 4, 5, 6, 7, 8, 9, 10, 1-20, more preferably 2-20). The diseases for which the oligonucleotide may be used to treat are also included.

```
SRSF1 (SF2/ASF):
                                              (SEQ ID NO: 1)
   1. (CGCAGGA)n.

(SEQ ID NO: 5)
   2. CGCAGGACGCAGGACGCAGGA (21 bp n = 3)

(SEQ ID NO: 50)
   3. CGCAGGACGCAGGACGCAGGACGCAGGA (28 bp n = 4)

(SEQ ID NO: 2)
   4. (CACAGGA)n (SEQ ID NO: 6)
   5. CACAGGACACAGGACACAGGA (21 bp n = 3)

(SEQ ID NO: 51)
   6. CACAGGACACAGGACACAGGACACAGGA (28 bp n = 4)

(SEQ ID NO: 7)
   7. (GGAGGA)n
```

```
                                            (SEQ ID NO: 8)
8. (UGAAGGAC)n (SEQ ID NO: 9)
9. (GAAGGA)n
```

Diseases: Cancer, inflammation, immunological disorders, diabetes, anti viral therapy (HIV, HSV, HBV), Inflammatory Bowel Disease (IBD), neurodegeneration, Alzheimer disease, Parkinson, Spinal muscular dystrophy (SMA), ALS, Dushan Muscular Dystrophy (DMD), Familial Dysautonomia (FD), Myotonic Dystrophy type 1 and 2 (DM1, DM2), Cystic fibrosis (CF).

```
    SRSF2:
                                            (SEQ ID NO: 10)
1. (AGGAGA)n (SEQ ID NO: 52)
2. (UGGAGU)n

SRSF2 mutant (P95H):
                                            (SEQ ID NO: 53)
1. (UCCAGU)n
```

Diseases: Cancer, inflammation, immunological disorders.

```
    SRSF6:
                                            (SEQ ID NO: 11)
1. (GGAGGG)n
```

Diseases: Cancer, inflammation, Inflammatory Bowel Disease (IBD), immunological disorders.

```
    SRSF9:
                                            (SEQ ID NO: 12)
1. (GGAAGG)n
```

Diseases: Cancer, inflammation, immunological disorders.

```
    SRSF10 (Tra2 beta):
                                            (SEQ ID NO: 13)
1. (AGAGA)n (SEQ ID NO: 54)
2. (AGAAGA)n
```

Diseases: Cancer, inflammation, immunological disorders.

```
    hnRNP H2:
                                            (SEQ ID NO: 14)
1. (GGGAGG)n
```

Diseases: Cancer, inflammation, immunological disorders.

```
    hnRNP L:
                                            (SEQ ID NO: 15)
1. (ACACAC)n
```

Diseases: Cancer, inflammation, immunological disorders, neurodegeneration, Alzheimer disease, hypertension, kidney injury, diabetes.

```
    hnRNP A1/A2:
                                            (SEQ ID NO: 3)
1. (UAGGGA)n
```

```
                                            (SEQ ID NO: 16)
2. UAGGGAUAGGGAUAGGGAUAGGGA (24 bp n = 4)

(SEQ ID NO: 55)
3. (AGGGAU)n
```

4. (AGGGAU)n when A (adenosines) are methylated at position 6 (N6-Methyladenosine) (m6A) (SEQ ID NO: 56)

```
                                            (SEQ ID NO: 57)
5. (AGACAGAC)n
```

6. (AGACAGAC)n when A (adenosines) are methylated at position 6 (N6-Methyladenosine) (m6A) (SEQ ID NO: 58)

7. (UAGACU)n when A (adenosines) are methylated at position 6 (N6-Methyladenosine) (m6A) (SEQ ID NO: 59)

```
                                            (SEQ ID NO: 4)
8. CAGCTTATGAAAG.

(SEQ ID NO: 17)
9. CAGCTTATGAAAGCAGCTTATGAAAG (26 bp n = 2)
```

Diseases: Cancer, inflammation, immunological disorders, diabetes, anti viral therapy (HIV, HSV, HBV), Inflammatory Bowel Disease (IBD), neurodegeneration, Alzheimer disease, Parkinson, Spinal muscular dystrophy (SMA), ALS, Dushan Muscular Dystrophy (DMD), Familial Dysautonomia (FD), Myotonic Dystrophy type 1 and 2 (DM1, DM2), Cystic fibrosis (CF).

```
    hnRNP A/B:
                                            (SEQ ID NO: 18)
1. (AGAUAG)n
```

Diseases: Cancer, inflammation, immunological disorders, neurodegeneration, Alzheimer disease, Parkinson.

```
    hnRNP C:
                                            (SEQ ID NO: 19)
1. (UUUUU)n
```

Diseases: Cancer, inflammation, immunological disorders, neurodegeneration, Alzheimer disease, Parkinson, Spinal muscular dystrophy (SMA).

```
    TRA2:
                                            (SEQ ID NO: 20)
1. (AAGAA)n
```

Diseases: Cancer, inflammation, immunological disorders.

```
    LM0212:
                                            (SEQ ID NO: 21)
1. (CAUUUU)n
```

Diseases: Cancer, inflammation, immunological disorders.

```
    SF3b4:
                                            (SEQ ID NO: 22)
1. (CAAAAG)n
```

Diseases: Cancer, inflammation, immunological disorders.

TIAR-3:
1. (UUUUUU)n (SEQ ID NO: 23)

Diseases: Cancer, inflammation, immunological disorders, neurodegeneration, Alzheimer disease, Parkinson, anti viral therapy (HIV, HSV, HBV).

RBMS3:
1. (AUAUA)n (SEQ ID NO: 24)

Diseases: Cancer, inflammation, immunological disorders, neurodegeneration, Alzheimer disease, Parkinson, anti viral therapy (HIV, HSV, HBV).

RBM4.3:
1. (ACGACG)n (SEQ ID NO: 25)

Diseases: Cancer, inflammation, immunological disorders, neurodegeneration, Alzheimer disease, Parkinson, anti viral therapy (HIV, HSV, HBV).

RBMS8:
1. (GAGUAG)n (SEQ ID NO: 26)

Diseases: Cancer, inflammation, immunological disorders, neurodegeneration, Alzheimer disease, Parkinson, anti viral therapy (HIV, HSV, HBV).

MOD:
1. (UGGAA)n (SEQ ID NO: 27)

Diseases: Cancer, inflammation, immunological disorders, neurodegeneration, Alzheimer disease, Parkinson, anti viral therapy (HIV, HSV, HBV).

ESRP2:
1. (UGGGGU)n (SEQ ID NO: 28)

Diseases: Cancer, inflammation, immunological disorders, neurodegeneration, Alzheimer disease, Parkinson, anti viral therapy (HIV, HSV, HBV).

A1CF:
1. (UAAUU)n (SEQ ID NO: 29)

Diseases: Cancer, inflammation, immunological disorders, neurodegeneration, Alzheimer disease, Parkinson, anti viral therapy (HIV, HSV, HBV).

RBM46:
1. (AAUCAA)n (SEQ ID NO: 30)

ELAV, (HuR, RBP9, EXC-7):
1. (UUUGGUU)n (SEQ ID NO: 31)

Diseases: Cancer, inflammation, immunological disorders, neurodegeneration, Alzheimer disease, Parkinson, anti viral therapy (HIV, HSV, HBV).

SF1:
1. (ACUAA)n (SEQ ID NO: 32)

Diseases: Cancer, inflammation, immunological disorders, neurodegeneration, Alzheimer disease, Parkinson, anti viral therapy (HIV, HSV, HBV).

QKI:
1. (ACUAAC)n (SEQ ID NO: 33)

Diseases: Cancer, inflammation, immunological disorders, neurodegeneration, Alzheimer disease, Parkinson, anti viral therapy (HIV, HSV, HBV).

KHDRBS1:
1. (AUAAAA)n (SEQ ID NO: 34)

Diseases: Cancer, inflammation, immunological disorders, neurodegeneration, Alzheimer disease, Parkinson, anti viral therapy (HIV, HSV, HBV).

PCBP1, PCBP2:
1. (CUUUCC)n (SEQ ID NO: 35)

Diseases: Cancer, inflammation, immunological disorders, neurodegeneration, Alzheimer disease, Parkinson, anti viral therapy (HIV, HSV, HBV).

Pbbp2:
1. (UUUCCC)n (SEQ ID NO: 36)

Diseases: Cancer, inflammation, immunological disorders, neurodegeneration, Alzheimer disease, Parkinson, anti viral therapy (HIV, HSV, HBV).

hnRNPK:
1. (CCAACCC)n (SEQ ID NO: 37)

Diseases: Cancer, inflammation, immunological disorders, neurodegeneration, Alzheimer disease, Parkinson, anti viral therapy (HIV, HSV, HBV).

FXR2:
1. (GACGGG)n (SEQ ID NO: 38)

Diseases: Cancer, inflammation, immunological disorders, neurodegeneration, Alzheimer disease, Parkinson, anti viral therapy (HIV, HSV, HBV).

FXR1:
1. (AUGACA)n (SEQ ID NO: 39)

Diseases: Cancer, inflammation, immunological disorders, neurodegeneration, Alzheimer disease, Parkinson, anti viral therapy (HIV, HSV, HBV).

FMR1:
     (SEQ ID NO: 40)
  1. (GACAAG)n

Diseases: Cancer, inflammation, immunological disorders, neurodegeneration, Alzheimer disease, Parkinson, anti viral therapy (HIV, HSV, HBV).

PAPI1:
     (SEQ ID NO: 41)
  1. (GUGUGU)n

Diseases: Cancer, inflammation, immunological disorders, neurodegeneration, Alzheimer disease, Parkinson, anti viral therapy (HIV, HSV, HBV).

RBFOX1/2:
     (SEQ ID NO: 42)
  1. (UGCAUG)n
     (SEQ ID NO: 43)
  2. UGCAUGUGCAUGUGCAUGUGCAUG (24 bp n = 4) (FOX1)
     (SEQ ID NO: 44)
  3. (UGCAU)n
     (SEQ ID NO: 45)
  4. (GCAUG)n

Diseases: Cancer, inflammation, immunological disorders, diabetes, anti viral therapy (HIV, HSV, HBV), Inflammatory Bowel Disease (IBD), neurodegeneration, Alzheimer disease, Parkinson, Spinal muscular dystrophy (SFMA), ALS, Dushan Muscular Dystrophy (DMD), Familial Dysautonomia (FD), Myotonic Dystrophy type 1 and 2 (DM1, DM2), Cystic fibrosis (CF).

RBM24, RBM38:
     (SEQ ID NO: 46)
  1. (GUGUG)n

Diseases: Cancer, inflammation, immunological disorders, neurodegeneration, Alzheimer disease, Parkinson, anti viral therapy (HIV, HSV, HBV).

PTBP1:
     (SEQ ID NO: 47)
  1. (UUUUCU)n
     (SEQ ID NO: 60)
  2. (CUCUCU)n
     (SEQ ID NO: 61)
  3. CUCUCUCUCUCUCUCUCUCUCUCU
     (24 bp n = 4) (PTBP1 INHIB1X4)

Diseases: Cancer, inflammation, immunological disorders, diabetes, anti viral therapy (HIV, HSV, HBV), Inflammatory Bowel Disease (IBD), neurodegeneration, Alzheimer disease, Parkinson, Spinal muscular dystrophy (SMA), ALS, Dushan Muscular Dystrophy (DMD), Familial Dysautonomia (FD), Myotonic Dystrophy type 1 and 2 (DM1, DM2), Cystic fibrosis (CF).

FUS:
     (SEQ ID NO: 48)
  1. (CGCGC)n

Diseases: Cancer, inflammation, immunological disorders, neurodegeneration, Alzheimer disease, Parkinson, anti viral therapy (HIV, HSV, HBV).

PABPN1:
     (SEQ ID NO: 49)
  1. (AGAAGA)n

Diseases: Cancer, inflammation, immunological disorders, neurodegeneration, Alzheimer disease, Parkinson, anti viral therapy (HIV, HSV, HBV).

U2AF1 (Mutant):
     (SEQ ID NO: 62)
  1. (UUUUUUUUAG)n
     (SEQ ID NO: 63)
  2. (UUUUUUUCAG)n
     (SEQ ID NO: 64)
  3. (UUUUUUUAAG)n Diseases: Cancer, inflammation, immunological disorders, diabetes, anti viral therapy (HIV, HSV, HBV), Inflammatory Bowel Disease (IBD), neurodegeneration, Alzheimer disease, Parkinson, Spinal muscular dystrophy (SMA), ALS, Dushan Muscular Dystrophy (DMD), Familial Dysautonomia (FD), Myotonic Dystrophy type 1 and 2 (DM1, DM2), Cystic fibrosis (CF).

SF3B1 (mutant):
     (SEQ ID NO: 65)
  1. (AAAAAUUUUUUUUCAG)n
     (SEQ ID NO: 66)
  2. (UUUAAUUUUUUUUCAG)n Diseases: Cancer, inflammation, immunological disorders, diabetes, anti viral therapy (HIV, HSV, HBV), Inflammatory Bowel Disease (IBD), neurodegeneration, Alzheimer disease, Parkinson, Spinal muscular dystrophy (SMA), ALS, Dushan Muscular Dystrophy (DMD), Familial Dysautonomia (FD), Myotonic Dystrophy type 1 and 2 (DM1, DM2), Cystic fibrosis (CF).

As mentioned, the oligonucleotides may comprise more than one splicing factor binding site for a particular splicing factor. Thus, the oligonucleotides may comprise 1, 2, 3, 4, 5, 6, 7, 8, 9, 10 or more splice factor binding sites for one particular splicing factor.

In addition, or alternatively, the oligonucleotides of the present invention may comprise splicing factor binding sites for more than one splice factor. Thus for example the oligonucleotides may comprise 1, 2, 3, 4, 5, 6, 7, 8, 9, 10 or more splice factor binding sites for at least 1, 2, 3, 4, 5 different splice factors.

The multiple binding sites may be positioned in the oligonucleotides in a contiguous fashion or may be separated one from the other by "spacer" nucleotides.

The present invention contemplates oligonucleotides that are no longer than 150 nucleotides, no longer than 125 oligonucleotides, no longer than 100 nucleotides, no longer than 90 nucleotides, no longer than 80 nucleotides, no longer than 70 nucleotides, no longer than 60 nucleotides, no longer than 50 nucleotides, no longer than 40 nucleotide, no longer than 30 nucleotides or even no longer than 20 nucleotides.

In some embodiments the oligonucleotides are between 10-150 nucleotides in length, between 10-100 nucleotides in length, or between 10-50 nucleotides in length.

In some embodiments, the oligonucleotides do not comprise more than 20 ribonucleotides which are not of the splicing-factor binding site sequence, more than 15 ribonucleotides which are not of the splicing-factor binding site sequence, more than 10 ribonucleotides which are not of the splicing-factor binding site sequence, more than 9 ribonucleotides which are not of the splicing-factor binding site sequence, more than 8 ribonucleotides which are not of the splicing-factor binding site sequence, more than 7 ribonucleotides which are not of the splicing-factor binding site sequence, more than 6 ribonucleotides which are not of the splicing-factor binding site sequence, more than 5 ribonucleotides which are not of the splicing-factor binding site sequence, more than 4 ribonucleotides which are not of the splicing-factor binding site sequence, more than 3 ribonucleotides which are not of the splicing-factor binding site sequence, more than 2 ribonucleotides which are not of the splicing-factor binding site sequence, more than 1 ribonucleotide which is not of the splicing-factor binding site sequence.

It will be appreciated that if the oligonucleotides comprise ribonucleotides which are not of the splicing factor binding site sequence, those nucleotides are not positioned so as to interrupt the splicing-factor binding site sequence, rather they are positioned 3' or 5' to the core sequence or sequences (e.g. they may be part of the "spacer" oligonucleotides described herein above). In one embodiment, the additional oligonucleotides are positioned at the 5' end of the oligonucleotide. In another embodiment, the additional oligonucleotides are positioned at the 3' end of the oligonucleotide.

As used herein, the term "oligonucleotide" refers to a single stranded or double stranded oligomer or polymer of ribonucleic acid (RNA) or deoxyribonucleic acid (DNA), combinations of RNA and DNA, or mimetics thereof. This term includes oligonucleotides composed of naturally-occurring bases, sugars and covalent internucleoside linkages (e.g., backbone) as well as oligonucleotides having non-naturally-occurring portions which function similarly to respective naturally-occurring portions.

As used herein, the term "ribonucleotide" refers to a nucleotide having a hydroxy at the 2' position of the sugar portion of the nucleotide. Ribonucleotides may be modified with any of a variety of substituents.

Oligonucleotides designed according to the teachings of some embodiments of the invention can be generated according to any oligonucleotide synthesis method known in the art such as enzymatic synthesis or solid phase synthesis. Equipment and reagents for executing solid-phase synthesis are commercially available from, for example, Applied Biosystems. Any other means for such synthesis may also be employed; the actual synthesis of the oligonucleotides is well within the capabilities of one skilled in the art and can be accomplished via established methodologies as detailed in, for example, "Molecular Cloning: A laboratory Manual" Sambrook et al., (1989); "Current Protocols in Molecular Biology" Volumes I-III Ausubel, R. M., ed. (1994); Ausubel et al., "Current Protocols in Molecular Biology", John Wiley and Sons, Baltimore, Md. (1989); Perbal, "A Practical Guide to Molecular Cloning", John Wiley & Sons, New York (1988) and "Oligonucleotide Synthesis" Gait, M. J., ed. (1984) utilizing solid phase chemistry, e.g. cyanoethyl phosphoramidite followed by deprotection, desalting and purification by for example, an automated trityl-on method or HPLC.

The oligonucleotide of some embodiments of the invention is capable of inhibiting splicing activity of the splicing factor. Thus, the oligonucleotides act to sequester splicing factors such that they are no longer capable of binding to splice sites or splicing enhancer or silencer elements such as exonic splicing enhances (ESE), exonic splicing silencers (ESS), intronic splicing enhances (ISE) and intronic splicing silencers (ISS) in RNA of the cell. Thus, the overall splicing activity of a specific splicing factor is down-regulated or inhibited in the cell. Typically, the oligonucleotide is devoid of sequences (an RNA annealing domain) which allow it to hybridize to the RNA of the cell under physiological conditions (i.e. the oligonucleotide is devoid of a sequence having more than 10 or more than 15 contiguous ribonucleotides which base pair/hybridize with cellular RNA).

The oligonucleotides of some embodiments of the invention may comprise heterocylic nucleosides consisting of purines and the pyrimidines bases, bonded in a 3' to 5' phosphodiester linkage.

Preferably used oligonucleotides are those modified in either backbone, internucleoside linkages or bases, as is broadly described hereinunder.

Specific examples of preferred oligonucleotides useful according to some embodiments of the invention include oligonucleotides containing modified backbones or non-natural internucleoside linkages. Oligonucleotides having modified backbones include those that retain a phosphorus atom in the backbone, as disclosed in U.S. Pat. Nos. 4,469,863; 4,476,301; 5,023,243; 5,177,196; 5,188,897; 5,264,423; 5,276,019; 5,278,302; 5,286,717; 5,321,131; 5,399,676; 5,405,939; 5,453,496; 5,455,233; 5,466, 677; 5,476,925; 5,519,126; 5,536,821; 5,541,306; 5,550,111; 5,563,253; 5,571,799; 5,587,361; and 5,625,050.

Preferred modified oligonucleotide backbones include, for example, phosphorothioates, chiral phosphorothioates, phosphorodithioates, phosphotriesters, aminoalkyl phosphotriesters, methyl and other alkyl phosphonates including 3'-alkylene phosphonates and chiral phosphonates, phosphinates, phosphoramidates including 3'-amino phosphoramidate and aminoalkylphosphoramidates, thionophosphoramidates, thionoalkylphosphonates, thionoalkylphosphotriesters, and boranophosphates having normal 3'-5' linkages, 2'-5' linked analogs of these, and those having inverted polarity wherein the adjacent pairs of nucleoside units are linked 3'-5' to 5'-3' or 2'-5' to 5'-2'. Various salts, mixed salts and free acid forms can also be used.

Alternatively, modified oligonucleotide backbones that do not include a phosphorus atom therein have backbones that are formed by short chain alkyl or cycloalkyl internucleoside linkages, mixed heteroatom and alkyl or cycloalkyl internucleoside linkages, or one or more short chain heteroatomic or heterocyclic internucleoside linkages. These include those having morpholino linkages (formed in part from the sugar portion of a nucleoside); siloxane backbones; sulfide, sulfoxide and sulfone backbones; formacetyl and thioformacetyl backbones; methylene formacetyl and thioformacetyl backbones; alkene containing backbones; sulfamate backbones; methyleneimino and methylenehydrazino backbones; sulfonate and sulfonamide backbones; amide backbones; and others having mixed N, O, S and CH2 component parts, as disclosed in U.S. Pat. Nos. 5,034,506; 5,166,315; 5,185,444; 5,214,134; 5,216,141; 5,235,033; 5,264,562; 5,264,564; 5,405,938; 5,434,257; 5,466,677; 5,470,967; 5,489,677; 5,541,307; 5,561,225; 5,596,086; 5,602,240; 5,610,289; 5,602,240; 5,608,046; 5,610,289; 5,618,704; 5,623,070; 5,663,312; 5,633,360; 5,677,437; and 5,677,439.

Other oligonucleotides which can be used according to some embodiments of the invention, are those modified in both sugar and the internucleoside linkage, i.e., the backbone, of the nucleotide units are replaced with novel groups. The base units are maintained for complementation with the appropriate polynucleotide target. An example for such an oligonucleotide mimetic, includes peptide nucleic acid (PNA). A PNA oligonucleotide refers to an oligonucleotide where the sugar-backbone is replaced with an amide containing backbone, in particular an aminoethylglycine backbone. The bases are retained and are bound directly or indirectly to aza nitrogen atoms of the amide portion of the backbone. United States patents that teach the preparation of PNA compounds include, but are not limited to, U.S. Pat. Nos. 5,539,082; 5,714,331; and 5,719,262, each of which is herein incorporated by reference. Other backbone modifications, which can be used in some embodiments of the invention are disclosed in U.S. Pat. No. 6,303,374.

Additionally, or alternatively the oligonucleotides of the present invention may be phosphorothioated, 2-o-methyl protected and/or LNA modified.

Oligonucleotides of some embodiments of the invention may also include base modifications or substitutions. As used herein, "unmodified" or "natural" bases include the purine bases adenine (A) and guanine (G), and the pyrimidine bases thymine (T), cytosine (C) and uracil (U). Modified bases include but are not limited to other synthetic and natural bases such as 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl uracil and cytosine, 6-azo uracil, cytosine and thymine, 5-uracil (pseudouracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylguanine and 7-methyladenine, 8-azaguanine and 8-azaadenine, 7-deazaguanine and 7-deazaadenine and 3-deazaguanine and 3-deazaadenine. Further bases include those disclosed in U.S. Pat. No. 3,687,808, those disclosed in The Concise Encyclopedia Of Polymer Science And Engineering, pages 858-859, Kroschwitz, J. I., ed. John Wiley & Sons, 1990, those disclosed by Englisch et al., Angewandte Chemie, International Edition, 1991, 30, 613, and those disclosed by Sanghvi, Y. S., Chapter 15, Antisense Research and Applications, pages 289-302, Crooke, S. T. and Lebleu, B., ed., CRC Press, 1993. Such bases are particularly useful for increasing the binding affinity of the oligomeric compounds of the invention. These include 5-substituted pyrimidines, 6-azapyrimidines and N-2, N-6 and O-6 substituted purines, including 2-aminopropyladenine, 5-propynyluracil and 5-propynylcytosine. 5-methylcytosine substitutions have been shown to increase nucleic acid duplex stability by 0.6-1.2° C. [Sanghvi Y S et al. (1993) Antisense Research and Applications, CRC Press, Boca Raton 276-278] and are presently preferred base substitutions, even more particularly when combined with 2'-O-methoxyethyl sugar modifications.

Since the oligonucleotides must enter the cell in order to have activity, it is conceived that they are attached to a cell penetrating moiety. Alternatively, or additionally the oligonucleotides are chemically modified so as to enhance cell and/or nuclear penetration.

As mentioned the oligonucleotides described herein may be used to treat a myriad of disease which are associated with aberrant cell splicing. In one embodiment, the disease is cancer, as further described herein below.

Cancer

Examples of cancers that may be treated using the agents described herein include, but are not limited to adrenocortical carcinoma, hereditary; bladder cancer; breast cancer; breast cancer, ductal; breast cancer, invasive intraductal; breast cancer, sporadic; breast cancer, susceptibility to; breast cancer, type 4; breast cancer, type 4; breast cancer-1; breast cancer-3; breast-ovarian cancer; triple negative breast cancer, Burkitt's lymphoma; cervical carcinoma; colorectal adenoma; colorectal cancer; colorectal cancer, hereditary nonpolyposis, type 1; colorectal cancer, hereditary nonpolyposis, type 2; colorectal cancer, hereditary nonpolyposis, type 3; colorectal cancer, hereditary nonpolyposis, type 6; colorectal cancer, hereditary nonpolyposis, type 7; dermatofibrosarcoma protuberans; endometrial carcinoma; esophageal cancer; gastric cancer, fibrosarcoma, glioblastoma multiforme; glomus tumors, multiple; hepatoblastoma; hepatocellular cancer; hepatocellular carcinoma; leukemia, acute lymphoblastic; leukemia, acute myeloid; leukemia, acute myeloid, with eosinophilia; leukemia, acute nonlymphocytic; leukemia, chronic myeloid; Li-Fraumeni syndrome; liposarcoma, lung cancer; lung cancer, small cell; lymphoma, non-Hodgkin's; lynch cancer family syndrome II; male germ cell tumor; mast cell leukemia; medullary thyroid; medulloblastoma; melanoma, malignant melanoma, meningioma; multiple endocrine neoplasia; multiple myeloma, myeloid malignancy, predisposition to; myxosarcoma, neuroblastoma; osteosarcoma; osteocarcinoma, ovarian cancer; ovarian cancer, serous; ovarian carcinoma; ovarian sex cord tumors; pancreatic cancer; pancreatic endocrine tumors; paraganglioma, familial nonchromaffin; pilomatricoma; pituitary tumor, invasive; prostate adenocarcinoma; prostate cancer; renal cell carcinoma, papillary, familial and sporadic; retinoblastoma; rhabdoid predisposition syndrome, familial; rhabdoid tumors; rhabdomyosarcoma; small-cell cancer of lung; soft tissue sarcoma, squamous cell carcinoma, basal cell carcinoma, head and neck; T-cell acute lymphoblastic leukemia; Turcot syndrome with glioblastoma; tylosis with esophageal cancer; uterine cervix carcinoma, Wilms' tumor, type 2; and Wilms' tumor, type 1, and the like.

Neurodegenerative Diseases—

The term "neurodegenerative disease" is used herein to describe a disease which is caused by damage to the central nervous system. Exemplary neurodegenerative diseases which may be treated using the cells and methods according to the present invention include for example, Parkinson's disease, Huntington's disease, amyotrophic lateral sclerosis (ALS), Alzheimer's disease, Rett Syndrome, lysosomal storage diseases ("white matter disease" or glial/demyelination disease, as described, for example by Folkerth, J. Neuropath. Exp. Neuro., September 1999, 58:9), including Sanfilippo, Gaucher disease, Tay Sachs disease (beta hexosaminidase deficiency), other genetic diseases, multiple sclerosis, brain injury or trauma caused by ischemia, accidents, environmental insult, etc., spinal cord damage, ataxia and alcoholism. In addition, the present invention may be used to reduce and/or eliminate the effects on the central nervous system of a stroke or a heart attack in a patient, which is otherwise caused by lack of blood flow or ischemia to a site in the brain of the patient or which has occurred from physical injury to the brain and/or spinal cord. Neurodegenerative diseases also include neurodevelopmental disorders including for example, autism and related neurological diseases such as schizophrenia, among numerous others.

In another embodiment, the disease is an inflammatory disease.

Inflammatory Diseases—

Include, but are not limited to, chronic inflammatory diseases and acute inflammatory diseases.

Inflammatory Diseases Associated with Hypersensitivity

Examples of hypersensitivity include, but are not limited to, Type I hypersensitivity, Type II hypersensitivity, Type III hypersensitivity, Type IV hypersensitivity, immediate hypersensitivity, antibody mediated hypersensitivity, immune complex mediated hypersensitivity, T lymphocyte mediated hypersensitivity and DTH.

Type I or immediate hypersensitivity, such as asthma.

Type II hypersensitivity include, but are not limited to, rheumatoid diseases, rheumatoid autoimmune diseases, rheumatoid arthritis (Krenn V. et al., Histol Histopathol 2000 July; 15 (3):791), spondylitis, ankylosing spondylitis (Jan Voswinkel et al., Arthritis Res 2001; 3 (3): 189), systemic diseases, systemic autoimmune diseases, systemic lupus erythematosus (Erikson J. et al., Immunol Res 1998; 17 (1-2):49), sclerosis, systemic sclerosis (Renaudineau Y. et al., Clin Diagn Lab Immunol. 1999 March; 6 (2):156); Chan O T. et al., Immunol Rev 1999 June; 169:107), glandular diseases, glandular autoimmune diseases, pancreatic autoimmune diseases, diabetes, Type I diabetes (Zimmet P. Diabetes Res Clin Pract 1996 October; 34 Suppl:S125), thyroid diseases, autoimmune thyroid diseases, Graves' disease (Orgiazzi J. Endocrinol Metab Clin North Am 2000 June; 29 (2):339), thyroiditis, spontaneous autoimmune thyroiditis (Braley-Mullen H. and Yu S, J Immunol 2000 Dec. 15; 165 (12):7262), Hashimoto's thyroiditis (Toyoda N. et al., Nippon Rinsho 1999 August; 57 (8):1810), myxedema, idiopathic myxedema (Mitsuma T. Nippon Rinsho. 1999 August; 57 (8):1759); autoimmune reproductive diseases, ovarian diseases, ovarian autoimmunity (Garza K M. et al., J Reprod Immunol 1998 February; 37 (2):87), autoimmune anti-sperm infertility (Diekman A B. et al., Am J Reprod Immunol. 2000 March; 43 (3):134), repeated fetal loss (Tincani A. et al., Lupus 1998; 7 Suppl 2:S107-9), neurodegenerative diseases, neurological diseases, neurological autoimmune diseases, multiple sclerosis (Cross A H. et al., J Neuroimmunol 2001 Jan. 1; 112 (1-2):1), Alzheimer's disease (Oron L. et al., J Neural Transm Suppl. 1997; 49;77), myasthenia gravis (Infante A J. And Kraig E, Int Rev Immunol 1999; 18 (1-2):83), motor neuropathies (Kornberg A J. J Clin Neurosci. 2000 May; 7 (3):191), Guillain-Barre syndrome, neuropathies and autoimmune neuropathies (Kusunoki S. Am J Med Sci. 2000 April; 319 (4):234), myasthenic diseases, Lambert-Eaton myasthenic syndrome (Takamori M. Am J Med Sci. 2000 April; 319 (4):204), paraneoplastic neurological diseases, cerebellar atrophy, paraneoplastic cerebellar atrophy, non-paraneoplastic stiff man syndrome, cerebellar atrophies, progressive cerebellar atrophies, encephalitis, Rasmussen's encephalitis, amyotrophic lateral sclerosis, Sydeham chorea, Gilles de la Tourette syndrome, polyendocrinopathies, autoimmune polyendocrinopathies (Antoine J C. and Honnorat J. Rev Neurol (Paris) 2000 January; 156 (1):23); neuropathies, dysimmune neuropathies (Nobile-Orazio E. et al., Electroencephalogr Clin Neurophysiol Suppl 1999; 50:419); neuromyotonia, acquired neuromyotonia, arthrogryposis multiplex congenita (Vincent A. et al., Ann N Y Acad Sci. 1998 May 13; 841:482), cardiovascular diseases, cardiovascular autoimmune diseases, atherosclerosis (Matsuura E. et al., Lupus. 1998; 7 Suppl 2:S135), myocardial infarction (Vaarala O. Lupus. 1998; 7 Suppl 2:S132), thrombosis (Tincani A. et al., Lupus 1998; 7 Suppl 2:S107-9), granulomatosis, Wegener's granulomatosis, arteritis, Takayasu's arteritis and Kawasaki syndrome (Praprotnik S. et al., Wien Klin Wochenschr 2000 Aug. 25; 112 (15-16):660); antifactor VIII autoimmune disease (Lacroix-Desmazes S. et al., Semin Thromb Hemost.2000; 26 (2):157); vasculitises, necrotizing small vessel vasculitises, microscopic polyangiitis, Churg and Strauss syndrome, glomerulonephritis, pauciimmune focal necrotizing glomerulonephritis, crescentic glomerulonephritis (Noel L H. Ann Med Interne (Paris). 2000 May; 151 (3):178); antiphospholipid syndrome (Flamholz R. et al., J Clin Apheresis 1999; 14 (4):171); heart failure, agonist-like beta-adrenoceptor antibodies in heart failure (Wallukat G. et al., Am J Cardiol. 1999 Jun. 17; 83 (12A):75H), thrombocytopenic purpura (Moccia F. Ann Ital Med Int. 1999 April-June; 14 (2):114); hemolytic anemia, autoimmune hemolytic anemia (Efremov D G. et al., Leuk Lymphoma 1998 January; 28 (3-4):285), gastrointestinal diseases, autoimmune diseases of the gastrointestinal tract, intestinal diseases, chronic inflammatory intestinal disease (Garcia Herola A. et al., Gastroenterol Hepatol. 2000 January; 23 (1):16), celiac disease (Landau Y E. and Shoenfeld Y. Harefuah 2000 Jan. 16; 138 (2):122), autoimmune diseases of the musculature, myositis, autoimmune myositis, Sjogren's syndrome (Feist E. et al., Int Arch Allergy Immunol 2000 September; 123 (1):92); smooth muscle autoimmune disease (Zauli D. et al., Biomed Pharmacother 1999 June; 53 (5-6):234), hepatic diseases, hepatic autoimmune diseases, autoimmune hepatitis (Manns M P. J Hepatol 2000 August; 33 (2):326) and primary biliary cirrhosis (Strassburg C P. et al., Eur J Gastroenterol Hepatol. 1999 June; 11 (6):595).

Type IV or T cell mediated hypersensitivity, include, but are not limited to, rheumatoid diseases, rheumatoid arthritis (Tisch R, McDevitt H O. Proc Natl Acad Sci USA 1994 Jan. 18; 91 (2):437), systemic diseases, systemic autoimmune diseases, systemic lupus erythematosus (Datta S K., Lupus 1998; 7 (9):591), glandular diseases, glandular autoimmune diseases, pancreatic diseases, pancreatic autoimmune diseases, Type 1 diabetes (Castano L. and Eisenbarth G S. Ann. Rev. Immunol. 8:647); thyroid diseases, autoimmune thyroid diseases, Graves' disease (Sakata S. et al., Mol Cell Endocrinol 1993 March; 92 (1):77); ovarian diseases (Garza K M. et al., J Reprod Immunol 1998 February; 37 (2):87), prostatitis, autoimmune prostatitis (Alexander R B. et al., Urology 1997 December; 50 (6):893), polyglandular syndrome, autoimmune polyglandular syndrome, Type I autoimmune polyglandular syndrome (Hara T. et al., Blood. 1991 Mar. 1; 77 (5):1127), neurological diseases, autoimmune neurological diseases, multiple sclerosis, neuritis, optic neuritis (Soderstrom M. et al., J Neurol Neurosurg Psychiatry 1994 May; 57 (5):544), myasthenia gravis (Oshima M. et al., Eur J Immunol 1990 December; 20 (12): 2563), stiff-man syndrome (Hiemstra H S. et al., Proc Natl Acad Sci USA 2001 Mar. 27; 98 (7):3988), cardiovascular diseases, cardiac autoimmunity in Chagas' disease (Cunha-Neto E. et al., J Clin Invest 1996 Oct. 15; 98 (8):1709), autoimmune thrombocytopenic purpura (Semple J W. et al., Blood 1996 May 15; 87 (10):4245), anti-helper T lymphocyte autoimmunity (Caporossi A P. et al., Viral Immunol 1998; 11 (1):9), hemolytic anemia (Sallah S. et al., Ann Hematol 1997 March; 74 (3):139), hepatic diseases, hepatic autoimmune diseases, hepatitis, chronic active hepatitis (Franco A. et al., Clin Immunol Immunopathol 1990 March; 54 (3):382), biliary cirrhosis, primary biliary cirrhosis (Jones D E. Clin Sci (Colch) 1996 November; 91 (5):551), nephric diseases, nephric autoimmune diseases, nephritis, interstitial nephritis (Kelly C J. J Am Soc Nephrol 1990 August; 1 (2):140), connective tissue diseases, ear diseases, autoimmune connective tissue diseases, autoimmune ear disease (Yoo T J. et al., Cell Immunol 1994 August; 157 (1):249), disease of the inner ear (Gloddek B. et al., Ann N Y Acad Sci 1997 Dec. 29; 830:266), skin diseases, cutaneous diseases, dermal diseases, bullous skin diseases, pemphigus vulgaris, bullous pemphigoid and pemphigus foliaceus.

Examples of delayed type hypersensitivity include, but are not limited to, contact dermatitis and drug eruption.

Examples of types of T lymphocyte mediating hypersensitivity include, but are not limited to, helper T lymphocytes and cytotoxic T lymphocytes.

Examples of helper T lymphocyte-mediated hypersensitivity include, but are not limited to, $T_h1$ lymphocyte mediated hypersensitivity and $T_h2$ lymphocyte mediated hypersensitivity.

Autoimmune Diseases

Include, but are not limited to, cardiovascular diseases, rheumatoid diseases, glandular diseases, gastrointestinal diseases, cutaneous diseases, hepatic diseases, neurological diseases, muscular diseases, nephric diseases, diseases related to reproduction, connective tissue diseases and systemic diseases.

Examples of autoimmune cardiovascular diseases include, but are not limited to atherosclerosis (Matsuura E. et al., Lupus. 1998; 7 Suppl 2:S135), myocardial infarction (Vaarala O. Lupus. 1998; 7 Suppl 2:S132), thrombosis (Tincani A. et al., Lupus 1998; 7 Suppl 2:S107-9), Wegener's granulomatosis, Takayasu's arteritis, Kawasaki syndrome (Praprotnik S. et al., Wien Klin Wochenschr 2000 Aug. 25; 112 (15-16):660), anti-factor VIII autoimmune disease (Lacroix-Desmazes S. et al., Semin Thromb Hemost.2000; 26 (2):157), necrotizing small vessel vasculitis, microscopic polyangiitis, Churg and Strauss syndrome, pauci-immune focal necrotizing and crescentic glomerulonephritis (Noel L H. Ann Med Interne (Paris). 2000 May; 151 (3):178), antiphospholipid syndrome (Flamholz R. et al., J Clin Apheresis 1999; 14 (4):171), antibody-induced heart failure (Wallukat G. et al., Am J Cardiol. 1999 Jun. 17; 83 (12A):75H), thrombocytopenic purpura (Moccia F. Ann Ital Med Int. 1999 April-June; 14 (2):114; Semple J W. et al., Blood 1996 May 15; 87 (10):4245), autoimmune hemolytic anemia (Efremov D G. et al., Leuk Lymphoma 1998 January; 28 (3-4):285; Sallah S. et al., Ann Hematol 1997 March; 74 (3):139), cardiac autoimmunity in Chagas' disease (Cunha-Neto E. et al., J Clin Invest 1996 Oct. 15; 98 (8):1709) and anti-helper T lymphocyte autoimmunity (Caporossi A P. et al., Viral Immunol 1998; 11 (1):9).

Examples of autoimmune rheumatoid diseases include, but are not limited to rheumatoid arthritis (Krenn V. et al., Histol Histopathol 2000 July; 15 (3):791; Tisch R, McDevitt H O. Proc Natl Acad Sci units S A 1994 Jan. 18; 91 (2):437) and ankylosing spondylitis (Jan Voswinkel et al., Arthritis Res 2001; 3 (3): 189).

Examples of autoimmune glandular diseases include, but are not limited to, pancreatic disease, Type I diabetes, thyroid disease, Graves' disease, thyroiditis, spontaneous autoimmune thyroiditis, Hashimoto's thyroiditis, idiopathic myxedema, ovarian autoimmunity, autoimmune anti-sperm infertility, autoimmune prostatitis and Type I autoimmune polyglandular syndrome. Diseases include, but are not limited to autoimmune diseases of the pancreas, Type 1 diabetes (Castano L. and Eisenbarth G S. Ann. Rev. Immunol. 8:647; Zimmet P. Diabetes Res Clin Pract 1996 October; 34 Suppl: S125), autoimmune thyroid diseases, Graves' disease (Orgiazzi J. Endocrinol Metab Clin North Am 2000 June; 29 (2):339; Sakata S. et al., Mol Cell Endocrinol 1993 March; 92 (1):77), spontaneous autoimmune thyroiditis (Braley-Mullen H. and Yu S, J Immunol 2000 Dec. 15; 165 (12): 7262), Hashimoto's thyroiditis (Toyoda N. et al., Nippon Rinsho 1999 August; 57 (8):1810), idiopathic myxedema (Mitsuma T. Nippon Rinsho. 1999 August; 57 (8):1759), ovarian autoimmunity (Garza K M. et al., J Reprod Immunol 1998 February; 37 (2):87), autoimmune anti-sperm infertility (Diekman A B. et al., Am J Reprod Immunol. 2000 March; 43 (3):134), autoimmune prostatitis (Alexander R B. et al., Urology 1997 December; 50 (6):893) and Type I autoimmune polyglandular syndrome (Hara T. et al., Blood. 1991 Mar. 1; 77 (5):1127).

Examples of autoimmune gastrointestinal diseases include, but are not limited to, chronic inflammatory intestinal diseases (Garcia Herola A. et al., Gastroenterol Hepatol. 2000 January; 23 (1):16), celiac disease (Landau Y E. and Shoenfeld Y. Harefuah 2000 Jan. 16; 138 (2):122), colitis, ileitis and Crohn's disease.

Examples of autoimmune cutaneous diseases include, but are not limited to, autoimmune bullous skin diseases, such as, but are not limited to, pemphigus vulgaris, bullous pemphigoid and pemphigus foliaceus.

Examples of autoimmune hepatic diseases include, but are not limited to, hepatitis, autoimmune chronic active hepatitis (Franco A. et al., Clin Immunol Immunopathol 1990 March; 54 (3):382), primary biliary cirrhosis (Jones D E. Clin Sci (Colch) 1996 November; 91 (5):551; Strassburg C P. et al., Eur J Gastroenterol Hepatol. 1999 June; 11 (6):595) and autoimmune hepatitis (Manns M P. J Hepatol 2000 August; 33 (2):326).

Examples of autoimmune neurological diseases include, but are not limited to, multiple sclerosis (Cross A H. et al., J Neuroimmunol 2001 Jan. 1; 112 (1-2):1), Alzheimer's disease (Oron L. et al., J Neural Transm Suppl. 1997; 49:77), myasthenia gravis (Infante A J. And Kraig E, Int Rev Immunol 1999; 18 (1-2):83; Oshima M. et al., Eur J Immunol 1990 December; 20 (12):2563), neuropathies, motor neuropathies (Kornberg A J. J Clin Neurosci. 2000 May; 7 (3):191); Guillain-Barre syndrome and autoimmune neuropathies (Kusunoki S. Am J Med Sci. 2000 April; 319 (4):234), myasthenia, Lambert-Eaton myasthenic syndrome (Takamori M. Am J Med Sci. 2000 April; 319 (4):204); paraneoplastic neurological diseases, cerebellar atrophy, paraneoplastic cerebellar atrophy and stiff-man syndrome (Hiemstra H S. et al., Proc Natl Acad Sci units S A 2001 Mar. 27; 98 (7):3988); non-paraneoplastic stiff man syndrome, progressive cerebellar atrophies, encephalitis, Rasmussen's encephalitis, amyotrophic lateral sclerosis, Sydeham chorea, Gilles de la Tourette syndrome and autoimmune polyendocrinopathies (Antoine J C. and Honnorat J. Rev Neurol (Paris) 2000 January; 156 (1):23); dysimmune neuropathies (Nobile-Orazio E. et al., Electroencephalogr Clin Neurophysiol Suppl 1999; 50:419); acquired neuromyotonia, arthrogryposis multiplex congenita (Vincent A. et al., Ann N Y Acad Sci. 1998 May 13; 841:482), neuritis, optic neuritis (Soderstrom M. et al., J Neurol Neurosurg Psychiatry 1994 May; 57 (5):544) and neurodegenerative diseases.

Examples of autoimmune muscular diseases include, but are not limited to, myositis, autoimmune myositis and primary Sjogren's syndrome (Feist E. et al., Int Arch Allergy Immunol 2000 September; 123 (1):92) and smooth muscle autoimmune disease (Zauli D. et al., Biomed Pharmacother 1999 June; 53 (5-6):234).

Examples of autoimmune nephric diseases include, but are not limited to, nephritis and autoimmune interstitial nephritis (Kelly C J. J Am Soc Nephrol 1990 August; 1 (2): 140).

Examples of autoimmune diseases related to reproduction include, but are not limited to, repeated fetal loss (Tincani A. et al., Lupus 1998; 7 Suppl 2:S107-9).

Examples of autoimmune connective tissue diseases include, but are not limited to, ear diseases, autoimmune ear diseases (Yoo T J. et al., Cell Immunol 1994 August; 157 (1):249) and autoimmune diseases of the inner ear (Gloddek B. et al., Ann N Y Acad Sci 1997 Dec. 29; 830:266).

Examples of autoimmune systemic diseases include, but are not limited to, systemic lupus erythematosus (Erikson J. et al., Immunol Res 1998; 17 (1-2):49) and systemic sclerosis (Renaudineau Y. et al., Clin Diagn Lab Immunol. 1999 March; 6 (2):156); Chan O T. et al., Immunol Rev 1999 June; 169:107).

Infectious Diseases

Examples of infectious diseases include, but are not limited to, chronic infectious diseases, subacute infectious diseases, acute infectious diseases, viral diseases, bacterial diseases, protozoan diseases, parasitic diseases, fungal diseases, mycoplasma diseases and prion diseases.

Graft Rejection Diseases

Examples of diseases associated with transplantation of a graft include, but are not limited to, graft rejection, chronic graft rejection, subacute graft rejection, hyperacute graft rejection, acute graft rejection and graft versus host disease.

Allergic Diseases

Examples of allergic diseases include, but are not limited to, asthma, hives, urticaria, pollen allergy, dust mite allergy, venom allergy, cosmetics allergy, latex allergy, chemical allergy, drug allergy, insect bite allergy, animal dander allergy, stinging plant allergy, poison ivy allergy and food allergy.

Delivery

Methods for the delivery of nucleic acid molecules are described in Akhtar et al., (Trends Cell Bio., 2, 139, 1992). WO 94/02595 describes general methods for delivery of enzymatic RNA molecules. These protocols can be utilized for the delivery of virtually any nucleic acid molecule. The oligonucleotides can be administered to cells by a variety of methods known to those familiar to the art, including, but not restricted to, encapsulation in liposomes, by iontophoresis, or by incorporation into other vehicles, such as hydrogels, cyclodextrins, biodegradable nanocapsules, and bioadhesive microspheres. Alternatively, the nucleic acid/vehicle combination is locally delivered by direct injection or by use of an infusion pump. Other routes of delivery include, but are not limited to oral (tablet or pill form) and/or intrathecal delivery (Gold, 1997, Neuroscience, 76, 1153-1158). Other approaches include the use of various transport and carrier systems, for example, through the use of conjugates and biodegradable polymers. More detailed descriptions of nucleic acid delivery and administration are provided for example in WO 93/23569, WO 99/05094, and WO 99/04819.

The oligonucleotides can be introduced into tissues or host cells by any number of routes, including viral infection, microinjection, or fusion of vesicles. Jet injection may also be used for intramuscular administration, as described by Furth et al. (Anal. Biochem., 115 205:365-368, 1992). The oligonucleotides can be coated onto gold microparticles, and delivered intradermally by a particle bombardment device, or "gene gun" as described in the literature (see, for example, Tang et al. Nature 356:152-154, 1992), where gold microprojectiles are coated with the DNA, then bombarded into skin cells.

The oligonucleotides can be directly introduced into the cell (i.e., intracellularly); or introduced extracellularly into a cavity, interstitial space, into the circulation of an organism, introduced orally, etc. Methods for oral introduction include direct mixing of RNA with the food of the organism. Physical methods of introducing nucleic acids include injection directly into the cell or extracellular injection into the organism of an RNA solution. The agent can be introduced in an amount which allows delivery of at least one functional copy per cell. Higher doses (e.g., at least 5, 10, 100, 500 or 1000 or more copies per cell) of the agent may yield more effective inhibition; lower doses may also be useful for specific applications.

Examples of particular transfection agents contemplated by the present invention includes the lipid-based reagent siPORT™ NeoFX™ Transfection Agent (Ambion Cat. # AM4510), the polyamine-based reagent siPORT™ Amine Transfection Agent (Ambion Cat. # AM4502), the cationic and neutral lipid-based reagent siPORT™ Lipid Transfection Agent (Ambion Cat. # AM4504), the cationic lipid-based transfection reagent TransIT® TKO (Minis Corporation, Madison, Wis.), Lipofectin® Lipofectamine, Oligofectamine™ (Invitrogen, Carlsbad, Calif.), or Dharmafect™ (Dharmacon, Lafayette, Colo.), further polycations such as polyethyleneimine, cationic peptides such as Tat, polyarginine, or penetratin, or liposomes. Liposomes are formed from standard vesicle-forming lipids and a sterol, such as cholesterol, and may include a targeting molecule such as an antibody or an aptamer having binding affinity for a cell surface antigen, for example. Further, the liposomes may be PEGylated liposomes.

The oligonucleotides described herein can be administered to the subject per se (in the presence or absence of a transfection agent) or as part of a pharmaceutical composition which also includes a physiologically acceptable carrier. The purpose of a pharmaceutical composition is to facilitate administration of the active ingredient to an organism.

Herein the term "active ingredient" refers to the oligonucleotides described herein, which are accountable for the biological effect.

Hereinafter, the phrases "physiologically acceptable carrier" and "pharmaceutically acceptable carrier" which may be interchangeably used refer to a carrier or a diluent that does not cause significant irritation to an organism and does not abrogate the biological activity and properties of the administered compound. An adjuvant is included under these phrases. One of the ingredients included in the pharmaceutically acceptable carrier can be for example polyethylene glycol (PEG), a biocompatible polymer with a wide range of solubility in both organic and aqueous media (Mutter et al. (1979).

Herein the term "excipient" refers to an inert substance added to a pharmaceutical composition to further facilitate administration of an active ingredient. Examples, without limitation, of excipients include calcium carbonate, calcium phosphate, various sugars and types of starch, cellulose derivatives, gelatin, vegetable oils and polyethylene glycols.

Techniques for formulation and administration of drugs may be found in "Remington's Pharmaceutical Sciences", Mack Publishing Co., Easton, Pa., latest edition, which is incorporated herein by reference.

Suitable routes of administration may, for example, include oral, rectal, transmucosal, transnasal, intestinal or parenteral delivery, including intramuscular, subcutaneous and intramedullary injections as well as intrathecal, direct intraventricular, intravenous, intraperitoneal, intranasal, or intraocular injections.

Alternately, one may administer the preparation in a local rather than systemic manner, for example, via injection of the preparation directly into a specific region of a patient's body.

Pharmaceutical compositions of the present invention may be manufactured by processes well known in the art, e.g., by means of conventional mixing, dissolving, granulating, dragee-making, levigating, emulsifying, encapsulating, entrapping or lyophilizing processes.

Pharmaceutical compositions for use in accordance with the present invention may be formulated in conventional manner using one or more physiologically acceptable carriers comprising excipients and auxiliaries, which facilitate processing of the active ingredients into preparations which, can be used pharmaceutically. Proper formulation is dependent upon the route of administration chosen.

For injection, the active ingredients of the invention may be formulated in aqueous solutions, preferably in physiologically compatible buffers such as Hank's solution, Ringer's solution, or physiological salt buffer. For transmucosal administration, penetrants appropriate to the barrier to be permeated are used in the formulation. Such penetrants are generally known in the art.

For oral administration, the compounds can be formulated readily by combining the active compounds with pharmaceutically acceptable carriers well known in the art. Such carriers enable the compounds of the invention to be formulated as tablets, pills, dragees, capsules, liquids, gels, syrups, slurries, suspensions, and the like, for oral ingestion by a patient. Pharmacological preparations for oral use can be made using a solid excipient, optionally grinding the resulting mixture, and processing the mixture of granules, after adding suitable auxiliaries if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carbomethylcellulose; and/or physiologically acceptable polymers such as polyvinylpyrrolidone (PVP). If desired, disintegrating agents may be added, such as cross-linked polyvinyl pyrrolidone, agar, or alginic acid or a salt thereof such as sodium alginate.

Dragee cores are provided with suitable coatings. For this purpose, concentrated sugar solutions may be used which may optionally contain gum arabic, talc, polyvinyl pyrrolidone, carbopol gel, polyethylene glycol, titanium dioxide, lacquer solutions and suitable organic solvents or solvent mixtures. Dyestuffs or pigments may be added to the tablets or dragee coatings for identification or to characterize different combinations of active compound doses.

Pharmaceutical compositions, which can be used orally, include push-fit capsules made of gelatin as well as soft, sealed capsules made of gelatin and a plasticizer, such as glycerol or sorbitol. The push-fit capsules may contain the active ingredients in admixture with filler such as lactose, binders such as starches, lubricants such as talc or magnesium stearate and, optionally, stabilizers. In soft capsules, the active ingredients may be dissolved or suspended in suitable liquids, such as fatty oils, liquid paraffin, or liquid polyethylene glycols. In addition, stabilizers may be added. All formulations for oral administration should be in dosages suitable for the chosen route of administration.

For buccal administration, the compositions may take the form of tablets or lozenges formulated in conventional manner.

For administration by nasal inhalation, the active ingredients for use according to the present invention are conveniently delivered in the form of an aerosol spray presentation from a pressurized pack or a nebulizer with the use of a suitable propellant, e.g., dichlorodifluoromethane, trichlorofluoromethane, dichloro-tetrafluoroethane or carbon dioxide. In the case of a pressurized aerosol, the dosage unit may be determined by providing a valve to deliver a metered amount. Capsules and cartridges of, e.g., gelatin for use in a dispenser may be formulated containing a powder mix of the compound and a suitable powder base such as lactose or starch.

The preparations described herein may be formulated for parenteral administration, e.g., by bolus injection or continuous infusion. Formulations for injection may be presented in unit dosage form, e.g., in ampoules or in multidose containers with optionally, an added preservative. The compositions may be suspensions, solutions or emulsions in oily or aqueous vehicles, and may contain formulatory agents such as suspending, stabilizing and/or dispersing agents.

Pharmaceutical compositions for parenteral administration include aqueous solutions of the active preparation in water-soluble form. Additionally, suspensions of the active ingredients may be prepared as appropriate oily or water based injection suspensions. Suitable lipophilic solvents or vehicles include fatty oils such as sesame oil, or synthetic fatty acids esters such as ethyl oleate, triglycerides or liposomes. Aqueous injection suspensions may contain substances, which increase the viscosity of the suspension, such as sodium carboxymethyl cellulose, sorbitol or dextran. Optionally, the suspension may also contain suitable stabilizers or agents which increase the solubility of the active ingredients to allow for the preparation of highly concentrated solutions.

Alternatively, the active ingredient may be in powder form for constitution with a suitable vehicle, e.g., sterile, pyrogen-free water based solution, before use.

The preparation of the present invention may also be formulated in rectal compositions such as suppositories or retention enemas, using, e.g., conventional suppository bases such as cocoa butter or other glycerides.

Pharmaceutical compositions suitable for use in context of the present invention include compositions wherein the active ingredients are contained in an amount effective to achieve the intended purpose. More specifically, a therapeutically effective amount means an amount of active ingredients effective to prevent, alleviate or ameliorate symptoms of disease or prolong the survival of the subject being treated.

Determination of a therapeutically effective amount is well within the capability of those skilled in the art.

For any preparation used in the methods of the invention, the therapeutically effective amount or dose can be estimated initially from in vitro assays. For example, a dose can be formulated in animal models and such information can be used to more accurately determine useful doses in humans.

Toxicity and therapeutic efficacy of the active ingredients described herein can be determined by standard pharmaceutical procedures in vitro, in cell cultures or experimental animals. The data obtained from these in vitro and cell culture assays and animal studies can be used in formulating a range of dosage for use in human. The dosage may vary depending upon the dosage form employed and the route of administration utilized. The exact formulation, route of administration and dosage can be chosen by the individual physician in view of the patient's condition. [See e.g., Fingl, et al., (1975) "The Pharmacological Basis of Therapeutics", Ch. 1 p. 1].

Depending on the severity and responsiveness of the condition to be treated, dosing can be of a single or a plurality of administrations, with course of treatment lasting from several days to several weeks or until cure is effected or diminution of the disease state is achieved.

The amount of a composition to be administered will, of course, be dependent on the subject being treated, the severity of the affliction, the manner of administration, the judgment of the prescribing physician, etc.

It will be appreciated that the polynucleotides of the present invention can be provided to the individual with additional active agents to achieve an improved therapeutic effect as compared to treatment with each agent by itself. In such therapy, measures (e.g., dosing and selection of the complementary agent) are taken to adverse side effects which may be associated with combination therapies.

Compositions including the preparation of the present invention formulated in a compatible pharmaceutical carrier may also be prepared, placed in an appropriate container, and labeled for treatment of an indicated condition.

Compositions of the present invention may, if desired, be presented in a pack or dispenser device, such as an FDA approved kit, which may contain one or more unit dosage forms containing the active ingredient. The pack may, for example, comprise metal or plastic foil, such as a blister pack. The pack or dispenser device may be accompanied by instructions for administration. The pack or dispenser may also be accommodated by a notice associated with the container in a form prescribed by a governmental agency regulating the manufacture, use or sale of pharmaceuticals, which notice is reflective of approval by the agency of the form of the compositions or human or veterinary administration. Such notice, for example, may be of labeling approved by the U.S. Food and Drug Administration for prescription drugs or of an approved product insert.

As used herein the term "about" refers to ±10%.

The terms "comprises", "comprising", "includes", "including", "having" and their conjugates mean "including but not limited to".

The term "consisting of" means "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

As used herein, the singular form "a", "an" and "the" include plural references unless the context clearly dictates otherwise. For example, the term "a compound" or "at least one compound" may include a plurality of compounds, including mixtures thereof.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

As used herein, the term "treating" includes abrogating, substantially inhibiting, slowing or reversing the progression of a condition, substantially ameliorating clinical or aesthetical symptoms of a condition or substantially preventing the appearance of clinical or aesthetical symptoms of a condition.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Various embodiments and aspects of the present invention as delineated hereinabove and as claimed in the claims section below find experimental support in the following examples.

EXAMPLES

Reference is now made to the following examples, which together with the above descriptions illustrate some embodiments of the invention in a non limiting fashion.

Generally, the nomenclature used herein and the laboratory procedures utilized in the present invention include molecular, biochemical, microbiological and recombinant DNA techniques. Such techniques are thoroughly explained in the literature. See, for example, "Molecular Cloning: A laboratory Manual" Sambrook et al., (1989); "Current Protocols in Molecular Biology" Volumes I-III Ausubel, R. M., ed. (1994); Ausubel et al., "Current Protocols in Molecular Biology", John Wiley and Sons, Baltimore, Md. (1989); Perbal, "A Practical Guide to Molecular Cloning", John Wiley & Sons, New York (1988); Watson et al., "Recombinant DNA", Scientific American Books, New York; Birren et al. (eds) "Genome Analysis: A Laboratory Manual Series", Vols. 1-4, Cold Spring Harbor Laboratory Press, New York (1998); methodologies as set forth in U.S. Pat. Nos. 4,666,828; 4,683,202; 4,801,531; 5,192,659 and 5,272,057; "Cell Biology: A Laboratory Handbook", Volumes I-III Cellis, J. E., ed. (1994); "Culture of Animal Cells—A Manual of Basic Technique" by Freshney, Wiley-Liss, N.Y. (1994), Third Edition; "Current Protocols in Immunology" Volumes I-III Coligan J. E., ed. (1994); Stites et al. (eds), "Basic and Clinical Immunology" (8th Edition), Appleton & Lange, Norwalk, Conn. (1994); Mishell and Shiigi (eds), "Selected Methods in Cellular Immunology", W. H. Freeman and Co., New York (1980); available immunoassays are extensively described in the patent and scientific literature, see, for example, U.S. Pat. Nos. 3,791,932; 3,839,153; 3,850,752; 3,850,578; 3,853,987; 3,867,517; 3,879,262; 3,901,654; 3,935,074; 3,984,533; 3,996,345; 4,034,074;

4,098,876; 4,879,219; 5,011,771 and 5,281,521; "Oligonucleotide Synthesis" Gait, M. J., ed. (1984); "Nucleic Acid Hybridization" Hames, B. D., and Higgins S. J., eds. (1985); "Transcription and Translation" Hames, B. D., and Higgins S. J., eds. (1984); "Animal Cell Culture" Freshney, R. I., ed. (1986); "Immobilized Cells and Enzymes" IRL Press, (1986); "A Practical Guide to Molecular Cloning" Perbal, B., (1984) and "Methods in Enzymology" Vol. 1-317, Academic Press; "PCR Protocols: A Guide To Methods And Applications", Academic Press, San Diego, Calif. (1990); Marshak et al., "Strategies for Protein Purification and Characterization—A Laboratory Course Manual" CSHL Press (1996); all of which are incorporated by reference as if fully set forth herein. Other general references are provided throughout this document. The procedures therein are believed to be well known in the art and are provided for the convenience of the reader. All the information contained therein is incorporated herein by reference.

General Materials and Methods

Cells.

U87MG, MDA-MB-435S, MDA-MB-231 and HEK 293 cells were grown in DMEM supplemented with 10% (v/v) FCS, penicillin and streptomycin.

Immunoblotting.

Cells were harvested in Laemmli buffer and analyzed for total protein concentration [31]. 15 μg of total protein from each cell lysate was separated by SDS-PAGE and transferred onto a PVDF membrane (Invitrogen). The membranes were probed with primary antibodies. Primary antibodies: β-actin (1:200 Santa Cruz), RBFOX2 (1:4000 Sigma), SRSF1 (mAb AK96 culture supernatant, 1:200 [32]), SRSF5 (1:3000 Sigma), SRSF6 (mAb 8-1-28 culture supernatant 1:500), OctA (flag tag) (1:500 Santa Cruz), α+β tubulin I+II (1:1000 Sigma), phospho-p38 (Thr180/Tyr182) (1:1000 cell signaling), p38 (1:1000 Santa Cruz), phospho-ATF2 (Thr71) (1:1000 Cell Signaling), ATF2 (1:1000 abcam). Secondary antibodies: HRP-conjugated goat anti-mouse, gout anti-rabbit or donkey anti-goat IgG (H+L) (1:10,000, Jackson Laboratories).

RT-PCR.

Total RNA was extracted with TRIzol reagent (Sigma) and 1 μg of total RNA was reverse transcribed using High Capacity cDNA Reverse Transcription Kit of Applied Biosystems. PCR was conducted on 1 μl of cDNA by KAPA 2G Fast HS ReadyMix PCR kit (KAPA Biosystems). PCR conditions were as described in manufacturer's protocol of ReadyMix with the addition of 5% (v/v) DMSO for 30, 35 or 40 cycles. PCR products were separated on 2% agarose gels. Primers appear in Table 1, herein below.

RT-qPCR.

Total RNA was extracted with TRIzol reagent (Sigma) and 1 μg of total RNA was reverse transcribed using High Capacity cDNA Reverse Transcription Kit of Applied Biosystems.

qPCR was performed on the cDNA using SYBR green (Applied Biosystems) and the CFX96 (Bio-Rad) real-time PCR machine. Normalization was performed using either β-actin or RPL14. Unknown samples were compared to a standard curve, which was established by serial dilutions of a known concentration of cDNA. The PCR reaction is composed of the following steps: one cycle for 30 sec at 95° C. and 39 cycles of 5 sec at 95° C. and 30 sec at 59° C.-63° C. according to primers Tm. Primers are listed in Supplemental Table S1.

Transfection of Oligos.

Cells were transfected with oligos using lipofectamine 2000 (Invitrogen) according to manufacturer's protocol.

Stable Cell Lines.

To generate stable cell lines, U87MG and MDA-MB-231 cells were transduced with MSCV-puro-shRNAs retroviral vectors against RBFOX2 (received from Zhang at al. 2008) Medium was replaced 24 h after infection, and 24 h later, infected cells were selected with puromycin (2 μg/mL) for 72 h.

Anchorage-Independent Growth.

Colony formation was assayed as described previously (Shimoni-Sebag, A., et al. 2013).

Growth Curves.

4,000 cells per well were seeded in 96-well plates, fixed and stained with methylene blue. The A650 of the acid-extracted stain was measured on a plate reader (BioRad).

Survival Assay.

Cells were transfected with oligos. 48 h post transfection medium was collected, cells were washed with PBS which was also collected, trypsinized and spun down. Cells were resuspended with HBSS and the percentage of dead cells was determined with trypan blue 0.4% using a Bio-Rad cell counter.

Clonogenic Assay.

1000, 500 and 250 cells were seeded in 6 well plates. After 10-21 days cells were fixated with 2.5% glutaraldehyde solution for 10-15 min and stained with 1% methylene blue solution.

Pull Down Assay.

Nuclear extract (NE) were lysed in a buffer containing 20 mM Hepes, 1.5 mM McCl$_2$, 420 mM NaCl, 0.2 mM EDTA and 25% (v/v) glycerol. NE was incubated with biotin tagged oligos and then streptavidin beads (Thermo Scientific), previously blocked with a solution containing heparin, were added. Pulled down content was lysed in Laemmli buffer and analyzed by western blot analysis.

Zebrafish Injections.

Tupfel Long-fin (aka TL) zebrafish breeding and maintenance were performed as previously described [33]. 5 or 8 pg of oligos were injected into zebrafish embryos at the 1-2-cell stage. Injected embryos were allowed to develop at 28.5° C. 48 hours post fertilization (hpf) embryos were fixed in 4% paraformaldehyde for immunohistochemistry or solubilized in TRIzol reagent (Sigma) and analyzed as described for RT-PCR.

Immunohistochemistry.

Embryos were fixed overnight in 4% paraformaldehyde and permeabilized with triton. Alexa Fluor 594 conjugated phalloidin (Invitrogen) was used at 1 unit/ml following manufacturer's instructions. Embryos were mounted in 80% glycerol.

TABLE 1

| RT-PCR Primers | |
|---|---|
| Human INSR | For- SEQ ID NO: 67 |
|  | Rev- SEQ ID NO: 68 |
| Human MKNK2 | For- SEQ ID NO: 69 |
|  | Rev- SEQ ID NO: 70 |
|  | Rev- SEQ ID NO: 71 |
| Human U2AF1 | For- SEQ ID NO: 72 |
|  | Rev- SEQ ID NO: 73 |
| Human ATF3 | For- SEQ ID NO: 74 |
|  | Rev- SEQ ID NO: 75 |
| Human CARS | For- SEQ ID NO: 76 |
|  | Rev- SEQ ID NO: 77 |

TABLE 1-continued

RT-PCR Primers

| | |
|---|---|
| Human c-FOS | For- SEQ ID NO: 78 |
| | Rev- SEQ ID NO: 79 |
| Human IL-6 | For- SEQ ID NO: 80 |
| | Rev- SEQ ID NO: 81 |
| Human COX2 | For- SEQ ID NO: 82 |
| | Rev- SEQ ID NO: 83 |
| Human ABI1 | For- SEQ ID NO: 84 |
| | Rev- SEQ ID NO: 85 |
| Human FMNL3 | For- SEQ ID NO: 86 |
| | Rev- SEQ ID NO: 87 |
| Human FAM126A | For- SEQ ID NO: 88 |
| | Rev- SEQ ID NO: 89 |
| Human NUMA1 | For- SEQ ID NO: 90 |
| | Rev- SEQ ID NO: 91 |
| Human β-actin | For- SEQ ID NO: 92 |
| | Rev- SEQ ID NO: 93 |
| Human RPL14 | For- SEQ ID NO: 94 |
| | Rev- SEQ ID NO: 95 |
| Human SNAP2 | For- SEQ ID NO: 96 |
| | Rev- SEQ ID NO: 97 |
| Human PKM2 | For- SEQ ID NO: 98 |
| | Rev- SEQ ID NO: 99 |
| | Rev- SEQ ID NO: 100 |
| Human RTN4 | For- SEQ ID NO: 101 |
| | Rev- SEQ ID NO: 102 |
| Zebrafish fxr1 | For- SEQ ID NO: 103 |
| | Rev- SEQ ID NO: 104 |
| Zebrafish ube2d3 | For- SEQ ID NO: 105 |
| | Rev- SEQ ID NO: 106 |
| Zebrafish synela | For- SEQ ID NO: 107 |
| | Rev- SEQ ID NO: 108 |
| Zebrafish scn88a | For- SEQ ID NO: 109 |
| | Rev- SEQ ID NO: 110 |
| Zebrafish Ef1α | For- SEQ ID NO: 111 |
| | Rev- SEQ ID NO: 112 |

Results

Figure 2A:
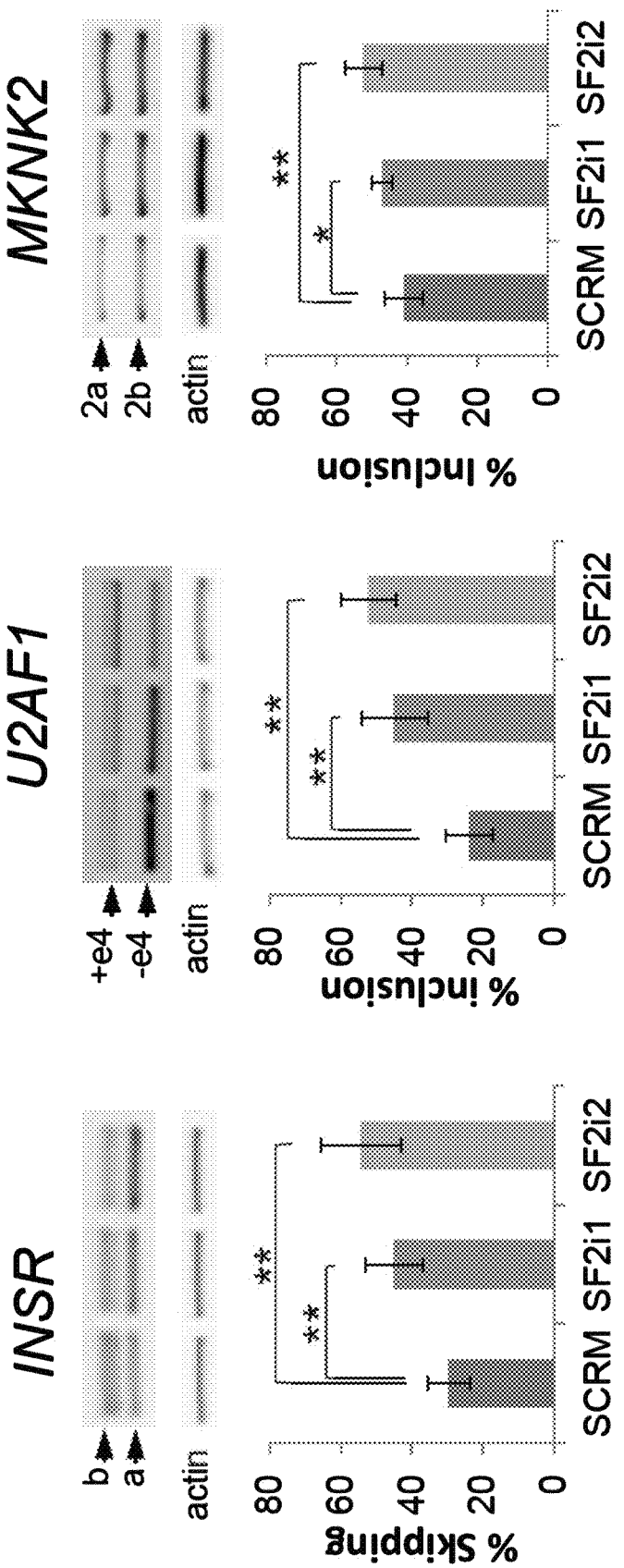
Figure 2D:
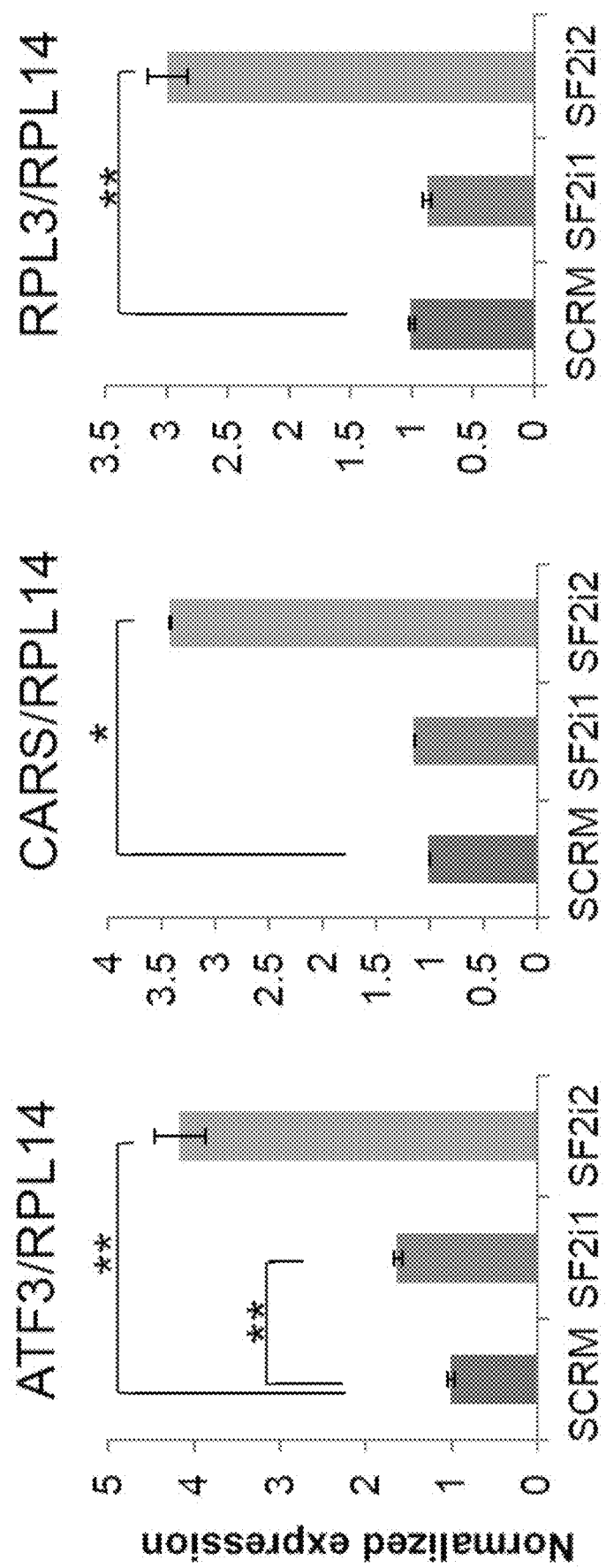
Figure 5B:
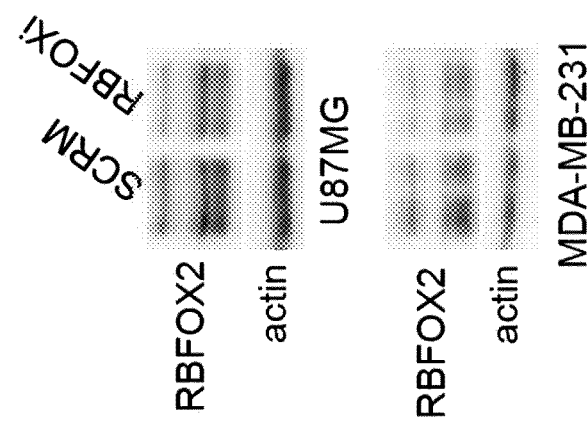
Figure 5A:
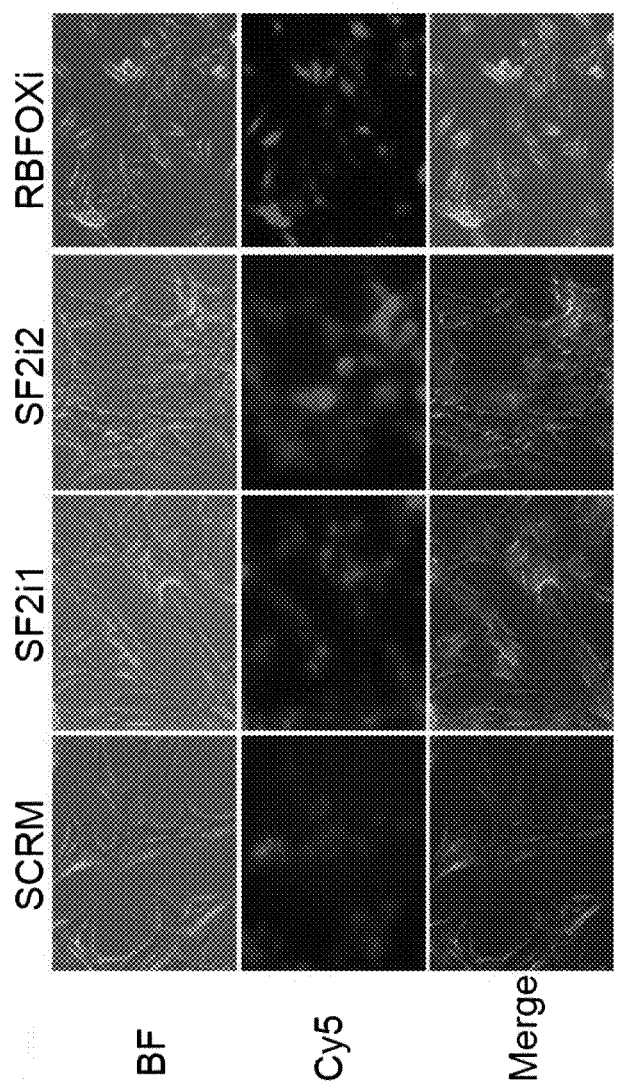
Figure 5F:
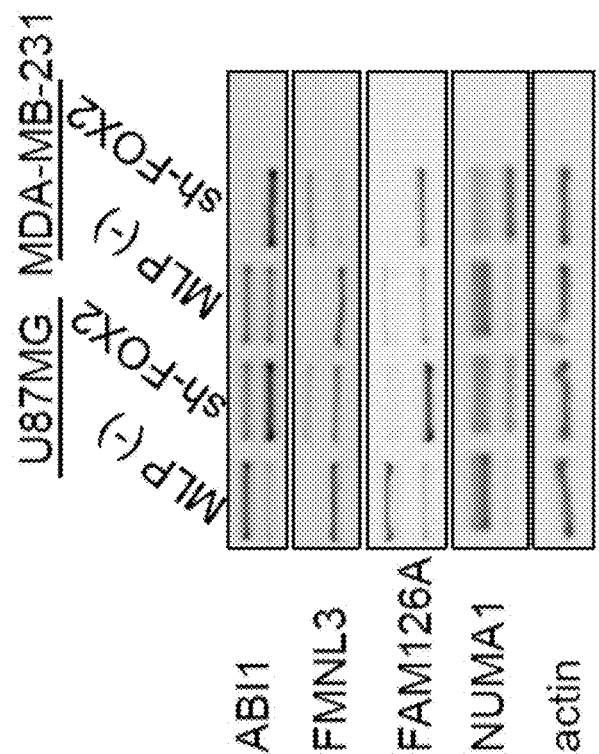
Figure 5E:
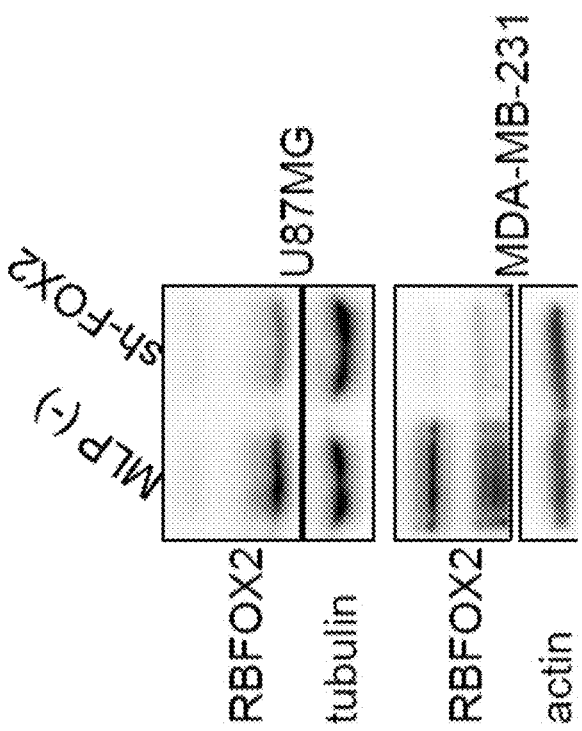
Figures 6A, 6B:
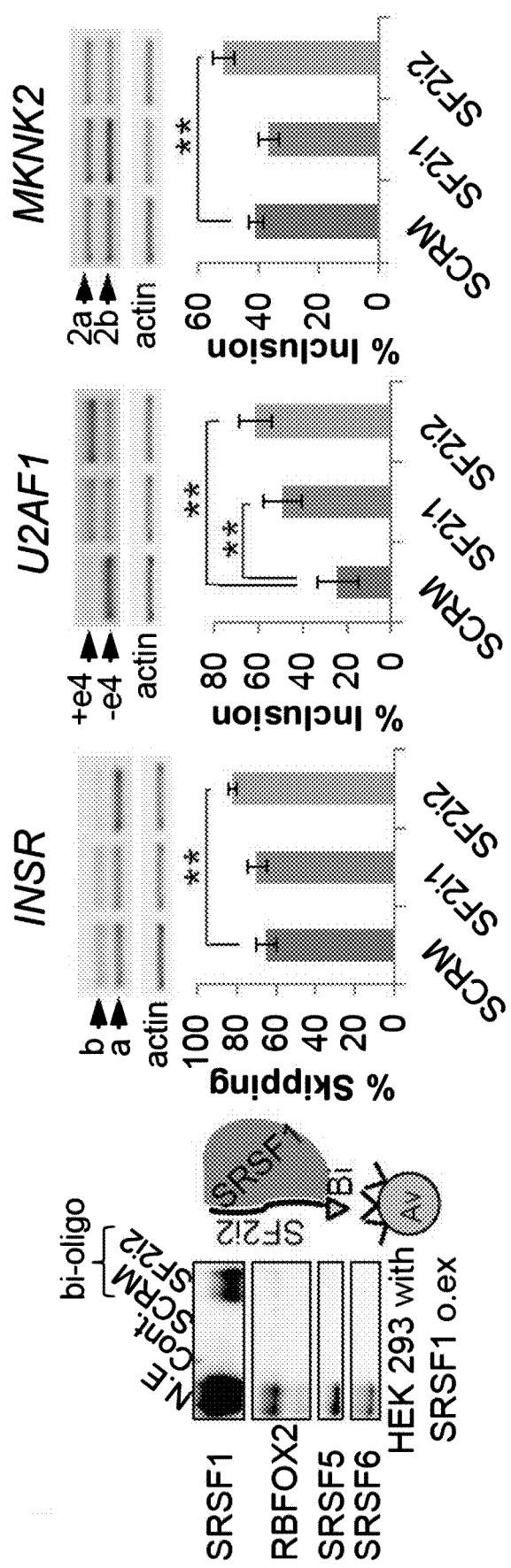
Figure 6G:
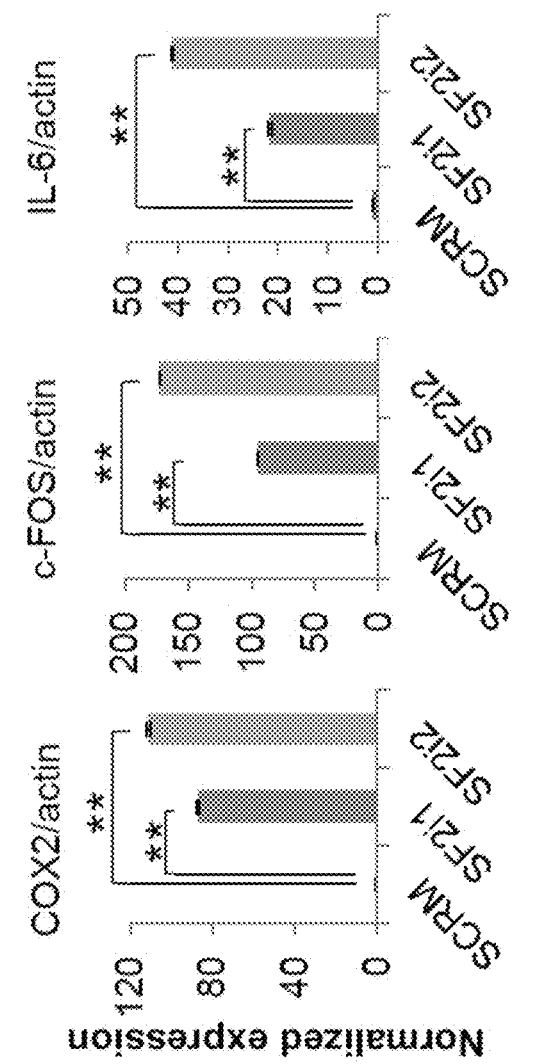
Figure 6F:
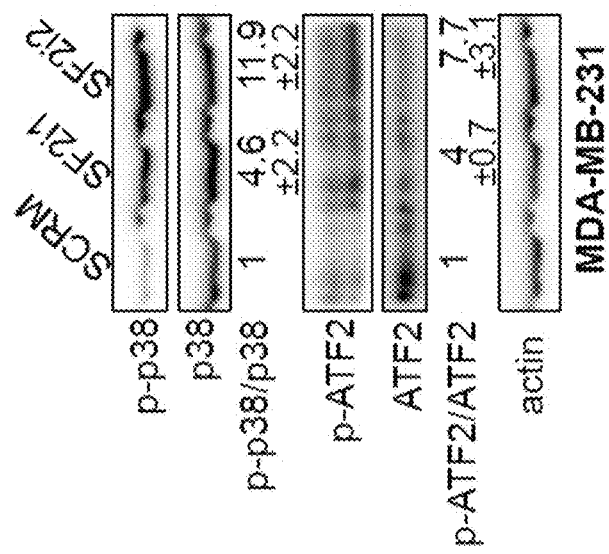

RNA decoy oligonucleotides were designed against three alternative SFs; RBFOX1/2, PTBP1 and SRSF1. The predicted motifs were determined to bind the RRM domain of each SF (FIG. 1A), based on several studies. Each oligonucleotide contains three/four tandem motif repeats. An oligonucleotide that does not resemble any of the known SF motifs, scrambled (SCRM), was used as a control for all experiments. The oligos were modified with 2'-O-methyl and Cy5 or biotin for stability and detection, respectively. Introduction of the oligonucleotides into U87MG cells resulted in nuclear localization of the oligos (FIG. 5A). Pulldown assays in 293 cells overexpressing either RBFOX or SRSF1 showed efficient binding of each oligo to its specific SF (FIG. 1B, FIG. 6A). Modest to no downregulation of these SFs at the protein level was observed (FIG. 6B, 2D).

Example 1

RBFOX2 Inhibition Using Decoy Oligonucleotides

After determining that the RBFOX decoy oligo (RB-FOXi) binds to RBFOX2 (FIG. 1B) the present inventors established that this binding results in a change in splicing of known RBFOX splicing targets (FIG. 1C, FIG. 5C) in a dose dependent manner (FIG. 5D). These alternative splicing changes are similar to the changes observed in U87MG and MDA-MB-231 cells upon RBFOX2 knockdown (FIGS. 5E-F) and to previous reports[6].

Figure 1E:
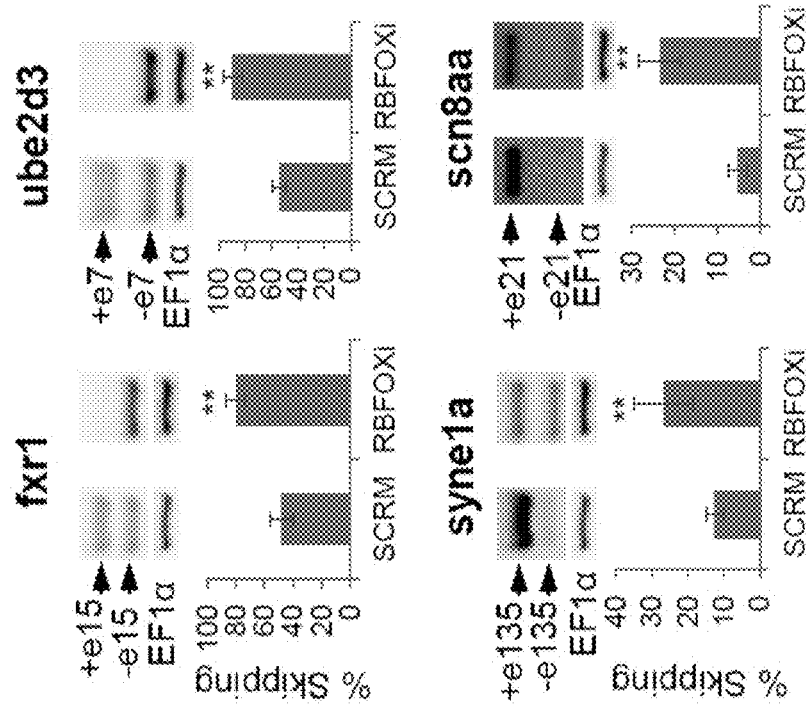

It has been shown that RBFOX proteins are essential for the development and function of muscle and heart in zebrafish. This model system was used to determine if inhibition of RBFOX proteins with the decoy oligos results in the same phenotype as RBFOX knockdown by morpholino antisense oligos. Fertilized zebrafish eggs were injected with RBFOXi and SCRM oligos (FIG. 1D) Changes in alternative splicing of four (muscle related) known RBFOX targets were observed in RNA isolated from fertilized zebrafish eggs injected with RBFOXi compared to those injected with SCRM oligos (FIG. 1E). Phalloidin labeling of F-actin filaments of larva of zebrafish developed from eggs injected with RBFOXi revealed that muscle fibers appeared disorganized and wavy, with a higher dose of RBFOXi (8 pg vs. 5 pg) having a more severe phenotype (FIG. 1F-G). These results were similar to those reported by Gallagher, et al.[2] and suggest that inhibition of the RNA binding properties of RBFOX proteins by the decoy oligonucleotide and the concomitant change in splicing result in a delayed muscle development phenotype in vivo.

Example 2

SRSF1 Inhibition Using Decoy Oligonucleotides

Figure 6H:
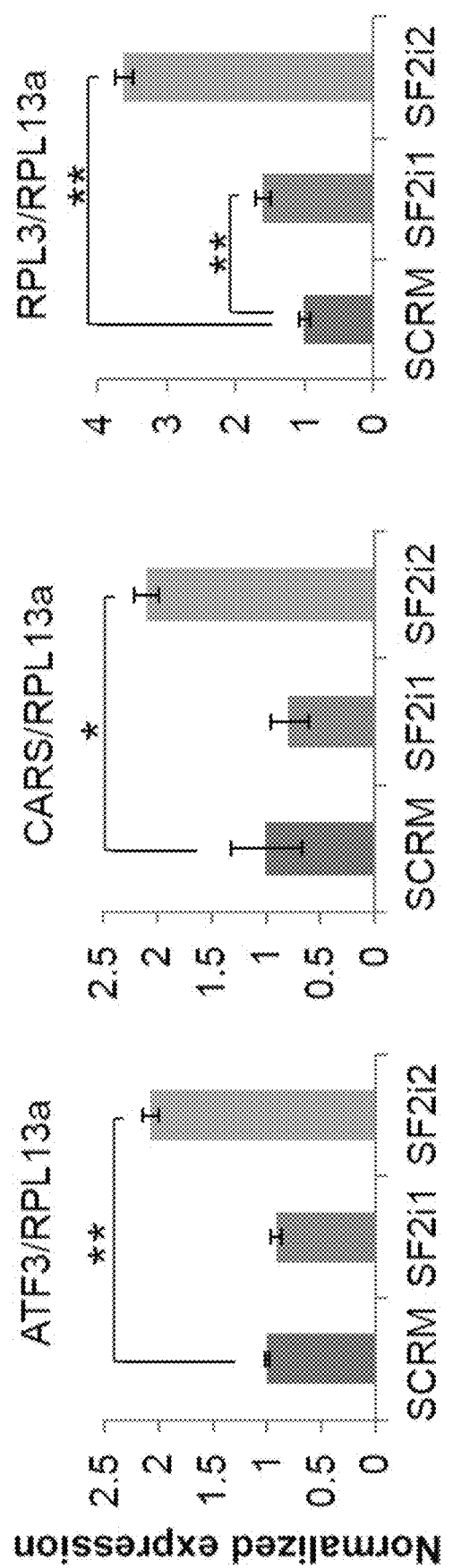

Two decoy oligonucleotides (SF2i1 and SF2i2) were designed to inhibit the splicing factor SRSF1. Introduction of these oligos into U87MG and MDA-MB-231 cells resulted in changes in splicing of three known targets of SRSF1—namely INSR[7], U2AF1[8] and MKNK2[3] when compared to cells with SCRM oligo (FIG. 2A and FIG. 6B). Splicing patterns were altered in a dose dependent manner (FIG. 6C). Both SRSF1 decoy oligos had similar effects on splicing of SRSF1 targets, with SF2i2 having a stronger effect than SF2i1 (FIG. 2A and FIG. 6B). To determine the effect, if any, of number of motif repeats on the efficiency of the decoy oligo, oligos containing one to five repeats of the motif CGCAGGA (SF2i2) were tested. The effect on splicing of U2AF1 and MKNK2 correlated with motif repeat number, with five repeats having the greatest effect on splicing. Changes in splicing of the INSR reached a plateau with oligos containing three-four repeats, with no further effect of additional motif repeats (FIG. 6D). Elevated expression of MNK2a, a result of alternative splicing of MKNK2, is known to activate the p38-MAPK stress pathway[3]. Next, the present inventors examined if inhibition of SRSF1 by the decoy oligos activates this stress pathway. Increased phosphorylation of p38-MAPK and its substrate ATF2 was observed (FIG. 2B, FIG. 6F) as well as upregulation of the expression of downstream transcriptional targets of the p38-MAPK pathway; COX2, c-FOS and IL-6[10] (FIG. 2C, FIG. 6G) in cells transfected with the decoy SRSF1 oligos compared to cells transfected with SCRM oligo. SRSF1's role in nonsense mediated decay (NMD)[11] is also mediated through its RRM domains. The present inventors therefore predicted that inhibition of SRSF1 with decoy oligos would have an effect on Nonsense mediated decay (NMD). Expression of three known NMD targets[12,13] is elevated in cells after treatment with oligos, suggesting that NMD was inhibited. As in previous assays, SF2i2 had a stronger effect than SF2i1 (FIG. 2D, FIG. 6H). These results demonstrate that the SRSF1 decoy oligos inhibit SRSF1's ability to enhance NMD, regulate alternative splicing, and lead to activation of the p38-MAPK stress pathway.

Example 3

Treatment of Cancer Using Decoy Oligonucleotides Against SRSF1

Figures 3A, 3B, 3C:
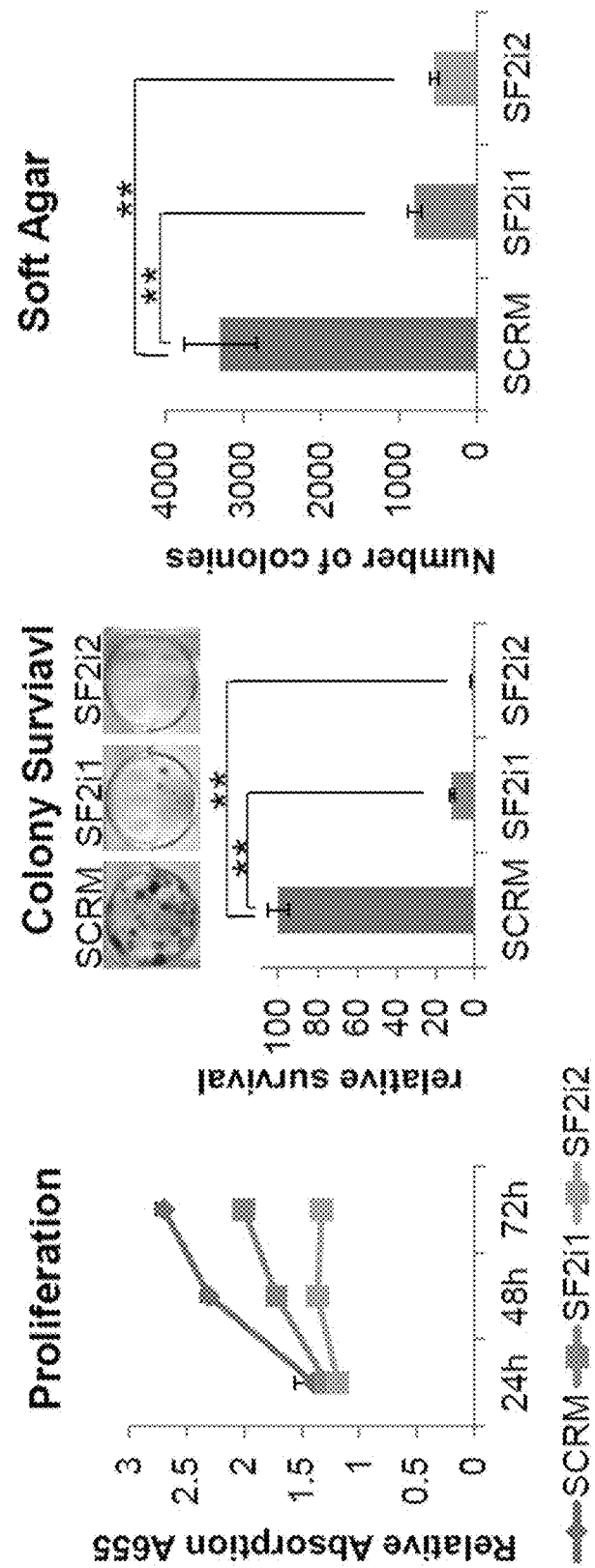
Figures 3G, 3H:
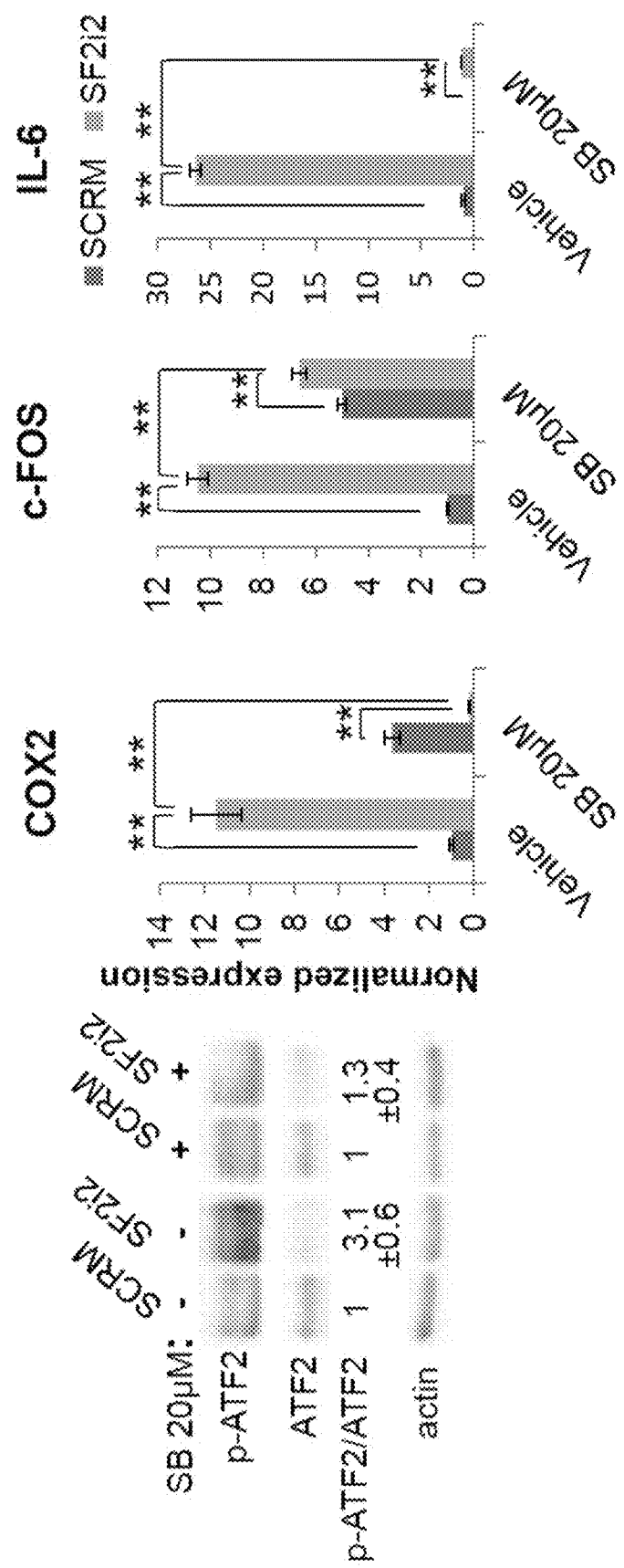
Figure 7A:
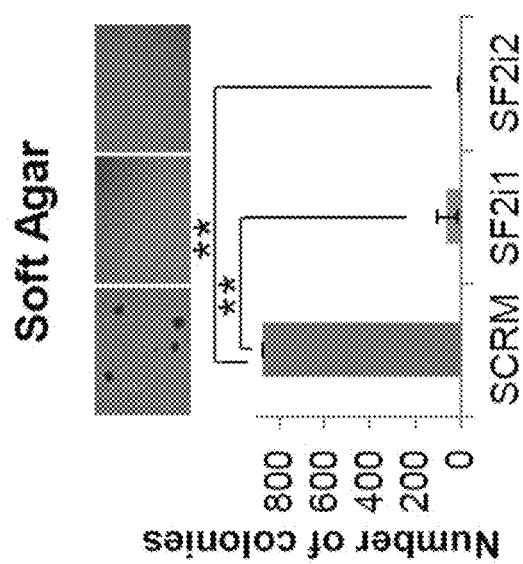
Figure 7B:
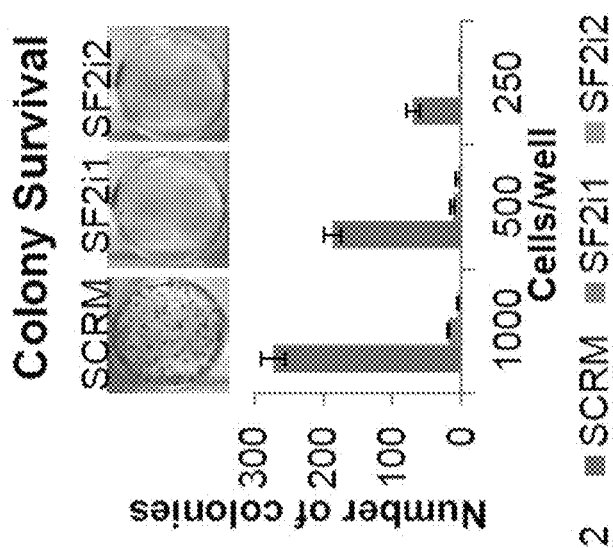
Figure 7C:
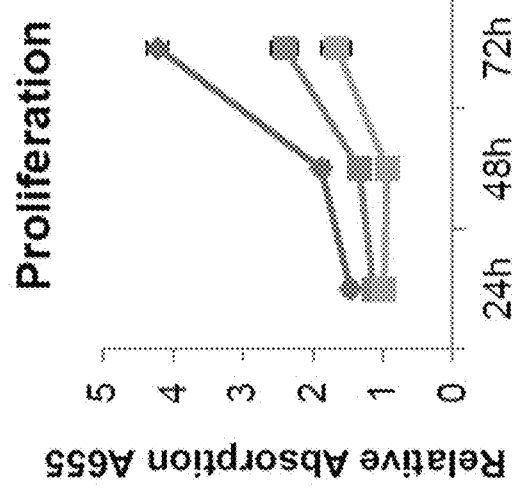
Figure 7I:
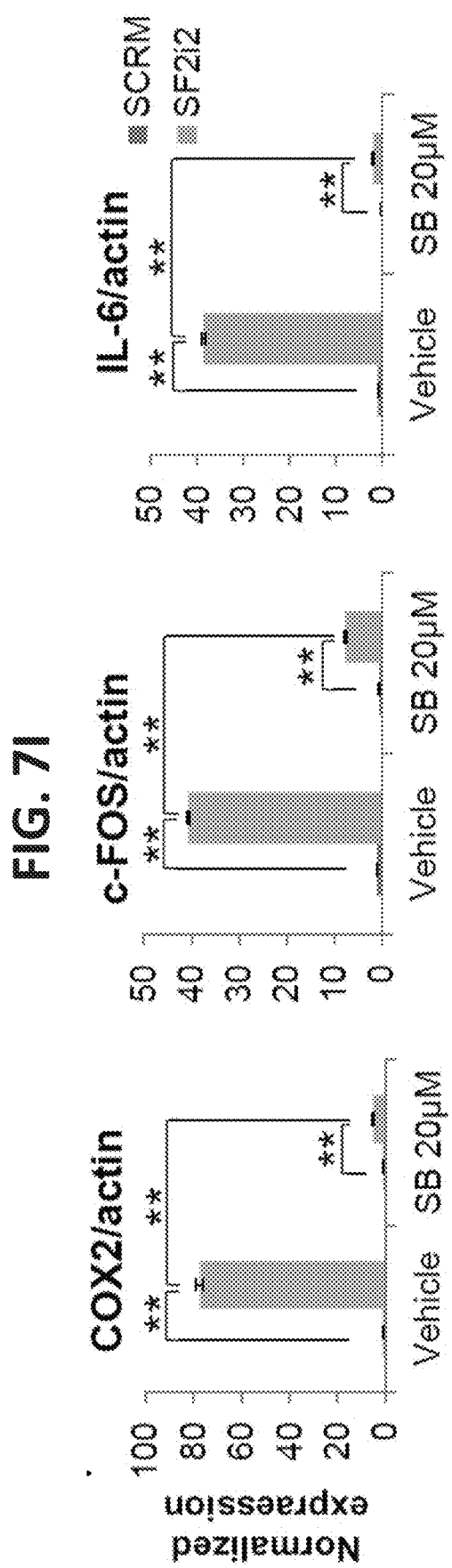

Given that SRSF1 acts as an oncoprotein and its inhibition with decoy oligos activated the p38-MAPK stress pathway, the present inventors predicted that treatment of cancer cells with SRSF1 decoy oligos would result in reduced oncogenic abilities. Indeed, treatment of cells with SFRSF1 decoy oligos, SF2i1 and SF2i2, inhibited proliferation (almost 3-4 fold) compared to RBFOXi or SCRM oligo (FIG. 3A, FIG. 7A). In a colonogenic assay that assesses the ability of cells to survive and proliferate under stress conditions, SF2i1 and SF2i2 dramatically inhibited the cells' ability to form colonies compared to the scrambled oligo (FIG. 3B, FIG. 7B, D). The ability to form colonies in soft agar was also strongly reduced in cells treated with SF2i1 and SF2i2, while treatment with RBFOXi had an insignificant effect (FIG. 3C, FIG. 7C). To verify that the observed reduced oncogenic activity is due to activation of the p38-stress pathway, the p38-MAPK inhibitor SB203580 was used (FIG. 3D). The ability of cells with SF2i1 and SF2i2 to form colonies in soft agar and colony survival was significantly increased (4 fold) after treatment with SB203580 compared to cells treated with vehicle (FIGS. 3E-F, FIG. 7E-H). A concurrent reduction in ATF2 phosphorylation and decreased expression of downstream targets COX2, c-FOS and IL-6 was also observed (FIG. 3G-H, FIG. 7I). These results demonstrate that SRSF1 decoy oligos can inhibit malignant properties of glioblastoma and breast cancer cells through activation of the p38-MAPK pathway.

Figure 4A:
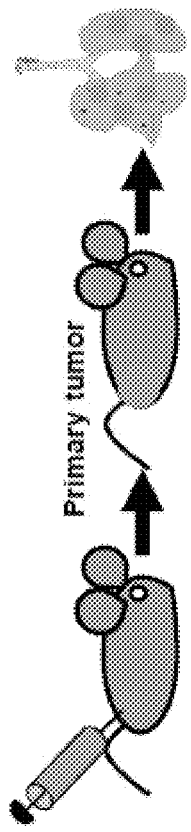
Figure 4B:
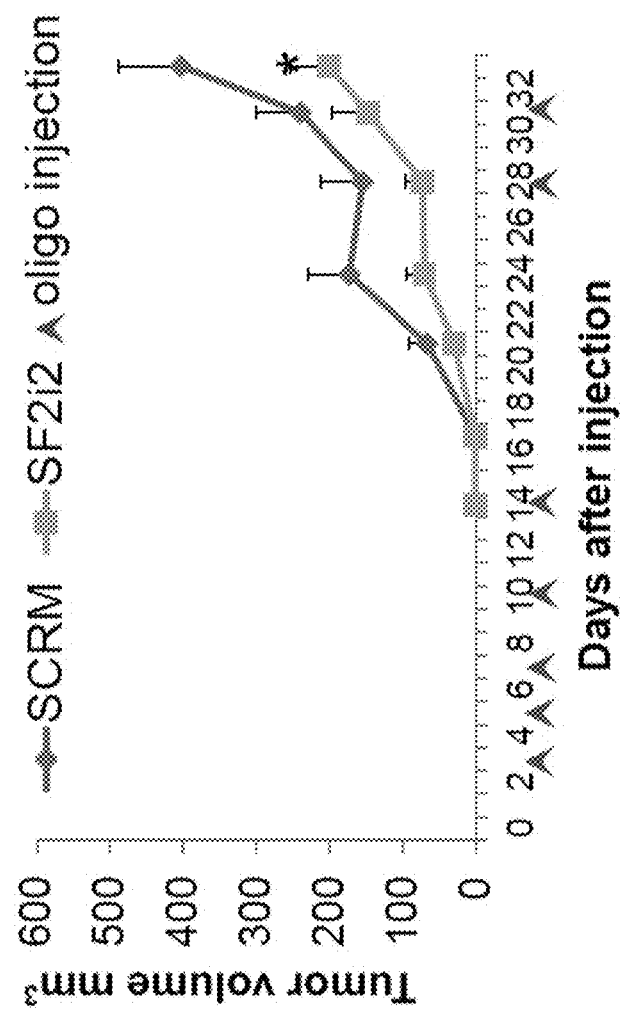
Figure 4D:
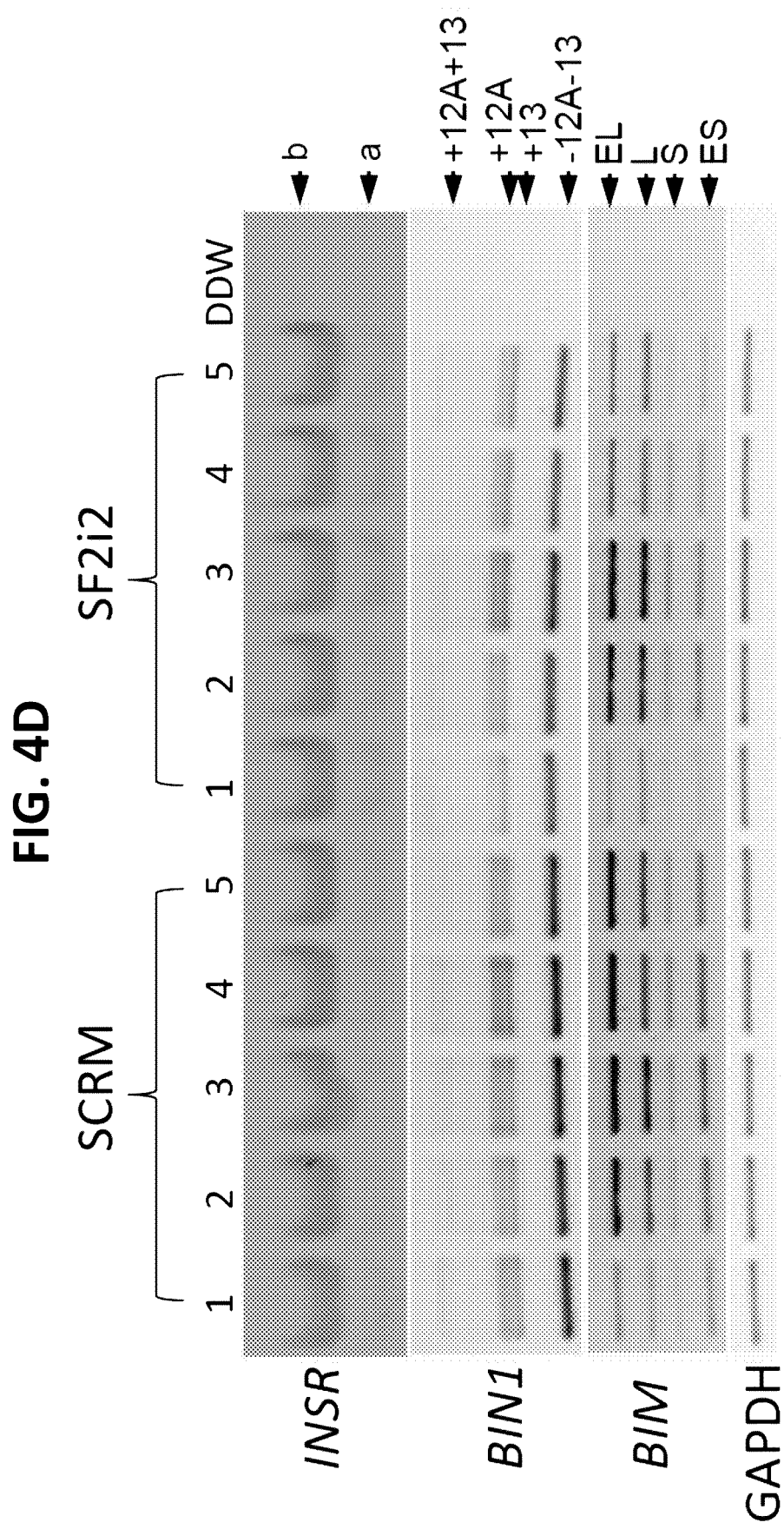

Next the effect of the SRSF1 decoy oligos were tested in an in vivo cancer model system. GFP-labeled MDA-MB-231 cells were injected subcutaneously into NOD-SCID mice. These cells are known to be invasive and are able to metastasize to the lungs (FIG. 4A). SF2i2 or SCRM oligos modified with phosphothioated backbone (for stability in vivo) were injected IP three days after injection of the MDA-MB-231 cells (three times a week, 100 mg/kg). Mice were sacrificed 28 days after cell injection. No toxicity of the oligos was observed during the duration of the experiment. Tumor volume was measured starting from day 12 after cell injection and lung metastasis was assessed after the animals were sacrificed. Mice treated with SF2i2 showed inhibited tumor growth (FIG. 4B) and decreased metastasis formation compared to SCRM treated mice (FIG. 4C). Changes in splicing of SRSF1 targets INSR, BIN1, and BIM[14] (U2AF1 and MKNK2 undergo different splicing in humans and mice) were determined in RNA from mice livers and showed the expected change in their splicing patterns (FIG. 4D). These results demonstrate that the SF2i2 oligo can decrease tumorigenesis in vivo and has a pronounced effect on the spread of metastasis.

Example 4

Figure 8D:
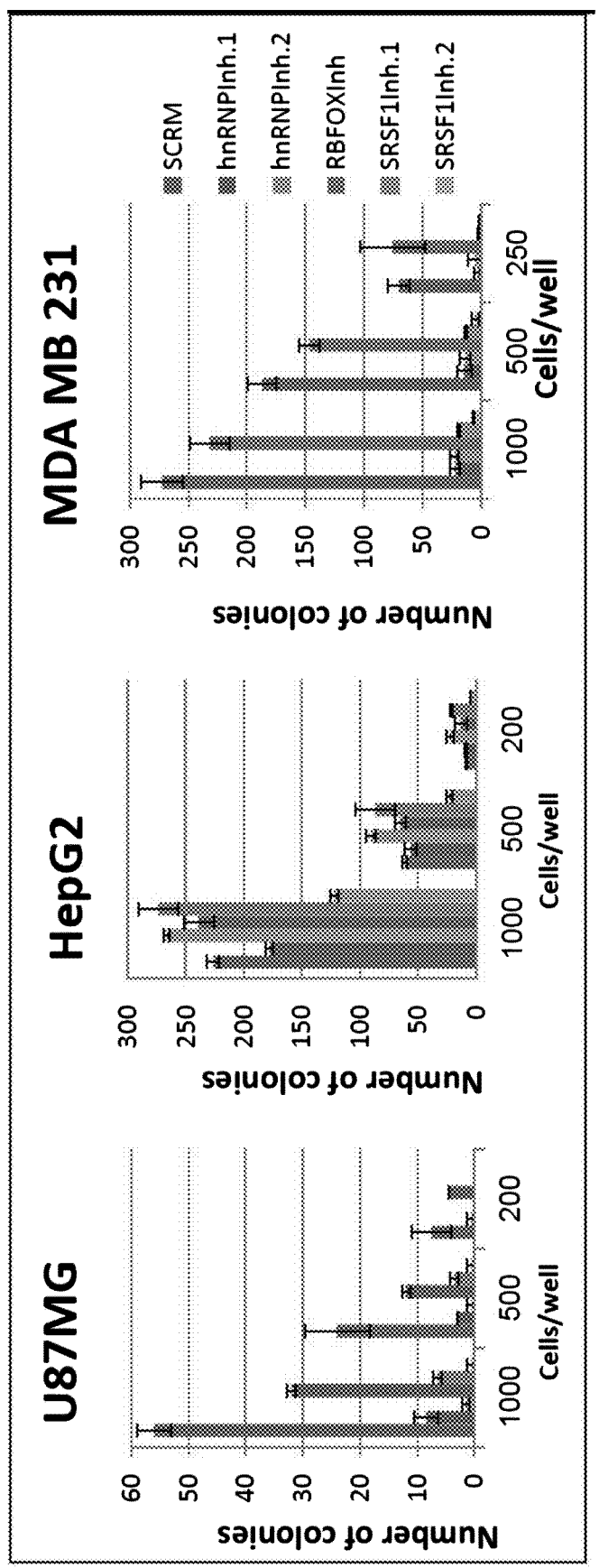

Treatment of Cancer Using Decoy Oligonucleotides Against hnRNP A1/A2 hnRNP A1 and hnRNP A2/B1 are up-regulated in many cancers and have been shown to promote transformation. Transfection of decoy oligonucleotides against hnRNP A1/A2 or SRSF1 inhibited colony formation in soft agar, and colony survival of glioblastoma (U87MG) and breast cancer (MDA-MB-231) cells (FIG. 8A-D). Hepatocellular carcinoma cells (HepG2) were inhibited only by SRSF1 decoy oligo (FIG. 8D). Transfection of decoy oligonucleotides against hnRNP A1/A2 or SRSF1 inhibited proliferation and enhanced apoptosis of glioblastoma (U87MG) and breast cancer (MDA-MB-231, MDA-MB-436S) cells (FIG. 9A-C).

Example 5

Treatment of Cancer Using Decoy Oligonucleotides Against PTBP1

Figure 10B:
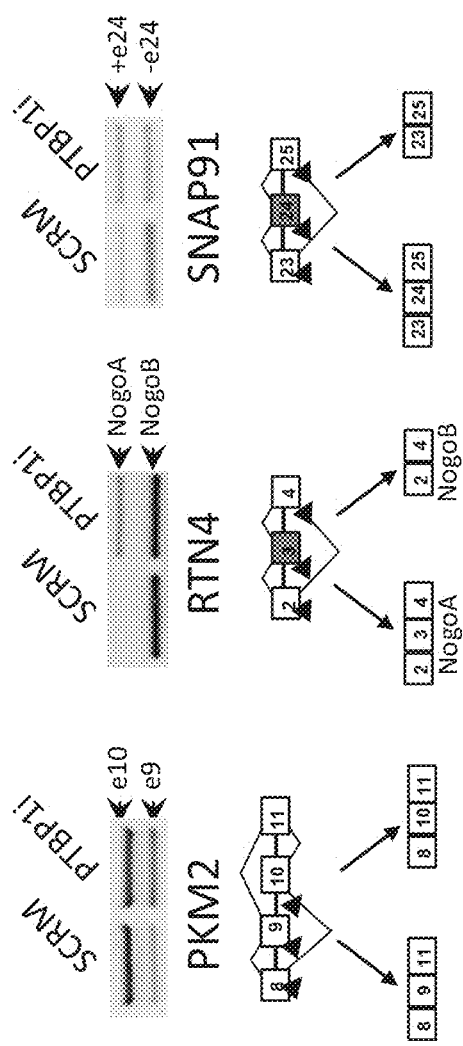
Figure 10A:
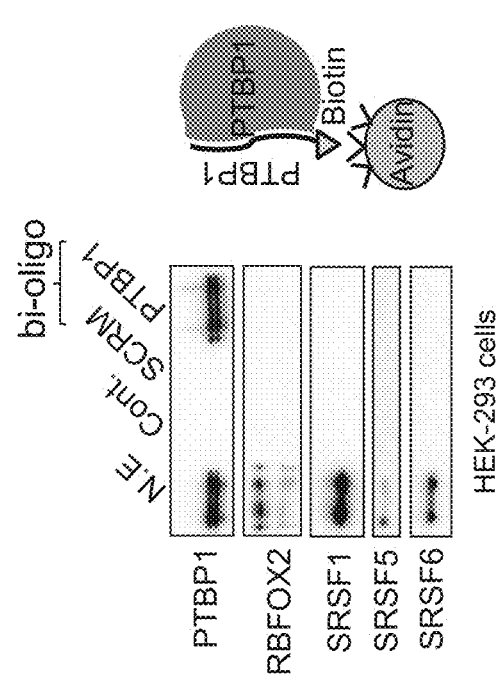

PTBP1 is up-regulated in many cancers including glioblastoma, and modulates cancer metabolism by regulating PKM2 alternative splicing. After determining that the PTBP1 decoy oligo (PTBP1i) binds to PTBP1 (FIG. 10A) the present inventors established that this binding results in a change in splicing of known PTBP1 splicing targets (FIG. 10B). Given that PTBP1 is predicted to be an oncoprotein, the present inventors predicted that treatment of cancer cells with PTBP1 decoy oligos would result in reduced oncogenic abilities. Indeed, treatment of cells with PTBP1 decoy oligos, PTBP1i, inhibited colony survival in a colonogenic assay that assesses the ability of cells to survive and proliferate under stress conditions (FIG. 10C). The ability to form colonies in soft agar was also strongly reduced in cells treated with PTBP1i, while treatment with scrambled oligo had no effect (FIG. 10D). These results demonstrate that the PTBP1i oligo can decrease the oncogenic potential of cancer cells.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

REFERENCES

1. Cartegni, L., Chew, S. L. & Krainer, A. R. Listening to silence and understanding nonsense: exonic mutations that affect splicing. Nat Rev Genet 3, 285-98 (2002).
2. Gallagher, T. L. et al. Rbfox-regulated alternative splicing is critical for zebrafish cardiac and skeletal muscle functions. Dev Biol 359, 251-61 (2011).
3. Maimon, A. et al. Mnk2 alternative splicing modulates the p38-MAPK pathway and impacts Ras-induced transformation. Cell Rep 7, 501-13 (2014).
4. Liu, H. X., Zhang, M. & Krainer, A. R. Identification of functional exonic splicing enhancer motifs recognized by individual SR proteins. Genes Dev 12, 1998-2012 (1998).
5. Jin, Y. et al. A vertebrate RNA-binding protein Fox-1 regulates tissue-specific splicing via the pentanucleotide GCAUG. EMBO J 22, 905-12 (2003).
6. Zhang, C. et al. Defining the regulatory network of the tissue-specific splicing factors Fox-1 and Fox-2. Genes Dev 22, 2550-63 (2008).
7. Sen, S., Talukdar, I. & Webster, N. J. SRp20 and CUG-BP1 modulate insulin receptor exon 11 alternative splicing. Mol Cell Biol 29, 871-80 (2009).

8. Clery, A. et al. Isolated pseudo-RNA-recognition motifs of SR proteins can regulate splicing using a noncanonical mode of RNA recognition. Proc Natl Acad Sci USA 110, E2802-11 (2013).
9. Wada, T. & Penninger, J. M. Mitogen-activated protein kinases in apoptosis regulation. Oncogene 23, 2838-49 (2004).
10. Gupta, J. et al. Dual function of p38alpha MAPK in colon cancer: suppression of colitis-associated tumor initiation but requirement for cancer cell survival. Cancer Cell 25, 484-500 (2014).
11. Zhang, Z. & Krainer, A. R. Involvement of SR proteins in mRNA surveillance. Mol Cell 16, 597-607 (2004).
12. Linde, L. et al. Nonsense-mediated mRNA decay affects nonsense transcript levels and governs response of cystic fibrosis patients to gentamicin. J Clin Invest 117, 683-92 (2007).
13. Bhuvanagiri, M. et al. 5-azacytidine inhibits nonsense-mediated decay in a MYC-dependent fashion. EMBO Mol Med 6, 1593-609 (2014).
14. Shimoni-Sebag, A., Lebenthal-Loinger, I., Zender, L. & Karni, R. RRM1 domain of the splicing oncoprotein SRSF1 is required for MEK1-MAPK-ERK activation and cellular transformation. Carcinogenesis 34, 2498-504 (2013).
15. Voit, T. et al. Safety and efficacy of drisapersen for the treatment of Duchenne muscular dystrophy (DEMAND II): an exploratory, randomised, placebo-controlled phase 2 study. Lancet Neurol 13, 987-96 (2014).
16. Kole, R., Krainer, A. R. & Altman, S. RNA therapeutics: beyond RNA interference and antisense oligonucleotides. Nat Rev Drug Discov 11, 125-40 (2012).

What is claimed is:

1. A method of treating a cancer associated with aberrant splicing comprising administering to a subject in need thereof an effective amount of an oligonucleotide comprising ribonucleotides, the oligonucleotide comprising a nucleic acid sequence of at least two copies of a binding site for a splicing factor, the oligonucleotide being no more than 150 nucleotides, wherein when introduced into the subject, said oligonucleotide reduces the total splicing activity of said splicing factor in the subject, said effective amount being an amount that alleviates or ameliorates symptoms of said cancer, said oligonucleotide being devoid of a sequence that base pairs in the subject with an RNA which comprises said binding site of said splicing factor, thereby treating the cancer.

2. The method of claim 1, wherein said cancer is selected from the group consisting of glioblastoma, liver cancer, lung cancer, colon cancer, pancreatic cancer, melanoma and breast cancer.

3. The method of claim 1, wherein the oligonucleotide comprises no more than five ribonucleotides which are not encoding said binding site of said splicing factor.

4. The method of claim 1, wherein the oligonucleotide comprises no more than 10 copies of said binding site of said splicing factor.

5. A method of treating cancer comprising administering to a subject in need thereof a therapeutically effective amount of an oligonucleotide comprising ribonucleotides, the oligonucleotide comprising a nucleic acid sequence of at least two copies of a binding site for a splicing factor, the oligonucleotide being no more than 150 nucleotides, wherein when introduced into the subject, said oligonucleotide reduces the total splicing activity of said splicing factor in the subject, said oligonucleotide being devoid of a sequence that base pairs in the subject with an RNA which comprises a binding site for a splicing factor which is selected from the group consisting of SRSF1, SRSF2, SRSF6, SRSF9, SRSF10, hnRNP H2, hnRNP L, hnRNP A1/A2, hnRNP A/B, hnRNP C, TRA2, LM0212, SF3b4, TIAR-3, RBMS3, RBM4.3, RBMS8, MOD, ESRP2, A1CF, RBM46, ELAV, SF1, QKI, KHDRBS1, PCBP1, Pbbp2, hnRNPK, FXR2, FXR1, FMR1, PAPI1, RBFOX1/2, RBM24, PTBP1, FUSelement and PABPN1, said effective amount being an amount that alleviates or ameliorates symptoms of said disease, thereby treating the cancer.

6. The method of claim 5, wherein said cancer is selected from the group consisting of glioblastoma, liver cancer, lung cancer, colon cancer, pancreatic cancer, melanoma and breast cancer.

* * * * *

SEQUENCE LISTING

```
<160> NUMBER OF SEQ ID NOS: 114

<210> SEQ ID NO 1
<211> LENGTH: 7
<212> TYPE: RNA
<213> ORGANISM: Artificial sequence
<220> FEATURE:
<223> OTHER INFORMATION: RNA oligonucleotide
<220> FEATURE:
<221> NAME/KEY: repeat_unit
<222> LOCATION: (1)..(7)
<223> OTHER INFORMATION: The oligonucleotides may comprise 1-20 repeats

<400> SEQUENCE: 1 cgcagga                                                                    7

<210> SEQ ID NO 2
<211> LENGTH: 7
<212> TYPE: RNA
<213> ORGANISM: Artificial sequence
<220> FEATURE:
<223> OTHER INFORMATION: RNA oligonucleotide
<220> FEATURE:
<221> NAME/KEY: repeat_unit
<222> LOCATION: (1)..(7)
<223> OTHER INFORMATION: The oligonucleotides may comprise 1-20 repeats

<400> SEQUENCE: 2 cacagga                                                                    7

<210> SEQ ID NO 3
<211> LENGTH: 6
<212> TYPE: RNA
<213> ORGANISM: Artificial sequence
<220> FEATURE:
<223> OTHER INFORMATION: RNA oligonucleotide
<220> FEATURE:
<221> NAME/KEY: repeat_unit
<222> LOCATION: (1)..(6)
<223> OTHER INFORMATION: The oligonucleotides may comprise 1-20 repeats

<400> SEQUENCE: 3 uaggga                                                                     6

<210> SEQ ID NO 4
<211> LENGTH: 10
<212> TYPE: RNA
<213> ORGANISM: Artificial sequence
<220> FEATURE:
<223> OTHER INFORMATION: RNA oligonucleotide
```

```
<400> SEQUENCE: 4
cagcagaaag                                                          10

<210> SEQ ID NO 5
<211> LENGTH: 21
<212> TYPE: RNA
<213> ORGANISM: Artificial sequence
<220> FEATURE:
<223> OTHER INFORMATION: RNA oligonucleotide

<400> SEQUENCE: 5
cgcaggacgc aggacgcagg a                                             21

<210> SEQ ID NO 6
<211> LENGTH: 21
<212> TYPE: RNA
<213> ORGANISM: Artificial sequence
<220> FEATURE:
<223> OTHER INFORMATION: RNA oligonucleotide

<400> SEQUENCE: 6
cacaggacac aggacacagg a                                             21

<210> SEQ ID NO 7
<211> LENGTH: 6
<212> TYPE: RNA
<213> ORGANISM: Artificial sequence
<220> FEATURE:
<223> OTHER INFORMATION: RNA oligonucleotide
<220> FEATURE:
<221> NAME/KEY: repeat_unit
<222> LOCATION: (1)..(6)
<223> OTHER INFORMATION: The oligonucleotides may comprise 1-20 repeats

<400> SEQUENCE: 7 ggagga                                                              6

<210> SEQ ID NO 8
<211> LENGTH: 8
<212> TYPE: RNA
<213> ORGANISM: Artificial sequence
<220> FEATURE:
<223> OTHER INFORMATION: RNA oligonucleotide
<220> FEATURE:
<221> NAME/KEY: repeat_unit
<222> LOCATION: (1)..(8)
<223> OTHER INFORMATION: The oligonucleotides may comprise 1-20 repeats

<400> SEQUENCE: 8 ugaaggac                                                            8

<210> SEQ ID NO 9
<211> LENGTH: 6
<212> TYPE: RNA
<213> ORGANISM: Artificial sequence
<220> FEATURE:
<223> OTHER INFORMATION: RNA oligonucleotide
<220> FEATURE:
<221> NAME/KEY: repeat_unit
<222> LOCATION: (1)..(6)
<223> OTHER INFORMATION: The oligonucleotides may comprise 1-20 repeats

<400> SEQUENCE: 9 gaagga                                                              6

<210> SEQ ID NO 10
<211> LENGTH: 6
```

```
<212> TYPE: RNA
<213> ORGANISM: Artificial sequence
<220> FEATURE:
<223> OTHER INFORMATION: RNA oligonucleotide
<220> FEATURE:
<221> NAME/KEY: repeat_unit
<222> LOCATION: (1)..(6)
<223> OTHER INFORMATION: The oligonucleotides may comprise 1-20 repeats

<400> SEQUENCE: 10 aggaga                                                                        6

<210> SEQ ID NO 11
<211> LENGTH: 6
<212> TYPE: RNA
<213> ORGANISM: Artificial sequence
<220> FEATURE:
<223> OTHER INFORMATION: RNA oligonucleotide
<220> FEATURE:
<221> NAME/KEY: repeat_unit
<222> LOCATION: (1)..(6)
<223> OTHER INFORMATION: The oligonucleotides may comprise 1-20 repeats

<400> SEQUENCE: 11 ggaggg                                                                        6

<210> SEQ ID NO 12
<211> LENGTH: 6
<212> TYPE: RNA
<213> ORGANISM: Artificial sequence
<220> FEATURE:
<223> OTHER INFORMATION: RNA oligonucleotide
<220> FEATURE:
<221> NAME/KEY: repeat_unit
<222> LOCATION: (1)..(6)
<223> OTHER INFORMATION: The oligonucleotides may comprise 1-20 repeats

<400> SEQUENCE: 12 ggaagg                                                                        6

<210> SEQ ID NO 13
<211> LENGTH: 5
<212> TYPE: RNA
<213> ORGANISM: Artificial sequence
<220> FEATURE:
<223> OTHER INFORMATION: RNA oligonucleotide
<220> FEATURE:
<221> NAME/KEY: repeat_unit
<222> LOCATION: (1)..(5)
<223> OTHER INFORMATION: The oligonucleotides may comprise 1-20 repeats

<400> SEQUENCE: 13 agaga                                                                         5

<210> SEQ ID NO 14
<211> LENGTH: 6
<212> TYPE: RNA
<213> ORGANISM: Artificial sequence
<220> FEATURE:
<223> OTHER INFORMATION: RNA oligonucleotide
<220> FEATURE:
<221> NAME/KEY: repeat_unit
<222> LOCATION: (1)..(6)
<223> OTHER INFORMATION: The oligonucleotides may comprise 1-20 repeats

<400> SEQUENCE: 14 gggagg                                                                        6

<210> SEQ ID NO 15
```

```
<211> LENGTH: 6
<212> TYPE: RNA
<213> ORGANISM: Artificial sequence
<220> FEATURE:
<223> OTHER INFORMATION: RNA oligonucleotide
<220> FEATURE:
<221> NAME/KEY: repeat_unit
<222> LOCATION: (1)..(6)
<223> OTHER INFORMATION: The oligonucleotides may comprise 1-20 repeats

<400> SEQUENCE: 15 acacac                                                                    6

<210> SEQ ID NO 16
<211> LENGTH: 24
<212> TYPE: RNA
<213> ORGANISM: Artificial sequence
<220> FEATURE:
<223> OTHER INFORMATION: RNA oligonucleotide

<400> SEQUENCE: 16
uagggauagg gauagggaua ggga                                               24

<210> SEQ ID NO 17
<211> LENGTH: 20
<212> TYPE: RNA
<213> ORGANISM: Artificial sequence
<220> FEATURE:
<223> OTHER INFORMATION: RNA oligonucleotide

<400> SEQUENCE: 17
cagcagaaag cagcagaaag                                                    20

<210> SEQ ID NO 18
<211> LENGTH: 6
<212> TYPE: RNA
<213> ORGANISM: Artificial sequence
<220> FEATURE:
<223> OTHER INFORMATION: RNA oligonucleotide
<220> FEATURE:
<221> NAME/KEY: repeat_unit
<222> LOCATION: (1)..(6)
<223> OTHER INFORMATION: The oligonucleotides may comprise 1-20 repeats

<400> SEQUENCE: 18 agauag                                                                    6

<210> SEQ ID NO 19
<211> LENGTH: 5
<212> TYPE: RNA
<213> ORGANISM: Artificial sequence
<220> FEATURE:
<223> OTHER INFORMATION: RNA oligonucleotide
<220> FEATURE:
<221> NAME/KEY: repeat_unit
<222> LOCATION: (1)..(5)
<223> OTHER INFORMATION: The oligonucleotides may comprise 1-20 repeats

<400> SEQUENCE: 19 uuuuu                                                                     5

<210> SEQ ID NO 20
<211> LENGTH: 5
<212> TYPE: RNA
<213> ORGANISM: Artificial sequence
<220> FEATURE:
<223> OTHER INFORMATION: RNA oligonucleotide
<220> FEATURE:
<221> NAME/KEY: repeat_unit
```

```
<222> LOCATION: (1)..(5)
<223> OTHER INFORMATION: The oligonucleotides may comprise 1-20 repeats

<400> SEQUENCE: 20 aagaa                                                                    5

<210> SEQ ID NO 21
<211> LENGTH: 6
<212> TYPE: RNA
<213> ORGANISM: Artificial sequence
<220> FEATURE:
<223> OTHER INFORMATION: RNA oligonucleotide
<220> FEATURE:
<221> NAME/KEY: repeat_unit
<222> LOCATION: (1)..(6)
<223> OTHER INFORMATION: The oligonucleotides may comprise 1-20 repeats

<400> SEQUENCE: 21 cauuuu                                                                   6

<210> SEQ ID NO 22
<211> LENGTH: 6
<212> TYPE: RNA
<213> ORGANISM: Artificial sequence
<220> FEATURE:
<223> OTHER INFORMATION: RNA oligonucleotide
<220> FEATURE:
<221> NAME/KEY: repeat_unit
<222> LOCATION: (1)..(6)
<223> OTHER INFORMATION: The oligonucleotides may comprise 1-20 repeats

<400> SEQUENCE: 22 caaaag                                                                   6

<210> SEQ ID NO 23
<211> LENGTH: 6
<212> TYPE: RNA
<213> ORGANISM: Artificial sequence
<220> FEATURE:
<223> OTHER INFORMATION: RNA oligonucleotide
<220> FEATURE:
<221> NAME/KEY: repeat_unit
<222> LOCATION: (1)..(6)
<223> OTHER INFORMATION: The oligonucleotides may comprise 1-20 repeats

<400> SEQUENCE: 23 uuuuuu                                                                   6

<210> SEQ ID NO 24
<211> LENGTH: 5
<212> TYPE: RNA
<213> ORGANISM: Artificial sequence
<220> FEATURE:
<223> OTHER INFORMATION: RNA oligonucleotide
<220> FEATURE:
<221> NAME/KEY: repeat_unit
<222> LOCATION: (1)..(5)
<223> OTHER INFORMATION: The oligonucleotides may comprise 1-20 repeats

<400> SEQUENCE: 24 auaua                                                                    5

<210> SEQ ID NO 25
<211> LENGTH: 6
<212> TYPE: RNA
<213> ORGANISM: Artificial sequence
<220> FEATURE:
<223> OTHER INFORMATION: RNA oligonucleotide
<220> FEATURE:
```

```
<221> NAME/KEY: repeat_unit
<222> LOCATION: (1)..(6)
<223> OTHER INFORMATION: The oligonucleotides may comprise 1-20 repeats

<400> SEQUENCE: 25 acgacg                                                                       6

<210> SEQ ID NO 26
<211> LENGTH: 6
<212> TYPE: RNA
<213> ORGANISM: Artificial sequence
<220> FEATURE:
<223> OTHER INFORMATION: RNA oligonucleotide
<220> FEATURE:
<221> NAME/KEY: repeat_unit
<222> LOCATION: (1)..(6)
<223> OTHER INFORMATION: The oligonucleotides may comprise 1-20 repeats

<400> SEQUENCE: 26 gaguag                                                                       6

<210> SEQ ID NO 27
<211> LENGTH: 5
<212> TYPE: RNA
<213> ORGANISM: Artificial sequence
<220> FEATURE:
<223> OTHER INFORMATION: RNA oligonucleotide
<220> FEATURE:
<221> NAME/KEY: repeat_unit
<222> LOCATION: (1)..(5)
<223> OTHER INFORMATION: The oligonucleotides may comprise 1-20 repeats

<400> SEQUENCE: 27 uggaa                                                                        5

<210> SEQ ID NO 28
<211> LENGTH: 6
<212> TYPE: RNA
<213> ORGANISM: Artificial sequence
<220> FEATURE:
<223> OTHER INFORMATION: RNA oligonucleotide
<220> FEATURE:
<221> NAME/KEY: repeat_unit
<222> LOCATION: (1)..(6)
<223> OTHER INFORMATION: The oligonucleotides may comprise 1-20 repeats

<400> SEQUENCE: 28 uggggu                                                                       6

<210> SEQ ID NO 29
<211> LENGTH: 5
<212> TYPE: RNA
<213> ORGANISM: Artificial sequence
<220> FEATURE:
<223> OTHER INFORMATION: RNA oligonucleotide
<220> FEATURE:
<221> NAME/KEY: repeat_unit
<222> LOCATION: (1)..(5)
<223> OTHER INFORMATION: The oligonucleotides may comprise 1-20 repeats

<400> SEQUENCE: 29 uaauu                                                                        5

<210> SEQ ID NO 30
<211> LENGTH: 6
<212> TYPE: RNA
<213> ORGANISM: Artificial sequence
<220> FEATURE:
<223> OTHER INFORMATION: RNA oligonucleotide
```

```
<220> FEATURE:
<221> NAME/KEY: repeat_unit
<222> LOCATION: (1)..(6)
<223> OTHER INFORMATION: The oligonucleotides may comprise 1-20 repeats

<400> SEQUENCE: 30 aaucaa                                                                        6

<210> SEQ ID NO 31
<211> LENGTH: 7
<212> TYPE: RNA
<213> ORGANISM: Artificial sequence
<220> FEATURE:
<223> OTHER INFORMATION: RNA oligonucleotide
<220> FEATURE:
<221> NAME/KEY: repeat_unit
<222> LOCATION: (1)..(7)
<223> OTHER INFORMATION: The oligonucleotides may comprise 1-20 repeats

<400> SEQUENCE: 31 uuugguu                                                                       7

<210> SEQ ID NO 32
<211> LENGTH: 5
<212> TYPE: RNA
<213> ORGANISM: Artificial sequence
<220> FEATURE:
<223> OTHER INFORMATION: RNA oligonucleotide
<220> FEATURE:
<221> NAME/KEY: repeat_unit
<222> LOCATION: (1)..(5)
<223> OTHER INFORMATION: The oligonucleotides may comprise 1-20 repeats

<400> SEQUENCE: 32 acuaa                                                                         5

<210> SEQ ID NO 33
<211> LENGTH: 6
<212> TYPE: RNA
<213> ORGANISM: Artificial sequence
<220> FEATURE:
<223> OTHER INFORMATION: RNA oligonucleotide
<220> FEATURE:
<221> NAME/KEY: repeat_unit
<222> LOCATION: (1)..(5)
<223> OTHER INFORMATION: The oligonucleotides may comprise 1-20 repeats

<400> SEQUENCE: 33 acuaac                                                                        6

<210> SEQ ID NO 34
<211> LENGTH: 6
<212> TYPE: RNA
<213> ORGANISM: Artificial sequence
<220> FEATURE:
<223> OTHER INFORMATION: RNA oligonucleotide
<220> FEATURE:
<221> NAME/KEY: repeat_unit
<222> LOCATION: (1)..(6)
<223> OTHER INFORMATION: The oligonucleotides may comprise 1-20 repeats

<400> SEQUENCE: 34 auaaaa                                                                        6

<210> SEQ ID NO 35
<211> LENGTH: 6
<212> TYPE: RNA
<213> ORGANISM: Artificial sequence
<220> FEATURE:
```

```
<223> OTHER INFORMATION: RNA oligonucleotide
<220> FEATURE:
<221> NAME/KEY: repeat_unit
<222> LOCATION: (1)..(5)
<223> OTHER INFORMATION: The oligonucleotides may comprise 1-20 repeats

<400> SEQUENCE: 35 cuuucc                                                                    6

<210> SEQ ID NO 36
<211> LENGTH: 6
<212> TYPE: RNA
<213> ORGANISM: Artificial sequence
<220> FEATURE:
<223> OTHER INFORMATION: RNA oligonucleotide
<220> FEATURE:
<221> NAME/KEY: repeat_unit
<222> LOCATION: (1)..(6)
<223> OTHER INFORMATION: The oligonucleotides may comprise 1-20 repeats

<400> SEQUENCE: 36 uuuccc                                                                    6

<210> SEQ ID NO 37
<211> LENGTH: 7
<212> TYPE: RNA
<213> ORGANISM: Artificial sequence
<220> FEATURE:
<223> OTHER INFORMATION: RNA oligonucleotide
<220> FEATURE:
<221> NAME/KEY: repeat_unit
<222> LOCATION: (1)..(7)
<223> OTHER INFORMATION: The oligonucleotides may comprise 1-20 repeats

<400> SEQUENCE: 37 ccaaccc                                                                   7

<210> SEQ ID NO 38
<211> LENGTH: 6
<212> TYPE: RNA
<213> ORGANISM: Artificial sequence
<220> FEATURE:
<223> OTHER INFORMATION: RNA oligonucleotide
<220> FEATURE:
<221> NAME/KEY: repeat_unit
<222> LOCATION: (1)..(6)
<223> OTHER INFORMATION: The oligonucleotides may comprise 1-20 repeats

<400> SEQUENCE: 38 gacggg                                                                    6

<210> SEQ ID NO 39
<211> LENGTH: 6
<212> TYPE: RNA
<213> ORGANISM: Artificial sequence
<220> FEATURE:
<223> OTHER INFORMATION: RNA oligonucleotide
<220> FEATURE:
<221> NAME/KEY: repeat_unit
<222> LOCATION: (1)..(6)
<223> OTHER INFORMATION: The oligonucleotides may comprise 1-20 repeats

<400> SEQUENCE: 39 augaca                                                                    6

<210> SEQ ID NO 40
<211> LENGTH: 6
<212> TYPE: RNA
<213> ORGANISM: Artificial sequence
```

```
<220> FEATURE:
<223> OTHER INFORMATION: RNA oligonucleotide
<220> FEATURE:
<221> NAME/KEY: repeat_unit
<222> LOCATION: (1)..(6)
<223> OTHER INFORMATION: The oligonucleotides may comprise 1-20 repeats

<400> SEQUENCE: 40 gacaag                                                                    6

<210> SEQ ID NO 41
<211> LENGTH: 6
<212> TYPE: RNA
<213> ORGANISM: Artificial sequence
<220> FEATURE:
<223> OTHER INFORMATION: RNA oligonucleotide
<220> FEATURE:
<221> NAME/KEY: repeat_unit
<222> LOCATION: (1)..(6)
<223> OTHER INFORMATION: The oligonucleotides may comprise 1-20 repeats

<400> SEQUENCE: 41 gugugu                                                                    6

<210> SEQ ID NO 42
<211> LENGTH: 6
<212> TYPE: RNA
<213> ORGANISM: Artificial sequence
<220> FEATURE:
<223> OTHER INFORMATION: RNA oligonucleotide
<220> FEATURE:
<221> NAME/KEY: repeat_unit
<222> LOCATION: (1)..(6)
<223> OTHER INFORMATION: The oligonucleotides may comprise 1-20 repeats

<400> SEQUENCE: 42 ugcaug                                                                    6

<210> SEQ ID NO 43
<211> LENGTH: 24
<212> TYPE: RNA
<213> ORGANISM: Artificial sequence
<220> FEATURE:
<223> OTHER INFORMATION: RNA oligonucleotide

<400> SEQUENCE: 43
ugcaugugca ugugcaugug caug                                               24

<210> SEQ ID NO 44
<211> LENGTH: 5
<212> TYPE: RNA
<213> ORGANISM: Artificial sequence
<220> FEATURE:
<223> OTHER INFORMATION: RNA oligonucleotide
<220> FEATURE:
<221> NAME/KEY: repeat_unit
<222> LOCATION: (1)..(5)
<223> OTHER INFORMATION: The oligonucleotides may comprise 1-20 repeats

<400> SEQUENCE: 44 ugcau                                                                     5

<210> SEQ ID NO 45
<211> LENGTH: 5
<212> TYPE: RNA
<213> ORGANISM: Artificial sequence
<220> FEATURE:
<223> OTHER INFORMATION: RNA oligonucleotide
<220> FEATURE:
```

```
<221> NAME/KEY: repeat_unit
<222> LOCATION: (1)..(5)
<223> OTHER INFORMATION: The oligonucleotides may comprise 1-20 repeats

<400> SEQUENCE: 45 gcaug                                                                      5

<210> SEQ ID NO 46
<211> LENGTH: 5
<212> TYPE: RNA
<213> ORGANISM: Artificial sequence
<220> FEATURE:
<223> OTHER INFORMATION: RNA oligonucleotide
<220> FEATURE:
<221> NAME/KEY: repeat_unit
<222> LOCATION: (1)..(5)
<223> OTHER INFORMATION: The oligonucleotides may comprise 1-20 repeats

<400> SEQUENCE: 46 gugug                                                                      5

<210> SEQ ID NO 47
<211> LENGTH: 6
<212> TYPE: RNA
<213> ORGANISM: Artificial sequence
<220> FEATURE:
<223> OTHER INFORMATION: RNA oligonucleotide
<220> FEATURE:
<221> NAME/KEY: repeat_unit
<222> LOCATION: (1)..(6)
<223> OTHER INFORMATION: The oligonucleotides may comprise 1-20 repeats

<400> SEQUENCE: 47 uuuucu                                                                     6

<210> SEQ ID NO 48
<211> LENGTH: 5
<212> TYPE: RNA
<213> ORGANISM: Artificial sequence
<220> FEATURE:
<223> OTHER INFORMATION: RNA oligonucleotide
<220> FEATURE:
<221> NAME/KEY: repeat_unit
<222> LOCATION: (1)..(5)
<223> OTHER INFORMATION: The oligonucleotides may comprise 1-20 repeats

<400> SEQUENCE: 48 cgcgc                                                                      5

<210> SEQ ID NO 49
<211> LENGTH: 6
<212> TYPE: RNA
<213> ORGANISM: Artificial sequence
<220> FEATURE:
<223> OTHER INFORMATION: RNA oligonucleotide
<220> FEATURE:
<221> NAME/KEY: repeat_unit
<222> LOCATION: (1)..(6)
<223> OTHER INFORMATION: The oligonucleotides may comprise 1-20 repeats

<400> SEQUENCE: 49 agaaga                                                                     6

<210> SEQ ID NO 50
<211> LENGTH: 28
<212> TYPE: RNA
<213> ORGANISM: Artificial sequence
<220> FEATURE:
<223> OTHER INFORMATION: RNA oligonucleotide
```

```
<400> SEQUENCE: 50
cgcaggacgc aggacgcagg acgcagga                                              28

<210> SEQ ID NO 51
<211> LENGTH: 28
<212> TYPE: RNA
<213> ORGANISM: Artificial sequence
<220> FEATURE:
<223> OTHER INFORMATION: RNA oligonucleotide

<400> SEQUENCE: 51
cacaggacac aggacacagg acacagga                                              28

<210> SEQ ID NO 52
<211> LENGTH: 6
<212> TYPE: RNA
<213> ORGANISM: Artificial sequence
<220> FEATURE:
<223> OTHER INFORMATION: RNA oligonucleotide
<220> FEATURE:
<221> NAME/KEY: repeat_unit
<222> LOCATION: (1)..(6)
<223> OTHER INFORMATION: The oligonucleotides may comprise 1-20 repeats

<400> SEQUENCE: 52 uggagu                                                                      6

<210> SEQ ID NO 53
<211> LENGTH: 6
<212> TYPE: RNA
<213> ORGANISM: Artificial sequence
<220> FEATURE:
<223> OTHER INFORMATION: RNA oligonucleotide
<220> FEATURE:
<221> NAME/KEY: repeat_unit
<222> LOCATION: (1)..(6)
<223> OTHER INFORMATION: The oligonucleotides may comprise 1-20 repeats

<400> SEQUENCE: 53 uccagu                                                                      6

<210> SEQ ID NO 54
<211> LENGTH: 6
<212> TYPE: RNA
<213> ORGANISM: Artificial sequence
<220> FEATURE:
<223> OTHER INFORMATION: RNA oligonucleotide
<220> FEATURE:
<221> NAME/KEY: repeat_unit
<222> LOCATION: (1)..(6)
<223> OTHER INFORMATION: The oligonucleotides may comprise 1-20 repeats

<400> SEQUENCE: 54 agaaga                                                                      6

<210> SEQ ID NO 55
<211> LENGTH: 6
<212> TYPE: RNA
<213> ORGANISM: Artificial sequence
<220> FEATURE:
<223> OTHER INFORMATION: RNA oligonucleotide
<220> FEATURE:
<221> NAME/KEY: repeat_unit
<222> LOCATION: (1)..(6)
<223> OTHER INFORMATION: The oligonucleotides may comprise 1-20 repeats

<400> SEQUENCE: 55
```

```
agggau                                                              6

<210> SEQ ID NO 56
<211> LENGTH: 6
<212> TYPE: RNA
<213> ORGANISM: Artificial sequence
<220> FEATURE:
<223> OTHER INFORMATION: RNA oligonucleotide
<220> FEATURE:
<221> NAME/KEY: misc_feature
<222> LOCATION: (1)..(1)
<223> OTHER INFORMATION: N6-Methyladenosine
<220> FEATURE:
<221> NAME/KEY: misc_feature
<222> LOCATION: (5)..(5)
<223> OTHER INFORMATION: N6-Methyladenosine

<400> SEQUENCE: 56 agggau                                                              6

<210> SEQ ID NO 57
<211> LENGTH: 8
<212> TYPE: RNA
<213> ORGANISM: Artificial sequence
<220> FEATURE:
<223> OTHER INFORMATION: RNA oligonucleotide
<220> FEATURE:
<221> NAME/KEY: repeat_unit
<222> LOCATION: (1)..(8)
<223> OTHER INFORMATION: The oligonucleotides may comprise 1-20 repeats

<400> SEQUENCE: 57 agacagac                                                            8

<210> SEQ ID NO 58
<211> LENGTH: 8
<212> TYPE: RNA
<213> ORGANISM: Artificial sequence
<220> FEATURE:
<223> OTHER INFORMATION: RNA oligonucleotide
<220> FEATURE:
<221> NAME/KEY: repeat_unit
<222> LOCATION: (1)..(8)
<223> OTHER INFORMATION: The oligonucleotides may comprise 1-20 repeats
<220> FEATURE:
<221> NAME/KEY: misc_feature
<222> LOCATION: (1)..(1)
<223> OTHER INFORMATION: N6-Methyladenosine
<220> FEATURE:
<221> NAME/KEY: misc_feature
<222> LOCATION: (3)..(3)
<223> OTHER INFORMATION: N6-Methyladenosine
<220> FEATURE:
<221> NAME/KEY: misc_feature
<222> LOCATION: (5)..(5)
<223> OTHER INFORMATION: N6-Methyladenosine
<220> FEATURE:
<221> NAME/KEY: misc_feature
<222> LOCATION: (7)..(7)
<223> OTHER INFORMATION: N6-Methyladenosine

<400> SEQUENCE: 58 agacagac                                                            8

<210> SEQ ID NO 59
<211> LENGTH: 6
<212> TYPE: RNA
<213> ORGANISM: Artificial sequence
<220> FEATURE:
<223> OTHER INFORMATION: RNA oligonucleotide
<220> FEATURE:
<221> NAME/KEY: repeat_unit
```

```
<222> LOCATION: (1)..(6)
<223> OTHER INFORMATION: The oligonucleotides may comprise 1-20 repeats
<220> FEATURE:
<221> NAME/KEY: misc_feature
<222> LOCATION: (2)..(2)
<223> OTHER INFORMATION: N6-Methyladenosine
<220> FEATURE:
<221> NAME/KEY: misc_feature
<222> LOCATION: (4)..(4)
<223> OTHER INFORMATION: N6-Methyladenosine

<400> SEQUENCE: 59 uagacu                                                                    6

<210> SEQ ID NO 60
<211> LENGTH: 6
<212> TYPE: RNA
<213> ORGANISM: Artificial sequence
<220> FEATURE:
<223> OTHER INFORMATION: RNA oligonucleotide
<220> FEATURE:
<221> NAME/KEY: repeat_unit
<222> LOCATION: (1)..(6)
<223> OTHER INFORMATION: The oligonucleotides may comprise 1-20 repeats

<400> SEQUENCE: 60 cucucu                                                                    6

<210> SEQ ID NO 61
<211> LENGTH: 24
<212> TYPE: RNA
<213> ORGANISM: Artificial sequence
<220> FEATURE:
<223> OTHER INFORMATION: RNA oligonucleotide

<400> SEQUENCE: 61
cucucucucu cucucucucu cucu                                               24

<210> SEQ ID NO 62
<211> LENGTH: 10
<212> TYPE: RNA
<213> ORGANISM: Artificial sequence
<220> FEATURE:
<223> OTHER INFORMATION: RNA oligonucleotide
<220> FEATURE:
<221> NAME/KEY: repeat_unit
<222> LOCATION: (1)..(10)
<223> OTHER INFORMATION: The oligonucleotides may comprise 1-20 repeats

<400> SEQUENCE: 62
uuuuuuuuag                                                               10

<210> SEQ ID NO 63
<211> LENGTH: 10
<212> TYPE: RNA
<213> ORGANISM: Artificial sequence
<220> FEATURE:
<223> OTHER INFORMATION: RNA oligonucleotide
<220> FEATURE:
<221> NAME/KEY: repeat_unit
<222> LOCATION: (1)..(10)
<223> OTHER INFORMATION: The oligonucleotides may comprise 1-20 repeats

<400> SEQUENCE: 63
uuuuuuucag                                                               10

<210> SEQ ID NO 64
<211> LENGTH: 10
<212> TYPE: RNA
```

```
<213> ORGANISM: Artificial sequence
<220> FEATURE:
<223> OTHER INFORMATION: RNA oligonucleotide
<220> FEATURE:
<221> NAME/KEY: repeat_unit
<222> LOCATION: (1)..(10)
<223> OTHER INFORMATION: The oligonucleotides may comprise 1-20 repeats

<400> SEQUENCE: 64
uuuuuuuaag                                                          10

<210> SEQ ID NO 65
<211> LENGTH: 17
<212> TYPE: RNA
<213> ORGANISM: Artificial sequence
<220> FEATURE:
<223> OTHER INFORMATION: RNA oligonucleotide
<220> FEATURE:
<221> NAME/KEY: repeat_unit
<222> LOCATION: (1)..(17)
<223> OTHER INFORMATION: The oligonucleotides may comprise 1-20 repeats

<400> SEQUENCE: 65
aaaaauuuuu uuucag                                                   17

<210> SEQ ID NO 66
<211> LENGTH: 17
<212> TYPE: RNA
<213> ORGANISM: Artificial sequence
<220> FEATURE:
<223> OTHER INFORMATION: RNA oligonucleotide
<220> FEATURE:
<221> NAME/KEY: repeat_unit
<222> LOCATION: (1)..(17)
<223> OTHER INFORMATION: The oligonucleotides may comprise 1-20 repeats

<400> SEQUENCE: 66
uuuaauuuuu uuucag                                                   17

<210> SEQ ID NO 67
<211> LENGTH: 22
<212> TYPE: DNA
<213> ORGANISM: Artificial sequence
<220> FEATURE:
<223> OTHER INFORMATION: Single strand DNA oligonucleotide

<400> SEQUENCE: 67
agatcctgaa ggagctggag ga                                            22

<210> SEQ ID NO 68
<211> LENGTH: 18
<212> TYPE: DNA
<213> ORGANISM: Artificial sequence
<220> FEATURE:
<223> OTHER INFORMATION: Single strand DNA oligonucleotide

<400> SEQUENCE: 68
ggtcgaggaa gtgttggg                                                 18

<210> SEQ ID NO 69
<211> LENGTH: 22
<212> TYPE: DNA
<213> ORGANISM: Artificial sequence
<220> FEATURE:
<223> OTHER INFORMATION: Single strand DNA oligonucleotide

<400> SEQUENCE: 69
gctgcgacct gtggagcctg gg                                            22
```

<210> SEQ ID NO 70
<211> LENGTH: 22
<212> TYPE: DNA
<213> ORGANISM: Artificial sequence
<220> FEATURE:
<223> OTHER INFORMATION: Single strand DNA oligonucleotide

<400> SEQUENCE: 70
gatgggaggg tcaggcgtgg tc                                    22

<210> SEQ ID NO 71
<211> LENGTH: 22
<212> TYPE: DNA
<213> ORGANISM: Artificial sequence
<220> FEATURE:
<223> OTHER INFORMATION: Single strand DNA oligonucleotide

<400> SEQUENCE: 71
gaggaggaag tgactgtccc ac                                    22

<210> SEQ ID NO 72
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 72
cgtaatcccc aaaacagtgc                                       20

<210> SEQ ID NO 73
<211> LENGTH: 23
<212> TYPE: DNA
<213> ORGANISM: Artificial sequence
<220> FEATURE:
<223> OTHER INFORMATION: Single strand DNA oligonucleotide

<400> SEQUENCE: 73
tcatcatagt gttcctgcat ctc                                   23

<210> SEQ ID NO 74
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 74
gccattggag agctgtcttc                                       20

<210> SEQ ID NO 75
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 75
gggccatctg gaacataaga                                       20

<210> SEQ ID NO 76
<211> LENGTH: 20
<212> TYPE: DNA
<213> ORGANISM: Artificial sequence
<220> FEATURE:

<223> OTHER INFORMATION: Single strand DNA oligonucleotide

<400> SEQUENCE: 76
aaattaaatg agaccacgga                                           20

<210> SEQ ID NO 77
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 77
tgacatcaca gccaagtgta                                           20

<210> SEQ ID NO 78
<211> LENGTH: 19
<212> TYPE: DNA
<213> ORGANISM: Artificial sequence
<220> FEATURE:
<223> OTHER INFORMATION: Single strand DNA oligonucleotide

<400> SEQUENCE: 78
ctgtcaacgc gcaggactt                                            19

<210> SEQ ID NO 79
<211> LENGTH: 18
<212> TYPE: DNA
<213> ORGANISM: Artificial sequence
<220> FEATURE:
<223> OTHER INFORMATION: Single strand DNA oligonucleotide

<400> SEQUENCE: 79
ggggctctgg tctgcgat                                             18

<210> SEQ ID NO 80
<211> LENGTH: 21
<212> TYPE: DNA
<213> ORGANISM: Artificial sequence
<220> FEATURE:
<223> OTHER INFORMATION: Single strand DNA oligonucleotide

<400> SEQUENCE: 80
caaattcggt acatcctcga c                                         21

<210> SEQ ID NO 81
<211> LENGTH: 21
<212> TYPE: DNA
<213> ORGANISM: Artificial sequence
<220> FEATURE:
<223> OTHER INFORMATION: Single strand DNA oligonucleotide

<400> SEQUENCE: 81
gaaggttcag gttgttttct g                                         21

<210> SEQ ID NO 82
<211> LENGTH: 21
<212> TYPE: DNA
<213> ORGANISM: Artificial sequence
<220> FEATURE:
<223> OTHER INFORMATION: Single strand DNA oligonucleotide

<400> SEQUENCE: 82
ccgaggtgta tgtatgagtg t                                         21

```
<210> SEQ ID NO 83
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 83
ctgtgtttgg agtgggtttc                                                  20

<210> SEQ ID NO 84
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 84
ttcccagtat ggcacaatga                                                  20

<210> SEQ ID NO 85
<211> LENGTH: 21
<212> TYPE: DNA
<213> ORGANISM: Artificial sequence
<220> FEATURE:
<223> OTHER INFORMATION: Single strand DNA oligonucleotide

<400> SEQUENCE: 85
ccaagcagga tccccatctg c                                                21

<210> SEQ ID NO 86
<211> LENGTH: 21
<212> TYPE: DNA
<213> ORGANISM: Artificial sequence
<220> FEATURE:
<223> OTHER INFORMATION: Single strand DNA oligonucleotide

<400> SEQUENCE: 86
gaacaccggc ctgtttatga g                                                21

<210> SEQ ID NO 87
<211> LENGTH: 21
<212> TYPE: DNA
<213> ORGANISM: Artificial sequence
<220> FEATURE:
<223> OTHER INFORMATION: Single strand DNA oligonucleotide

<400> SEQUENCE: 87
aagtgcttct gcctccgaga g                                                21

<210> SEQ ID NO 88
<211> LENGTH: 21
<212> TYPE: DNA
<213> ORGANISM: Artificial sequence
<220> FEATURE:
<223> OTHER INFORMATION: Single strand DNA oligonucleotide

<400> SEQUENCE: 88
tcaataaggg gtcataggtg g                                                21

<210> SEQ ID NO 89
<211> LENGTH: 20
<212> TYPE: DNA
<213> ORGANISM: Artificial sequence
<220> FEATURE:
<223> OTHER INFORMATION: Single strand DNA oligonucleotide
```

<400> SEQUENCE: 89
aggcttaggt agggattggc                                               20

<210> SEQ ID NO 90
<211> LENGTH: 21
<212> TYPE: DNA
<213> ORGANISM: Artificial sequence
<220> FEATURE:
<223> OTHER INFORMATION: Single strand DNA oligonucleotide

<400> SEQUENCE: 90
ggagctggag gtgatgactg c                                             21

<210> SEQ ID NO 91
<211> LENGTH: 21
<212> TYPE: DNA
<213> ORGANISM: Artificial sequence
<220> FEATURE:
<223> OTHER INFORMATION: Single strand DNA oligonucleotide

<400> SEQUENCE: 91
cttcagcttc tgctgctgca c                                             21

<210> SEQ ID NO 92
<211> LENGTH: 17
<212> TYPE: DNA
<213> ORGANISM: Artificial sequence
<220> FEATURE:
<223> OTHER INFORMATION: Single strand DNA oligonucleotide

<400> SEQUENCE: 92
cgtggacatc cgcaaag                                                  17

<210> SEQ ID NO 93
<211> LENGTH: 17
<212> TYPE: DNA
<213> ORGANISM: Artificial sequence
<220> FEATURE:
<223> OTHER INFORMATION: Single strand DNA oligonucleotide

<400> SEQUENCE: 93
ggaaggtgga cagcgag                                                  17

<210> SEQ ID NO 94
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 94
ctctcaaggt gtttgacggc                                               20

<210> SEQ ID NO 95
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 95
tttattgggc tcagaccagg                                               20

<210> SEQ ID NO 96
<211> LENGTH: 21

```
<212> TYPE: DNA
<213> ORGANISM: Artificial sequence
<220> FEATURE:
<223> OTHER INFORMATION: Single strand DNA oligonucleotide

<400> SEQUENCE: 96
agcagccggt catgtttgca c                                         21

<210> SEQ ID NO 97
<211> LENGTH: 28
<212> TYPE: DNA
<213> ORGANISM: Artificial sequence
<220> FEATURE:
<223> OTHER INFORMATION: Single strand DNA oligonucleotide

<400> SEQUENCE: 97
actcagcatc aatcttattt gaagtctc                                  28

<210> SEQ ID NO 98
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 98
gctggagagc atgatcaaga                                           20

<210> SEQ ID NO 99
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 99
acttgaggct cgcacaagtt                                           20

<210> SEQ ID NO 100
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 100
aggacgatta tggccccact                                           20

<210> SEQ ID NO 101
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 101
ctgcatctga gcctgtgata                                           20

<210> SEQ ID NO 102
<211> LENGTH: 22
<212> TYPE: DNA
<213> ORGANISM: Artificial sequence
<220> FEATURE:
<223> OTHER INFORMATION: Single strand DNA oligonucleotide

<400> SEQUENCE: 102
```
gattctgctt ttggagagac ac                                            22

<210> SEQ ID NO 103
<211> LENGTH: 22
<212> TYPE: DNA
<213> ORGANISM: Artificial sequence
<220> FEATURE:
<223> OTHER INFORMATION: Single strand DNA oligonucleotide

<400> SEQUENCE: 103
caccgatgag gacaccacag tc                                            22

<210> SEQ ID NO 104
<211> LENGTH: 22
<212> TYPE: DNA
<213> ORGANISM: Artificial sequence
<220> FEATURE:
<223> OTHER INFORMATION: Single strand DNA oligonucleotide

<400> SEQUENCE: 104
ggttcgtctg cgttattggg gc                                            22

<210> SEQ ID NO 105
<211> LENGTH: 25
<212> TYPE: DNA
<213> ORGANISM: Artificial sequence
<220> FEATURE:
<223> OTHER INFORMATION: Single strand DNA oligonucleotide

<400> SEQUENCE: 105
gtccatctgc tcactcttat gtgac                                         25

<210> SEQ ID NO 106
<211> LENGTH: 25
<212> TYPE: DNA
<213> ORGANISM: Artificial sequence
<220> FEATURE:
<223> OTHER INFORMATION: Single strand DNA oligonucleotide

<400> SEQUENCE: 106
cctccataag agacagatgg ggaaa                                         25

<210> SEQ ID NO 107
<211> LENGTH: 25
<212> TYPE: DNA
<213> ORGANISM: Artificial sequence
<220> FEATURE:
<223> OTHER INFORMATION: Single strand DNA oligonucleotide

<400> SEQUENCE: 107
ggtcagacag aaagatgagg atgag                                         25

<210> SEQ ID NO 108
<211> LENGTH: 25
<212> TYPE: DNA
<213> ORGANISM: Artificial sequence
<220> FEATURE:
<223> OTHER INFORMATION: Single strand DNA oligonucleotide

<400> SEQUENCE: 108
ttatcagggt tgctcaggcc tgaca                                         25

<210> SEQ ID NO 109
<211> LENGTH: 25
<212> TYPE: DNA
<213> ORGANISM: Artificial sequence

```
<220> FEATURE:
<223> OTHER INFORMATION: Single strand DNA oligonucleotide

<400> SEQUENCE: 109
caagtacttc accaatgctt ggtgc                                          25

<210> SEQ ID NO 110
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 110
cgttgtagca gtagtagtac                                                20

<210> SEQ ID NO 111
<211> LENGTH: 21
<212> TYPE: DNA
<213> ORGANISM: Artificial sequence
<220> FEATURE:
<223> OTHER INFORMATION: Single strand DNA oligonucleotide

<400> SEQUENCE: 111
aagacaaccc caaggctctc a                                              21

<210> SEQ ID NO 112
<211> LENGTH: 21
<212> TYPE: DNA
<213> ORGANISM: Artificial sequence
<220> FEATURE:
<223> OTHER INFORMATION: Single strand DNA oligonucleotide

<400> SEQUENCE: 112
cctttggaac ggtgtgattg a                                              21

<210> SEQ ID NO 113
<211> LENGTH: 9
<212> TYPE: DNA
<213> ORGANISM: Artificial Sequence
<220> FEATURE:
<223> OTHER INFORMATION: a 5' exon-intron junction (or splice site)
      consensus sequence

<400> SEQUENCE: 113 caggtaagt                                                            9

<210> SEQ ID NO 114
<211> LENGTH: 15
<212> TYPE: DNA
<213> ORGANISM: Artificial Sequence
<220> FEATURE:
<223> OTHER INFORMATION: 3' splice site consensus sequence
<220> FEATURE:
<221> NAME/KEY: repeat_unit
<222> LOCATION: (1)..(1)
<223> OTHER INFORMATION: The oligonucleotides may comprise 3-12 repeats

<400> SEQUENCE: 114
yyyyyyyyyy yycag                                                     15
```